United States Patent
Kronberg

(10) Patent No.: US 7,117,034 B2
(45) Date of Patent: Oct. 3, 2006

(54) APPARATUS AND METHOD FOR BIOELECTRIC STIMULATION, HEALING ACCELERATION, PAIN RELIEF, OR PATHOGEN DEVITALIZATION

(75) Inventor: James W. Kronberg, Aiken, SC (US)

(73) Assignee: Healthonics, Inc., Atlanta, GA (US)

( * ) Notice: Subject to any disclaimer, the term of this patent is extended or adjusted under 35 U.S.C. 154(b) by 0 days.

(21) Appl. No.: 10/875,801

(22) Filed: Jun. 24, 2004

(65) Prior Publication Data

US 2004/0267333 A1    Dec. 30, 2004

Related U.S. Application Data

(60) Provisional application No. 60/480,890, filed on Jun. 24, 2003.

(51) Int. Cl.
*A61N 1/36* (2006.01)

(52) U.S. Cl. .............................. 607/2; 607/46; 607/50; 607/51

(58) Field of Classification Search ............... 607/4, 607/5, 68–70
See application file for complete search history.

(56) References Cited

U.S. PATENT DOCUMENTS

| | | |
|---|---|---|
| 3,294,092 A | 12/1966 | Landauer |
| 3,516,413 A | 6/1970 | McDonald et al. |
| 3,589,370 A | 6/1971 | McDonald |
| 3,946,745 A | 3/1976 | Hsiang-Lai et al. |
| 4,026,304 A | 5/1977 | Levy |
| 4,255,790 A | 3/1981 | Hondeghem |
| 4,338,945 A | 7/1982 | Kosugi et al. |
| 4,340,063 A | 7/1982 | Maurer |
| 4,431,000 A | 2/1984 | Butler et al. |
| 4,541,432 A | 9/1985 | Molina-Negro et al. |
| 4,580,570 A | 4/1986 | Sarrell et al. |
| 4,592,359 A | 6/1986 | Galbraith |
| 4,600,010 A | 7/1986 | Dugot |
| 4,607,639 A | 8/1986 | Tanagho et al. |
| 4,612,934 A | 9/1986 | Borkan |
| 4,754,759 A | 7/1988 | Allocca |
| 4,784,142 A | 11/1988 | Liss et al. |
| 4,846,181 A | 7/1989 | Miller |
| 4,895,154 A | 1/1990 | Bartelt et al. |
| 4,924,880 A * | 5/1990 | O'Neill et al. ................ 607/47 |
| 4,938,223 A | 7/1990 | Charters et al. |
| 4,947,844 A | 8/1990 | McDermott |
| 5,018,524 A | 5/1991 | Gu et al. |
| 5,063,929 A | 11/1991 | Bartelt et al. |
| 5,067,495 A | 11/1991 | Brehm |
| 5,097,833 A * | 3/1992 | Campos ....................... 607/68 |
| 5,109,847 A | 5/1992 | Liss et al. |
| 5,117,826 A | 6/1992 | Bartelt et al. |
| 5,217,009 A | 6/1993 | Kronberg |

(Continued)

Primary Examiner—Carl Layno
(74) Attorney, Agent, or Firm—KilpatrickStockton LLP

(57) ABSTRACT

An method and method for generating an electrical signal for use in biomedical applications, including two timing-interval generators, each optionally driving a multistep sequencer; analog, digital or hybrid means for combining the resulting timed signals into a complex electrical signal; optional filtering means for blocking direct current, removing selected frequency components from the resulting signal, and/or providing voltage step-up if needed; and conductive means for coupling the resulting signal to a human or animal body, food, beverage or other liquid, cell or tissue culture, or pharmaceutical material, in order to relieve pain, stimulate healing or growth, enhance the production of specific biochemicals, or devitalize selected types of organisms.

113 Claims, 34 Drawing Sheets

U.S. PATENT DOCUMENTS

| | | |
|---|---|---|
| 5,350,414 A | 9/1994 | Kolen |
| 5,413,596 A | 5/1995 | Kronberg |
| 5,487,759 A | 1/1996 | Bastyr et al. |
| 5,565,005 A | 10/1996 | Erickson et al. |
| 5,601,608 A * | 2/1997 | Mouchawar ............... 607/5 |
| 5,723,001 A | 3/1998 | Pilla et al. |
| 5,766,231 A | 6/1998 | Erickson et al. |
| 5,851,223 A | 12/1998 | Liss et al. |
| 5,974,342 A | 10/1999 | Petrofsky |
| 6,011,994 A | 1/2000 | Kronberg |
| 6,236,890 B1 * | 5/2001 | Oldham ..................... 607/68 |
| 6,321,119 B1 | 11/2001 | Kronberg |
| 6,505,079 B1 * | 1/2003 | Foster et al. ............... 607/68 |
| 6,535,767 B1 | 3/2003 | Kronberg |
| 6,701,190 B1 * | 3/2004 | Gliner ....................... 607/62 |
| 6,865,423 B1 * | 3/2005 | Oldham ..................... 607/48 |
| 2004/0019370 A1 * | 1/2004 | Gliner et al. ............... 607/48 |

* cited by examiner

APPARATUS AND METHOD FOR BIOELECTRIC STIMULATION, HEALING ACCELERATION, PAIN RELIEF, OR PATHOGEN DEVITALIZATION

CROSS-REFERENCE TO RELATED APPLICATIONS

The present application claims benefit of U.S. Provisional Application Ser. No. 60/480,890 filed Jun. 24, 2003.

TECHNICAL FIELD OF THE INVENTION

The present invention relates to a pulsed signal generator for biomedical applications. In particular, the present invention relates to a light-weight, compact pulsed signal generator that produces unique output waveforms based on a plurality of relatively long primary timing intervals $T_1$, $T_2$ and so forth, forming in succession a primary repeating cycle; a plurality of shorter secondary timing intervals $t_1$, $t_2$ and so forth, into which at least one of said primary intervals is divided, and forming in succession a secondary repeating cycle which continues throughout the length of that primary interval, while at least one other of said primary intervals is not so divided; a plurality of constant voltage or current levels $L_1$, $L_2$ and so forth, one of which is selected during each primary or secondary timing interval.

In an optional embodiment, the output waveform comprises an equalizing pulse immediately following the pulse burst. In yet another embodiment, the output waveform comprises a gradual step-in and step-out period optionally combined with an equalizing pulse.

In addition the invention comprises a circuit for combining these selected levels into an electrical signal having a stepped waveform and a circuit for further processing this signal to change its amplitude or remove undesired D.C. or frequency components.

The present invention further includes a conductive system for applying such a signal to the human body, animal body, isolated tissues or cell cultures, foods, beverages or other materials in order to relieve pain, stimulate healing, or devitalize selected pathogenic organisms which may be present.

BACKGROUND ART

Injuries, infections and degenerative conditions are major sources of pain, lost function inconvenience, expense, lost work (and leisure) time, and diminished productivity. The problems associated with these conditions grow worse with age, since an injury which would heal quickly in a young, healthy person takes much longer in one who is older, in poor health, or both. In demographically aging societies, such as those now seen in most of the industrialized nations, these social and economic impacts will become increasingly magnified over the course of the next several decades.

While it is difficult to estimate the total cost of such conditions, leaving aside their impact on quality of life, the total surely amounts to many billions of dollars per year in the United States alone. For example, between five and ten million United States residents suffer broken bones every year, with many of these cases involving multiple fractures. In a young, healthy patient, many fractures need to be immobilized in a cast for six weeks or more. Even after the cast is removed, the patient's activities are frequently restricted until the healed bone regains its full strength. In the elderly, in persons with poor health or malnutrition, in patients with multiple fractures, or in patients with conditions that impact healing processes, fractures heal more slowly. In some cases, the fractures do not heal at all, resulting in the conditions known as "nonunion", "nonunion fracture" or "delayed union" which sometimes persist for a lifetime.

As a result, an estimated quarter-million person-years of productivity are lost in the United States every year due to bone fractures alone. Similar statistics can be generated not only for other classes of traumatic injury, but also for chronic conditions such as osteoarthritis, osteoporosis, ulcers (diabetic, decubitus, veous stasis and arteriol insufficiency) damaged ligaments, tendonitis, and repetitive stress injuries (including the conditions commonly known as "tennis elbow" and carpal tunnel syndrome).

Since the 1960s, it has been increasingly recognized that the human body generates a host of low-level electric signals as a result of injury, stress and other factors; that these signals play a necessary part in healing and disease-recovery processes; and that such processes can be accelerated by providing artificially-generated signals which mimic the body's own in frequency, waveform and strength. Such "mimic" signals have been shown to have many effects in the body, including helping to direct mobile cells such as fibroblasts and macrophages to sites where they are needed (galvanotaxis) and causing the release of cell growth factors such as transforming growth factor beta (TGF-$\beta$) and insulin-like growth factor (IGF). The results can include more rapid healing of skin and muscle wounds, including chronic ulcers such as those resulting from diabetes, with minimal scarring; the mending of broken bones, including most nonunion fractures; the regrowth of injured or severed nerves; the repair of tissues damaged by repetitive motion, as in tendonitis and osteoarthritis; and the reduction of swelling, inflammation, and pain, including chronic pain for which the usual drug-based treatments do not bring satisfactory relief.

Some of the body's signals, such as the "injury potential" or "current of injury" measured in wounds, are DC (direct current) only, changing slowly with time. It has been found that bone fracture repair and nerve regrowth are typically faster than usual in the vicinity of a negative electrode but slower near a positive one, where in some cases tissue atrophy or necrosis may occur. For this reason, most recent research has focused on higher-frequency, more complex signals often with no net DC component.

While most complex-signal studies to date have been performed on bone fracture healing, the commonality of basic physiological processes in all tissues suggests that appropriate signals will be effective in accelerating many other healing and disease-recovery processes, although not all such signals will necessarily be alike. Indeed, specific frequency and waveform combinations have been observed to combat osteoarthritis and insomnia, stimulate hair growth, reduce swelling and inflammation, fight localized infection, speed the healing of injured soft tissues including skin, nerves, ligaments and tendons, and relieve pain without the substituted discomfort of TENS (transcutaneous electric nerve stimulation).

FIG. 1 shows a schematic view of a waveform 20 which has been found effective in stimulating bone fracture healing, where a line 22 represents the waveform on a short time scale, a line 24 represents the same waveform on a longer time scale, levels 26 and 28 represent two different characteristic values of voltage or current, and intervals 30, 32, 34 and 36 represent the timing between specific transitions. Levels 26 and 28 are usually selected so that, when averaged over a full cycle of the waveform, there is no net direct-current (D.C.) component. In real-world applications, waveform such as 20 is typically modified in that all voltages or currents decay exponentially toward some intermediate level between levels 26 and 28, with a decay time constant preferably longer than interval 34. The result is represented by a line 38.

In a typical commercially-available device for treating fracture nonunions, interval 30 is about 200 microseconds, interval 32 about 30 microseconds, interval 34 about 5 milliseconds, and interval 36 about 60 milliseconds. Alternate repetition of intervals 30 and 32 generates pulse bursts 40, each of the length of interval 34, separated by intervals of length 36 in which the signal remains approximately at level 28. Each waveform 38 thus consists of rectangular waves alternating between levels 26 and 28 at a frequency of about 4400 Hz and a duty cycle of about 85%. The pulse bursts are repeated at a frequency of about 15 Hz and a duty cycle of about 7.5%, alternating with periods of substantially no signal.

However, tissues may respond differently to markedly different frequencies and waveforms. For example, the waveform of FIG. 1 is effective in speeding the healing of a bone fracture but much less so in slowing the progress of osteoporosis. On the other hand, a waveform 50 (FIG. 2) consisting of single pulses 52 of polarity 26 lasting approximately 350–400 microseconds each, alternating with intervals 54 of polarity 28 at a frequency of approximately 60–75 Hz, can slow or even reverse osteoporosis but has little effect on fracture repair. Again, the exact waveform and frequency for each application may vary.

The signal intensity may also vary; indeed, more powerful signals often give no more benefit than weaker ones, and sometimes less. This paradoxical relationship is shown schematically in FIG. 3, where a line 60 represents the magnitude of the healing effect at various signal intensities. For a typical signal (such as the signal of FIG. 1), a peak effectiveness 62 typically falls somewhere between one and ten microamperes per square centimeter ($\mu A/cm^2$), and a crossover point 64 at about a hundred times this value. Beyond point 64, the signal may slow healing or may itself cause further injury. Similar responses are seen in other biological processes that are responsive to electrical stimulation, including cell division, protein and DNA synthesis, gene expression, and intracellular second-messenger concentrations. For example, while conventional TENS can block pain perception with a relatively strong signal, much as a jamming signal blocks radio communication, it can also lead to progressively worsening injury since the pain's warning function has also been defeated.

Tests using sine waves, square waves, frequencies above about 50 KHz, or waveforms generally resembling that in FIG. 1 but with duty cycles approaching 50% or with excessively fast or slow rise times, have shown much lower effectiveness at otherwise comparable power levels.

Many different types of electrical stimulation devices are available to consumers and medical professionals, producing many different waveforms ranging from constant-current or constant voltage (DC) through low-frequency to high-frequency waveforms. In general, the lower-frequency waveforms and high-frequency pulses within a low-frequency envelope tend to be aimed at tissue-healing applications, while higher-frequency waveforms are used for pain relief.

Another field of application of electronic waveforms is in the area of pathogen devitalization. It has been shown that some viral or bacterial organisms can be destroyed or devitalized (made unable to infect or reproduce) by the application in vitro of chosen electric signals. Since signal levels for this use are typically much higher than in healing stimulation, however, in vivo applications are still a matter of some controversy.

Electrical stimulation is widely used in tissue healing applications. Here, Petrofsky (U.S. Pat. No. 5,974,342) shows a microprocessor-controlled apparatus for treating injured tissue, tendon, or muscle by applying a therapeutic current. The apparatus has several channels that provide biphasic constant voltage or current, including a 100–300 microsecond positive phase, a 200–750 microsecond interphase, and a 100–300 microsecond negative phase occurring once every 12.5–25 milliseconds.

Pilla et al. (U.S. Pat. No. 5,723,001) disclose an apparatus for therapeutically treating human body tissue with pulsed radio-frequency electromagnetic radiation. The apparatus generates bursts of pulses having a frequency of 1–100 MHz, with 100–100,000 pulses per burst, and a burst repetition rate of 0.01–1000 Hz. The pulse envelope can be regular, irregular, or random.

Bartelt et al. (U.S. Pat. No. 5,117,826) discloses an apparatus and method for combined nerve fiber and body tissue stimulation. The apparatus generates biphasic pulse pairs for nerve fiber stimulation, and a net DC stimulus for body tissue treatment (provided by biphasic pulse trains having a greater number of negative than positive pulses). In U.S. Pat. No. 4,895,154, Bartelt, et al. describe a device for stimulating enhanced healing of soft tissue wounds that includes a plurality of signal generators for generating output pulses. The intensity, polarity, and rate of the output pulses can be varied via a series of control knobs or switches on the front panel of the device.

Gu et al. (U.S. Pat. No. 5,018,524) show an apparatus that generates a pulse train made up of bursts having the same width, where each burst is made up of a plurality of pulses of a specific frequency. The number of pulses varies from one burst to the next; the frequency of the pulses in each burst varies from one burst to the next corresponding to the variation in the number of pulses in each burst. The pulses have a frequency of 230–280 KHz; the duty cycle of the bursts is between 0.33% and 5.0%.

Liss et al. (U.S. Pat. No. 5,109,847) relates to a portable, non-invasive electronic apparatus which generates a specifically contoured constant current and current-limited waveform including a carrier frequency with at least two low-frequency modulations. The carrier frequency is between 1–100,000 KHz; square-wave or rectangular-wave modulating frequencies are 0.01–199 KHz and 0.1–100 KHz. Duty cycles may vary, but are typically 50%, 50%, and 75% for the three waveforms.

Borkan's tissue stimulator (U.S. Pat. No. 4,612,934) includes an implantable, subcutaneous receiver and implantable electrodes. The receiver can be noninvasively programmed after implantation to stimulate different electrodes or change stimulation parameters (polarity and pulse parameters) in order to achieve the desired response; the programming data is transmitted in the form of a modulated signal on a carrier wave. The programmed stimulus can be modified in response to measured physiological parameters and electrode impedance.

Hondeghem (U.S. Pat. No. 4,255,790) describes a programmable pulse generating system where the time periods and sub-intervals of the output pulses are defined by signals from a fundamental clock frequency generation circuit, plus a pair of parallel sets of frequency division circuits connected to that circuit. The time periods, sub-intervals, and output waveforms are variable.

Hsiang-Lai et al. (U.S. Pat. No. 3,946,745) provide an apparatus for generating positive and negative electric pulses for therapeutic purposes. The apparatus generates a signal consisting of successive pairs of pulses, where the pulses of each pair are of opposite polarities. The amplitude, duration, the interval between the pulses of each pair, and the interval between successive pairs of pulses are independently variable.

Brehm (U.S. Pat. No. 5,067,495) discloses a particular wave form for the purpose of alleviating chronic pain. The electrical signal is applied until the patient has a constant feeling in the chronic pain area.

McDonald (U.S. Pat. No. 3,589,370) shows an electronic muscle stimulator which produces bursts of bidirectional pulses by applying unidirectional pulses to a suitable transformer.

Landauer (U.S. Pat. No. 3,294,092) discloses an apparatus that produces electrical currents for counteracting muscle atrophy, defects due to poor nutrition, removing exudates, and minimizing the formation of adhesions. The amplitude of the output signals is variable.

All references and patents disclosed in this patent application are hereby incorporated by reference in their entirety.

Units designed for use in transcutaneous electroneural stimulation ("TENS") for pain relief are widely available. For example, Bastyr, et al. (U.S. Pat. No. 5,487,759) disclose a battery-powered device that can be used with different types of support devices that hold the electrode pads in position. Keyed connectors provide a binary code that is used to determine what type of support device is being used for impedance matching and carrier frequency adjustment. The carrier frequency is about 2.5–3.0 KHz; the therapeutic frequency is typically on the order of 2–100 Hz.

Kolen (U.S. Pat. No. 5,350,414) provides a device where the carrier pulse frequency, modulation pulse frequency, intensity, and frequency/amplitude modulation are controlled by a microprocessor. The device includes a pulse modulation scheme where the carrier frequency is matched to the electrode-tissue load at the treatment site to provide more efficient energy transfer.

Liss et al. (U.S. Pat. No. 4,784,142) discloses an electronic dental analgesia apparatus and method. The apparatus generates an output with relatively high frequency (12–20 KHz) pulses with nonsymmetrical low frequency (8–20 Hz) amplitude modulation.

Bartelt et al. (U.S. Pat. No. 5,063,929) describe a microprocessor-controlled device that generates biphasic constant-current output pulses. The stimulus intensity can be varied by the user.

Charters et al. (U.S. Pat. No. 4,938,223) provide a device with an output signal consisting of bursts of stimuli with waxing and waning amplitudes, where the amplitude of each stimulus is a fixed percentage of the amplitude of the burst. The signal is amplitude-modulated to help prevent the adaptation response in patients.

Molina-Negro et al. (U.S. Pat. No. 4,541,432) disclose an electric nerve stimulation device for pain relief The device produces a bipolar rectangular signal with a preselected repetition rate and width for a first time period. Then, a rectangular signal is generated at a pseudo-random rate for a second time period, and delivery of the signal is inhibited for a third, pseudo-random period of time. This protocol is said to substantially eliminate adaptation of nerve cells to the stimulation.

Butler et al. (U.S. Pat. No. 4,431,000) show a transcutaneous nerve stimulator for treating aphasias and other neurologically-based speech and language impairments. The device uses a pseudorandom pulse generator to produce an irregular pulse train composed of trapezoidal, monophasic pulses which mimic typical physiological wave forms (such as the brain alpha rhythm). A series of such pulses has a zero DC level; a current source in the device reduces the effects of variables such as skin resistance.

Maurer (U.S. Pat. No. 4,340,063) discloses a stimulation device which can be implanted or applied to the body surface. The amplitude of the pulse decreases with a degradation in pulse width along a curve defined by a hyperbolic strength-duration curve. This is said to result in proportionately greater recruitment of nerve fibers due to the nonlinear relationship between pulse width and threshold.

The Kosugi, et al. system (U.S. Pat. No. 4,338,945) generates pulses that fluctuate in accordance with the 1/f rule. That is, the spectral density of the fluctuation varies inversely with the frequency: pleasant stimuli often have stochastic fluctuations governed by this rule. The system produces an irregular pulse train said to promote patient comfort during the stimulation.

Signal generators are also used in hearing prostheses. For example, McDermott's receiver/stimulator (U.S. Pat. No. 4,947,844) generates a series of short spaced current pulses, with between-pulse intervals of zero current having a duration longer than that of each spaced pulse. The waveform of the stimulus current includes a series of these spaced pulses of one polarity followed by an equal number of spaced pulses of opposite polarity so that the sum of electrical charge transferred through the electrodes is approximately zero.

Alloca (U.S. Pat. No. 4,754,7590 describes a neural conduction accelerator for generating a train of "staircase-shaped" pulses whose peak negative amplitude is two-thirds of the peak positive amplitude. The accelerator design is based on Fourier analysis of nerve action potentials; the output frequency can be varied between 1–1000 Hz.

Galbraith (U.S. Pat. No. 4,592,359) describes a multi-channel implantable neural stimulator wherein each data channel is adapted to carry information in monopolar, bipolar, or analog form. The device includes charge balance switches designed to recover residual charge when the current sources are turned off (electrode damage and bone growth are said to be prevented by not passing DC current or charge).

Despite its great healing potential, traditional Western medicine has accepted electrotherapeutic treatment only grudgingly, and to date it is used only rarely. This seems to be a legacy from early beliefs that signals would need to have high local intensities to be effective. Most electrotherapeutic apparatus now available relies either on direct implantation of electrodes or entire electronic packages, or on inductive coupling through the skin using coils which generate time-varying magnetic fields, thereby inducing weak eddy currents within body tissues. The need for surgery and biocompatible materials in the one case, and excessive circuit complexity and input power in the other, has kept the price of most such apparatus (apart from TENS devices) relatively high, and has also restricted its application to highly trained personnel. There remains a need for a versatile, cost-effective apparatus that can be used to provide bioelectric stimulation in a wide range of applications, including healing acceleration and pain relief.

SUMMARY OF THE INVENTION

According to its major aspects and broadly stated, the present invention comprises an apparatus and method for generating an electrical signal for use in biomedical applications. The present invention provides devices and methods for alleviating a wide variety of health problems in both humans and animals. In contrast to prior art devices which typically utilize very high intensity signals, the present invention enables the delivery of bioelectrical stimulation wherein the electrical signal closely mirrors natural body signals. As a consequence, the receiving tissue is subject to minimal stress and healing is not only accelerated, but pain relief is also more permanent than that which takes places with other devices.

The apparatus according to the invention may be used to provide electrotherapeutic treatment for human and animal patients, including, but not limited to, healing acceleration (bone and soft tissue), relief of acute or chronic pain, and relief of swelling and/or inflammation. However, such an apparatus need not be confined to use with intact organisms, since isolated cells or tissue cultures can also be affected by electrotherapeutic waveforms (appropriate electrical stimuli have been observed to modify the rates of cell metabolism, secretion, and replication). Isolated skin cells, for example, might be treated with chosen waveforms in an appropriate medium to increase cell proliferation and differentiation in the preparation of tissue-cultured, autogenous skin-graft material. As another example, the growth of bacteria genetically engineered to produce a desirable product, such as human insulin, might be accelerated, or their secretion of the desired product increased, by treatment with a suitable waveform.

The apparatus of the present invention may be used to provide in vivo, customizable electrotherapeutic treatment for human and animal patients, including but not limited to healing acceleration, relief of acute or chronic pain, and relief of swelling and/or inflammation. Since isolated cells or tissue cultures can also be affected by electrotherapeutic waveforms (appropriate electrical stimuli have been observed to modify the rates of cell metabolism, secretion, and replication), the apparatus may also be used for in vitro applications. In contrast to TENS-type devices, which are aimed at blocking pain impulses in the nervous system, the apparatus operates at a signal level which is below the normal human threshold level of sensation and pain: most users do not experience any sensation during treatment, apart from a steady decrease in previously existing pain.

An apparatus for generating an electrical signal according to the present invention includes means for generating primary timing intervals and secondary timing intervals into which at least one primary timing interval is divided. Embodiments of this aspect may include that the primary timing intervals form a charge balanced primary cycle.

Accordingly, it is an object of the present invention to provide an apparatus and method for treating a wide variety of physiological symptoms by administering novel pulsed electrical signals to the body.

It is another object of the present invention to provide an apparatus and method for accelerating the healing of wounds.

It is another object of the present invention to provide an apparatus and method for reducing tissue swelling.

Another object of the present invention is to provide an apparatus and method for increasing angiogenesis.

It is yet another object of the present invention to provide an apparatus and method for improving the survival of skin grafts.

It is another object of the present invention to provide an apparatus and method for relieving pain.

Another object of the present invention is to provide an apparatus and method for relieving chronic or acute pain.

Yet another object of the present invention is to provide an apparatus and method for treating tendonitis.

It is another object of the present invention to provide an apparatus and method for reducing inflammation.

These and other objects, features and advantages of the present invention will become apparent after a review of the following detailed description of the disclosed embodiments and the appended claims.

DETAILED DESCRIPTION OF THE INVENTION

Figure 1:
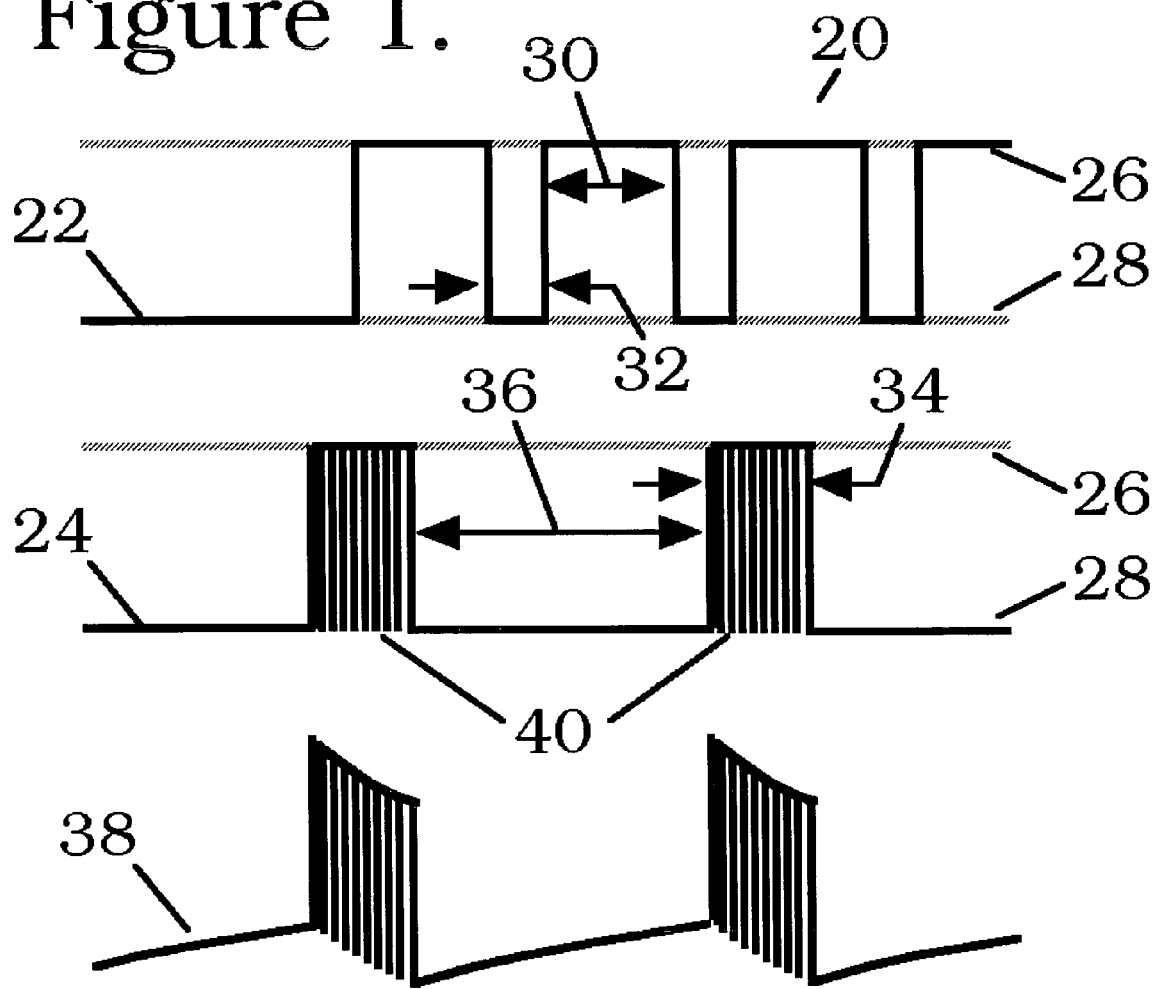
FIG. 1 is a schematic view of a waveform used in stimulating bone fracture healing. (Prior Art)

The following description includes the best presently contemplated mode of carrying out the invention. This description is made for the purpose of illustrating the general principles of the inventions and should not be taken in a limiting sense. The entire text of the references mentioned herein are hereby incorporated in their entireties by reference, including U.S. Provisional Application Ser. No. 60/480,890.

The present invention overcomes the shortcomings of prior art devices by enabling the delivery of bioelectrical signals optimized to correspond to natural body signals resulting in accelerated and more permanent healing. The signals described herein uniquely conform to natural signals and consequently tissues subjected to electrostimulation according to the present invention undergo less physiological stress when compared to electrostimulation from previous devices. In addition, the present invention is non-invasive and cost-effective making it desirable for multiple applications for personal and individual use.

According to its major aspects and broadly stated, the present invention is an apparatus and method for generating an electrical signal for use in biomedical applications. The signal includes a waveform consisting of intermittent bursts of quasi-rectangular waves (waves of generally rectangular shape but typically somewhat distorted), based on a plurality of relatively long primary timing intervals $T_1$, $T_2$ and so forth, forming in succession a primary repeating cycle; a plurality of shorter secondary timing intervals $t_1$, $t_2$ and so forth, into which at least one of said primary intervals is divided, and forming in succession a secondary repeating cycle which continues throughout the length of that primary interval, while at least one other of said primary intervals is not so divided; and a plurality of constant voltage or current levels $L_1$, $L_2$ and so forth, one of which is selected during each primary timing interval or, if that interval is divided, during each secondary timing interval within it. The series of constant current or voltage levels which are selected during successive timing intervals comprises the waveform; the average magnitude of these levels selected during a given primary interval determines the signal amplitude within that interval; and the signal amplitudes within all primary intervals, taken in succession, comprise the envelope of the waveform.

The apparatus includes a first timing block for generating primary timing intervals $T_1$, $T_2$ and so forth; a second timing block for generating secondary timing intervals $t_1$, $t_2$ and so forth; an interconnection block for combining these intervals into an output signal having predetermined relationships among the intervals; an output block for transmitting the output signal to a load (such as tissue being treated with the apparatus); a battery pack; and, optionally, a filter for removing unwanted frequency components from the output signal; and an adjustment block for chosing from among a plurality of output signals with predetermined characteristics. The first and second timing blocks may run either asynchronously or synchronously, and in the latter case, either the first timing block may be driven by the second, producing primary timing intervals $T_1$, $T_2$, $T_3$, $T_4$, and also $T_5$, and $T_6$ and so forth if present by frequency division, or both timing blocks may be driven in a like manner by a shared timing source such as a crystal-controlled oscillator.

For consistency in the following examples, but without any intent to limit the invention, $T_1$ will be considered to be the "at least one" primary timing interval which is not divided into a plurality of shorter secondary timing intervals; $L_1$ the constant level of voltage or current which is maintained during $T_1$; and $T_2$ the "at least one" primary timing interval which is so subdivided. Subsequent primary timing intervals $T_3$, $T_4$ and others if present and so forth may be so subdivided or not, as set forth in each individual example.

During each primary cycle the signal has a first amplitude level $L_1$ throughout primary interval $T_1$, then assumes a plurality of levels $L_2$, $L_3$ and so forth (which may also, optionally, include $L_1$) in succession during the secondary cycle formed by intervals $t_1$, $t_2$ and so forth into which $T_2$ is subdivided. The following primary intervals $T_3$, $T_4$ and others if present and so forth, if present, may each then either contain a secondary cycle in the manner of $T_2$, or not, in the manner of $T_1$.

As used herein, unless otherwise implied by the context, the term "select" and variations thereof are intended to refer to a range of options under circuit control. In addition, as used herein, unless otherwise implied by the context, the term "chose" and variations thereof are intended to refer to a range of options under direct human control.

Conveniently, and by analogy with early, amplitude-modulated schemes of radio transmission, the secondary cycle in such a composite waveform may be considered as a carrier wave, and the primary cycle as a signal which modulates the carrier wave with a specified, repeating envelope. By extension, where two primary intervals contain secondary cycles running at different rates, these may be considered as two different carrier frequencies.

An important feature of the invention is that its output appears as a floating, differential voltage or limited current between one pair (or, optionally, as such voltages or currents between several such pairs) of output pins or other connectors. The output signals may thus be coupled to the body through simple skin-contact electrodes, through conductive wound dressings, through conductive devices (such as metal bone fixation pins or electrically-conductive catheters) which have already been implanted for other purposes, through bodies of conductive liquid in contact with the skin or other tissues, or by similar conductive means, providing a wide range of flexibility to suit individual cases. (The term "conductive" is here taken in a broad sense including both ohmic and capacitive components, as will be explained later.)

An apparatus according to the invention is lightweight, compact, self-contained, cost-effective to manufacture and maintain, and convenient to carry or wear for extended periods. It is safe for unsupervised home use without the need for special training, and able to generate a signal as described above and deliver it efficiently to the body. Since only low voltages and currents are used, the apparatus does not pose a shock hazard even in case of malfunction power may be furnished by compact and inexpensive batteries, typically needing replacement only once in several weeks of use.

The output signal is an important feature of the present invention. The output signal is a waveform based on at least two, but optionally a greater number, of relatively long primary timing intervals $T_1$, $T_2$, $T_3$, $T_4$, and also $T_5$, and $T_6$ and so forth, forming in succession a primary repeating cycle; at least two, but optionally a greater number, of shorter secondary timing intervals $t_1$, $t_2$ and so forth, into which at least one of said primary intervals is divided, and forming in succession a secondary repeating cycle which continues throughout the length of that primary interval; and a plurality of constant voltage or current levels $L_1$, $L_2$ and so forth, one of which is presented to the output during each primary timing interval or, if that interval contains a secondary cycle, during each secondary timing interval within it. The resulting stepped waveform may then be passed through any of various types of active or passive filter in order to emphasize or attenuate chosen frequency ranges.

The primary cycle may be either periodic (automatically repeating at fixed intervals) or aperiodic (repeating only in response to some outside event). In the former case, the relative lengths of primary intervals $T_1$, $T_2$ and so forth may differ, but each is fixed in length from one primary cycle to the next. In the latter case, all primary intervals are fixed in length with the exception of $T_1$, which may be arbitrarily long.

Timing intervals $T_1$, $T_2$ and so forth, and $t_1$, $t_2$ and so forth, have the following relationships:

$$50 \ \mu sec \leq (T_1, T_2, \ldots) \leq 30 \ sec \quad (a)$$

$$200 \ \mu sec \leq (T_1+T_2+\ldots) \leq 120 \ sec \quad (b)$$

$$5 \ \mu sec \leq (t_1, t_2, \ldots) \leq 50 \ msec \quad (c)$$

$$10 \ \mu sec \leq (t_a+t_b+\ldots) \leq 0.5 \ T_A \quad (d)$$

$$(t_x, t_y, \ldots) \leq 2(t_a+t_b+\ldots) \quad (e)$$

where, if the primary cycle is periodic, $(T_1, T_2, \ldots)$ indicates any one of primary intervals $T_1$, $T_2$ and so forth; $(T_1+T_2+\ldots)$ indicates the sum of these intervals, equal to the length of a primary cycle; $(t_1, t_2, \ldots)$ indicates any one of secondary intervals $t_1$, $t_2$ and so forth; $(t_a, t_b, \ldots)$ indicate a subset of these, forming a secondary cycle within a particular primary interval $T_A$; $(t_a+t_b+\ldots)$ indicates the sum of this subset of intervals, equal to the length of the secondary cycle within $T_A$; and $t_x$ and $t_y$ indicate "stray" secondary intervals which are not intentional parts of a complete secondary cycle but may for instance, at the beginning or end of the primary cycle containing it.

In other words, each primary interval $T_1$, $T_2$ and so forth may have any length from 50 microseconds to 30 seconds, while their sum (one complete primary cycle) may have any length from 200 microseconds to 120 seconds; each secondary interval $t_1$, $t_2$ and so forth may have any length from 2.5 microseconds to 50 milliseconds, while the sum of $(t_a+t_b+\ldots)$ (one complete secondary cycle) may have any length from 5 microseconds to one-half of the primary interval during which the secondary cycle appears; and "stray" secondary intervals at the start or end of a primary interval may be present so long as their total does not exceed two secondary cycle lengths.

Where the primary cycle is aperiodic, conditions (a) and (b) are modified to $$50 \ \mu sec \leq (T_2, T_3, \ldots) \leq 30 \ sec \quad (a)$$

$$200 \ \mu sec \leq (T_2+T_3+\ldots) \leq 120 \ sec \quad (b)$$

where $(T_2, T_3, \ldots)$ indicates any one of primary intervals $T_2$, $T_3$ and so forth, and $(T_2+T_3+\ldots)$ indicates the sum of these intervals, equal to the length of a primary cycle excluding $T_1$ which, as stated above, may be arbitrarily long. All other relationships are the same as above.

Where two or more primary intervals are spent at constant output levels, these levels need not be the same, and where two or more primary intervals contain secondary cycles, the intervals and corresponding output levels within them need not be identical.

While the effect of (d) is to ensure that at least two complete secondary cycles will appear during any primary interval which contains them, in practice the number may range upward to several hundred or even a few thousand.

An effect of (e) is that one or more of the secondary intervals may be unusually long, short, or even missing during the first or last secondary cycle, or both, within a given primary interval. All secondary cycles apart from the first and the last, however, contain all of the specified intervals with each having substantially its specified length.

Most often, missing or drastically shortened intervals occur when the primary and secondary cycles run asynchronously, so that a primary transition may occur at any time within the secondary cycle and thus any primary interval $T_A$ may or may not include an integral number of secondary cycles. For example, with a secondary cycle "$t_a$, $t_b$, $t_c$, $t_d$" a primary interval $T_A$ might contain either "$t_a$, $t_b$, $t_c$, $t_d$, $t_a$, $t_b$, $t_c$, $t_d$, $t_a$, $t_b$, $t_c$, $t_d$"

(three complete secondary cycles), or

"$t_a$, $t_b$, $t_c$, $t_d$, $t_a$, $t_b$, $t_c$, $t_d$, $t_a$, $t_b$, $t_y$"

(two complete cycles, plus a third one cut off partway through, with $t_y$ representing a shortened $t_c$).

Figure 23:
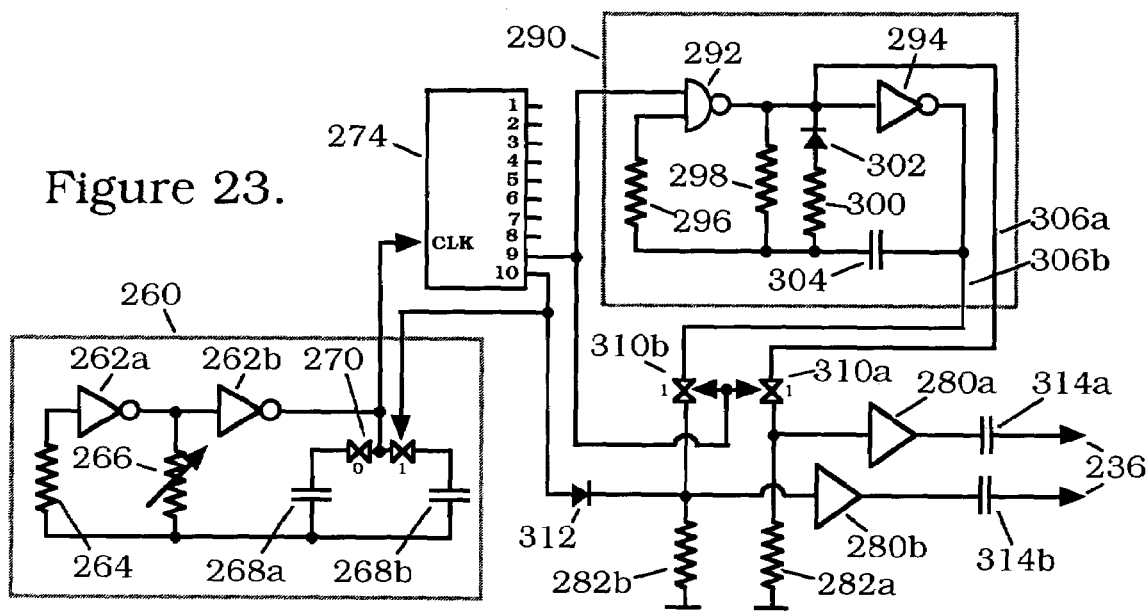
FIG. 23 illustrates a simplified circuit which, for purposes of illustration, generates a waveform similar to that in FIG. 4.
Figure 24:
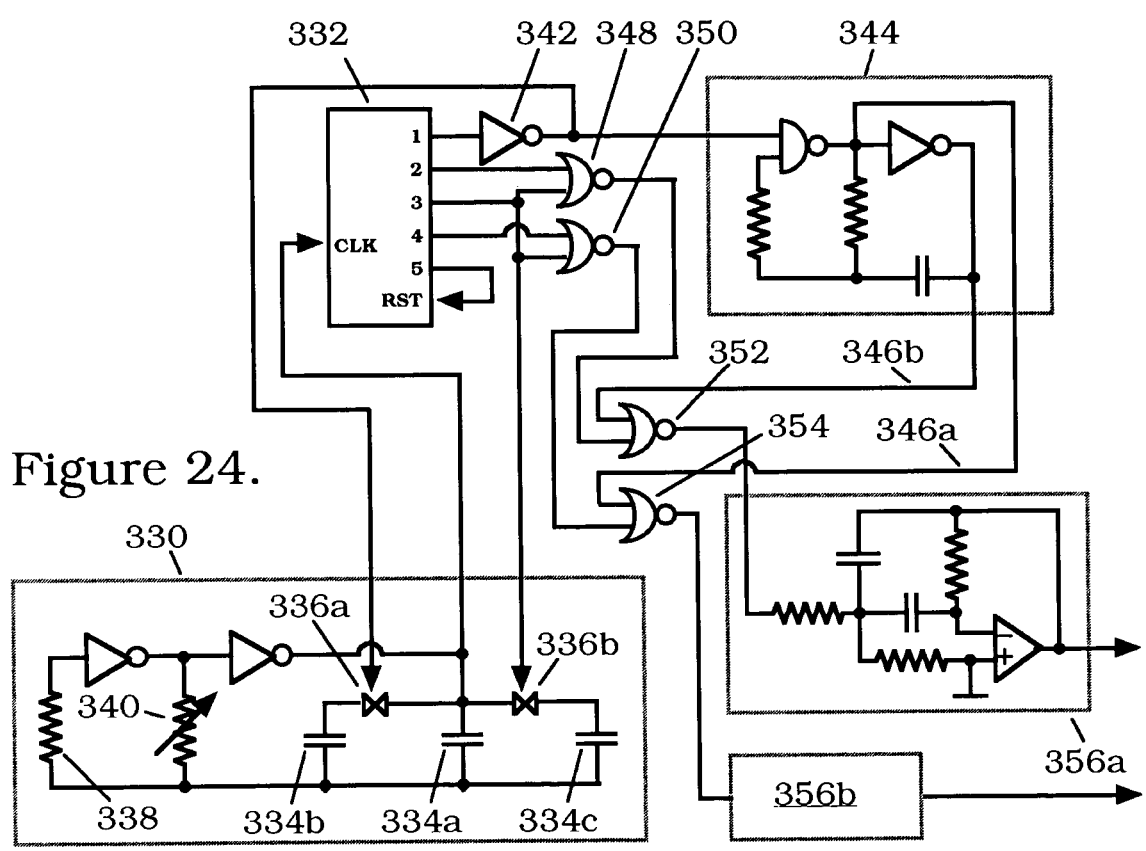
FIG. 24 illustrates a second specific embodiment of the invention, configured to generate a waveform similar to that in FIG. 6 or FIG. 16.
Figure 28:
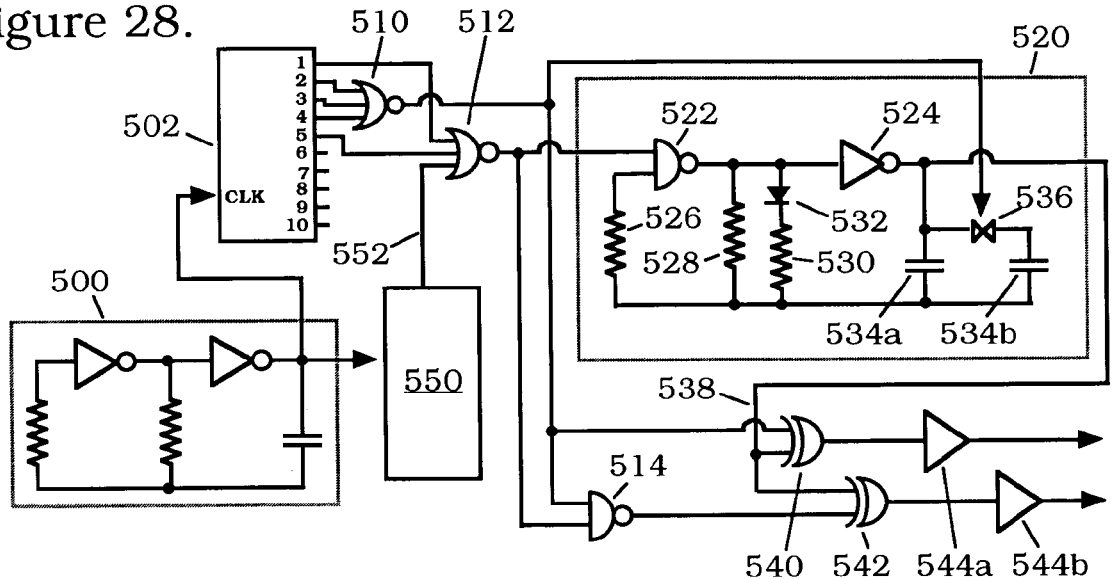
FIG. 28 illustrates a fourth specific embodiment of the invention, configured to generate a waveform similar to that in FIG. 12 but also incorporating polarity reversal.

The first secondary interval within a primary interval may also appear abnormally long or short when the secondary frequency generator is restarted after a primary interval in which it has been disabled. With a frequency generator constructed as shown in FIGS. 23, 24, and 28 such a distorted interval will typically be about one-fourth longer than normal, while with a generator constructed as in FIG. 31, it will be about one-third shorter than normal. For example, a two-stage secondary cycle might begin "$t_x, t_b, t_a, t_b, t_a, t_b \ldots$"

where $t_x$ represents a $t_a$ lengthened or shortened by startup transients.

Any such distorted intervals or portions of incomplete cycles are regarded as "strays" for the purposes of (e), and within a given primary cycle will total not more than twice the secondary cycle length.

The intervals making up any given primary cycle may all be nominally equal, or not. Preferably, however, when only two such intervals $T_A$ and $T_B$ are present, $$2T_A \leq T_B \leq 20T_A \qquad (f)$$

where either $T_A=T_1$ and $T_B=T_2$, or vice-versa. This yields an asymmetric primary cycle with a duty cycle between 66% and 95%.

Similarly, the intervals making up any given secondary cycle may all be equal, or not. Preferably, however, when only two such intervals $t_1$ and $t_2$ are present, $$2t_1 \leq t_2 \leq 20t_1. \qquad (g)$$

This yields an asymmetric secondary cycle resulting in a similarly asymmetric output waveform, again with a duty cycle between 66% and 95%.

In some cases, it may be more convenient to describe some aspects of a waveform in terms of its frequency of repetition, rather than of the time elapsed during each cycle. Accordingly, we may define $$F_P = 1/(T_1+T_2+\ldots) \qquad (h)$$

$$F_A = 1/(t_a+t_b+\ldots) \qquad (i)$$

$$F_{max} = \text{highest of } F_A, F_B, \ldots \qquad (j)$$

where $F_P$ represents the primary cycle frequency, $F_A$ represents the secondary cycle frequency within a given interval $T_A$, and $F_{max}$ represents the highest secondary cycle frequency present during any part of the primary cycle, thereby constituting the carrier frequency.

Constant voltage or current levels $L_1$, $L_2$ and so forth are typically generated first as differential voltage levels, which may thereafter be translated into levels of current. Preferably, to conserve battery power, such translation into current takes place only after the selection of a voltage level for each timing interval, so tat non-selected levels during each such timing period consume no current. More preferably, all voltages within the apparatus, including the output waveform, lie within the range between −42.4 volts and +42.4 volts, thereby meeting the IEC 950 definition of "safety ultra-low voltages". Similarly, any output currents preferably lie within the range between −10.0 milliamperes and +10.0 milliamperes, as prescribed by ANSI/AAMJ NS4-1985 for safe application to the human body.

For consistency in describing a multiplicity of different waveforms included within the scope of the invention, the following conventions will be used hereafter in labeling current or voltage levels $L_1$, $L_2$ and so forth.

$L_1$ will be the constant voltage or current level which is present throughout $T_1$. $L_1$ may be either the most positive voltage appearing at any time in the primary cycle, the most negative such voltage, or any voltage intermediate between these limits. In the latter case, $L_1$ preferably lies midway between these limits and represents zero voltage or current.

$L_2$, $L_3$, and so forth (as many as applicable) will be the levels which appear in the secondary cycle within $T_2$. Note that $L_1$ may also be present in this cycle. Levels which first appear in any following primary or secondary intervals will be numbered consecutively in the same manner. In most cases, only three levels $L_1$, $L_2$ and $L_3$ are required.

Figure 4:
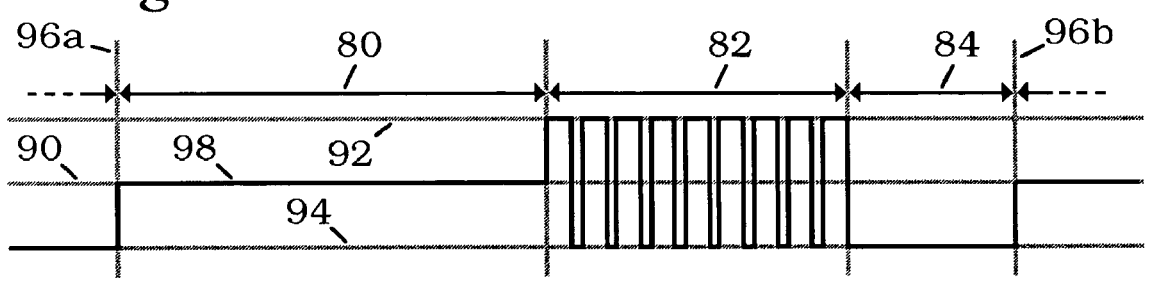
FIG. 4 illustrates a waveform according to the invention, having a carrier frequency contained within a pulsed envelope.

A basic waveform is generally described in U.S. Pat. No. 6,535,767, incorporated herein by reference, and is shown in FIG. 4. Here the waveform includes three primary intervals $T_1$, $T_2$ and $T_3$, indicated respectively by characters 80, 82 and 84, and three output levels $L_1$, $L_2$ and $L_3$, indicated respectively by characters 90, 92 and 94. A secondary cycle appears within $T_2$. The secondary intervals are not individually labeled and, for purposes of illustration, an a typically small number of secondary cycles is shown.

The flow of time is from left to right, with vertical bars 96a and 96b representing the start of $T_1$ in each of two successive cycles, so that the interval between them represents one full cycle. Solid line 98 indicates the output, which is held constant at level $L_1$ during $T_1$; undergoes a secondary cycle during $T_2$, in which it alternates between level $L_2$ during $t_1$ and $L_3$ during $t_2$; and again is held constant during $T_3$, but at $L_3$ rather than at $L_1$. At the end of $T_3$, the cycle begins again with $T_1$ and the output changes again to a constant $L_1$. Further details of this waveform, means of generating it, and some of its potential uses, may be found in U.S. Pat. No. 6,535,767.

Figure 5:
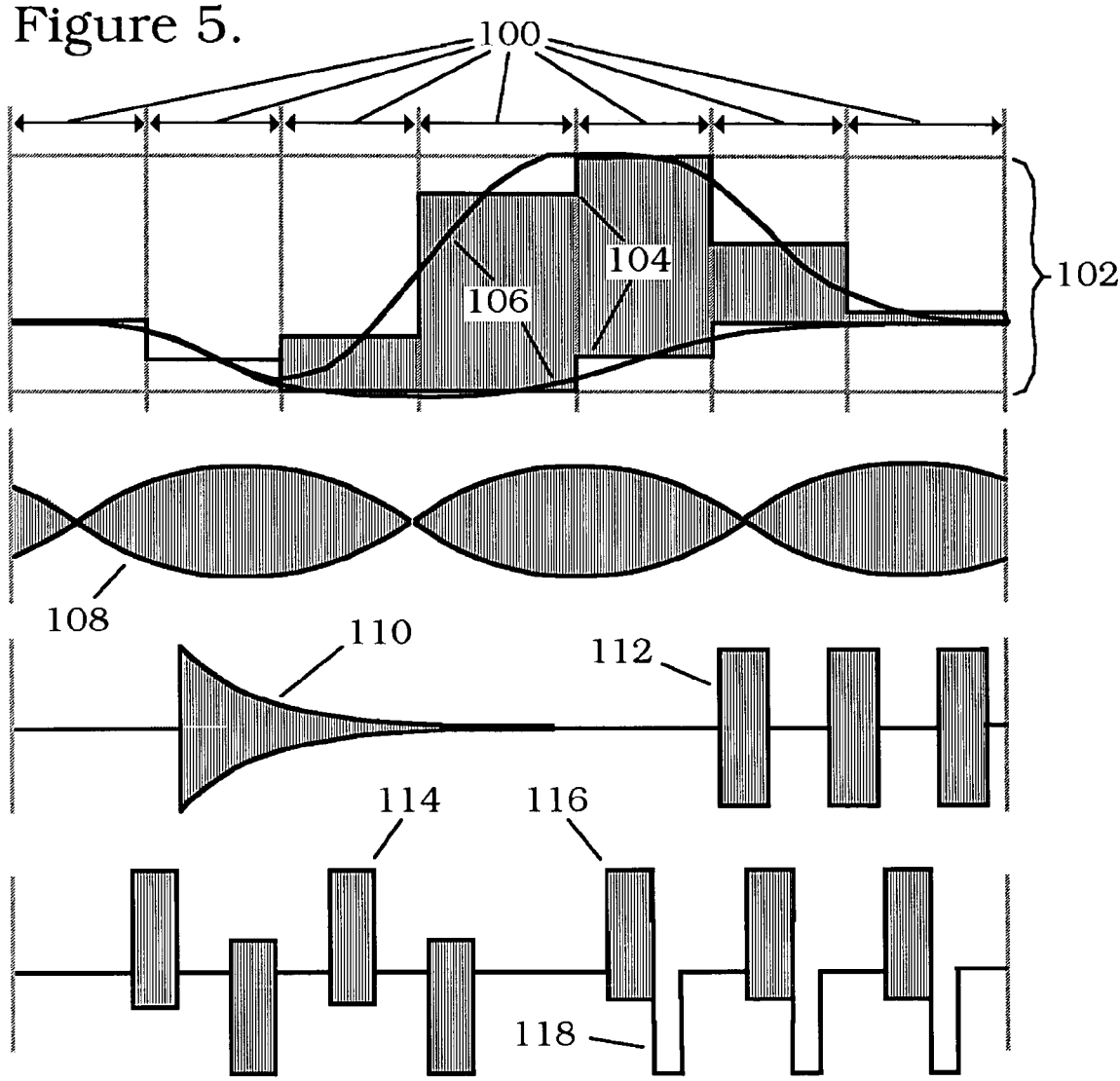
FIG. 5 illustrates a generalized waveform according to the invention, having a series of primary timing intervals and signal amplitudes contained within a stepped envelope approximating an arbitrary curvilinear function.

Broadly stated, the present invention extends this three-stage waveform to a primary cycle consisting of four or more primary tinting intervals $T_1$, $T_2$, $T_3$, $T_4$ and others if present, as generally indicated by arrows 100 in FIG. 5, fanning in succession a repeating primary cycle; at least two relatively shorter secondary timing intervals $t_1$, $t_2$ and so forth, into which at least one such primary timing interval is divided and which form in succession a repeating secondary cycle throughout its length, while at least one other primary timing interval is not so divided; a plurality of substantially constant voltage or current levels $L_1$, $L_2$ and so forth, one of which is selected during each secondary interval within a primary interval which is so divided, or during the Whole of a primary interval if it is not so divided; a resulting range of possible signal amplitude levels, generally indicated by 102; and an envelope 104 consisting of rectangular steps, one for each primary timing interval.

Each signal amplitude consists of both an A.C. (time-variant) and D.C. (time-invariant) component, indicated respectively in each step of envelope 104 by the distance between the two horizontal lines and by the midpoint between them. The D.C. amplitude is most conveniently expressed as the time average of the voltage or current within the respective primary timing interval, and the A.C. amplitude, as the root mean square (RMS) value of the instantaneous difference of the voltage or current from this average:

$$D = 1/T_A * \text{Int } (T_A)Q(t)dt$$

$$A = \text{Sqr}(1/T_A * \text{Int } (T_A)(Q(t)-D)^2 dt)$$

where D is the D.C. component, $T_A$ is a given primary timing interval, Q(t) is the voltage or current during that interval as a function of time, A is the A.C. (RMS) component, "Int($T_A$) . . . dt" represents an integral with respect to time taken throughout the length of $T_A$, and "Sqr" indicates the square root function.

A nonzero A.C. amplitude during any primary timing interval results from the presence of a secondary cycle. Vertical hatching within steps of envelope 104 is not meant to indicate any particular timing within such a secondary cycle, but merely that such a cycle is present within those steps, resulting in a nonzero A.C. amplitude.

For primary intervals which are not subdivided into secondary cycles, the voltage or current maintains a uniform value throughout, and as a result the A.C. amplitude is zero. Similarly, where the sums of the positive and negative voltage or currents are equal, they cancel each other out and the D.C. component is zero. Such a waveform is called "charge-balanced."

By proper choice of the primary timing interval lengths and of the signal amplitude within each one, envelope 104 may be caused to emulate any periodically or aperiodically repeating real-world mathematical function, as suggested by the arbitrary, curvilinear envelope 106. Examples of real-world envelopes whose emulation is within the scope of the invention are sinusoidal "interferential" envelope 108, decaying exponential envelope 110, symmetrical repeating pulse-train envelope 112, asymmetrical repeating pulse-train envelope 114 with alternate polarity reversal, and asymmetrical repeating pulse-train envelope 116 with charge-equalizing interval 118. This last example is equivalent to the waveform already shown in FIG. 4 and discussed in the accompanying text.

Another feature of the present invention is the filter, which optionally blocks frequencies above a chosen level to create a desired transition profile or to prevent interference by external high-frequency signal sources. Preferably, this level is about 10 $F_{max}$. For example, the filter may include a shunt capacitance, a resistor network, a voltage-controlled current source, or other suitable device that simultaneously slows and controls the rate of transitions, attenuates output frequency components above about 10 $F_{max}$ (or other selected frequency), and prevents interference with circuit functioning by external radio-frequency signals. Simultaneously, the filter may block D.C. components from the output, provide voltage step-up through a transformer, or both.

Yet another feature of the present invention is the use of dual timing blocks, each optionally incorporating a multi-step sequencer, to generate waveforms that can be combined to produce an output waveform having selected characteristics. In a preferred embodiment of the invention, one of the timing blocks is controlled by the sequencer and the sequencer is driven by the other timing block: that is, the output of the block which generates secondary timing intervals $t_1$, $t_2$ and so forth may be "on," "off," or have different timing characteristics, depending on the output state of the sequencer. Such different timing characteristics may be produced, for example, by incorporating a plurality of alternative component values into the second timing block, with each one switched either into or out of the circuit depending upon the sequencer outputs. This results in a circuit that generates an output signal whose characteristics—frequency, duty cycle, amplitude—can be determined over a wide range by the particular chosing of components and the way in which they are interconnected, with a surprisingly simple overall circuit configuration.

Another feature of the present invention is the use of conventional, readily-available low-voltage batteries as a safe and convenient power source for the apparatus. While the invention may be used with AC (alternating current) power sources (with the addition of any suitable adapter), battery power is preferred since it not only reduces the size and weight of the apparatus, but also adds to its safety and ease of use for a patient undergoing treatment. Typically, the batteries need to be replaced at infrequent intervals (generally no more than once every few weeks, depending on the output signal and the particular application), simplifying patient compliance and reducing operating costs. Only low power levels, such as are required to produce therapeutic effects, are applied to the body. Thus, the invention cannot produce an electrical shock hazard even in the event of a malfunction, and is therefore suitable for unsupervised home use.

Figure 3:
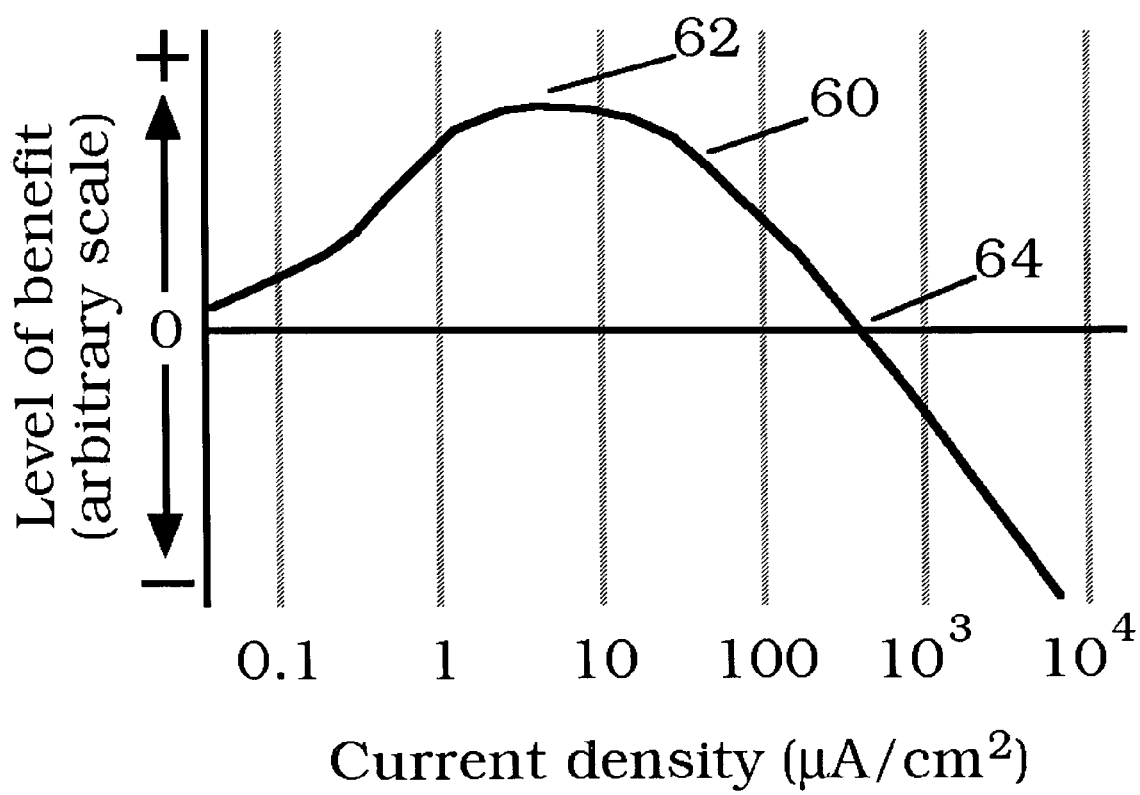
FIG. 3 is a schematic view of healing effect vs. signal intensity (amplitude). (Prior Art)

Still another feature of the present invention is its versatility. The apparatus may be configured easily so as to produce an output waveform with choosable timing intervals, output voltage or current levels, and overall envelope, or to allow choice among a plurality of any of these, to address various physiological needs. As noted above, tissues may respond in different ways to different signal frequencies, to a pure AC signal, or to an AC signal with a superimposed positive or negative DC component. Similarly, as shown in FIG. 3, different effects may appear at different current densities.

An apparatus with an adjustable output signal is useful for a greater variety of applications than one having a fixed output. On the other hand, medical professionals may prefer a generator having a fixed output, or an output that is adjustable only in magnitude, for outpatient use by their patients. Embodiments of the invention are described in which the user can adjust the frequency of a signal for a given application by turning a rotary switch or other means to chose one of a plurality of the available signals noted above, while other described embodiments are not so adjustable.

Yet another feature of the invention is its versatility in means of application. Signals generated by the circuitry of the invention are easily applied to the human or animal body, to living tissue or cell cultures, or to foodstuffs or pharmaceutical materials, by a variety of different, either invasive or noninvasive, electrically-conductive means.

In the following description of best modes for carrying out the invention, reference numerals are used to identify structural elements, portions of elements, surfaces or areas in the drawings, as such elements, portions, surfaces or areas may be further described or explained by the entire written specification. For consistency, whenever the same numeral is used in different drawings, it indicates the same element, portion, surface or area as when first used. Unless otherwise indicated, the drawings are intended to be read together with the specification, and are to be considered a portion of the entire written description of this invention as required by 35 U.S.C. § 112. As used herein, the terms "horizontal," "vertical," "left," "right," "up," "down," as well as adjectival and adverbial derivatives thereof, refer to the relative orientation of the illustrated structure as the particular drawing figure faces the reader.

The present invention is an apparatus for use in providing bioelectric stimulation in a variety of applications, together with a method for its application to the human body or to other living or nonliving materials.

As previously stated, the objective of the invention is to generate any one or any combination of a broad class of waveforms, for use in biomedical applications, each of which is based on a plurality of relatively long primary timing intervals $T_1$, $T_2$ and so forth, forming in succession a primary repeating cycle; a plurality of shorter secondary timing intervals $t_1$, $t_2$ and so forth, into which at least one of said primary intervals is divided, and forming in succession a secondary repeating cycle which continues throughout the length of that primary interval, while at least one other of said primary intervals is not so divided; and a plurality of constant voltage or current levels $L_1$, $L_2$ and so forth, one of which is presented to the output during each primary timing interval or, if that interval contains a secondary cycle, during each secondary timing interval within it. At least two, and typically several hundred, secondary cycles occur during each such primary interval. The resulting stepped waveform may then be passed through any of various types of active or passive filter in order to emphasize or attenuate chosen frequency ranges.

As was previously shown in FIG. 5, by following the principles of the present invention, a waveform having an envelope consisting of a sufficient number of rectangular steps can be tailored to approximate virtually any curvilinear function. Many such functions are characteristic of real-world applications. Typical examples of such real-world functions are the sinusoidal envelope which is produced when two sine waves at similar frequencies and amplitudes interfere, alternately reinforcing each other and canceling each other out; and the exponential envelope which is produced when an oscillatory system, such as a plucked harp string, radiates away energy progressively so that the amplitude of its oscillations decreases smoothly over time. Others will be obvious to anyone well-versed in the art of signal generation, processing or transmission.

A waveform of approximately sinusoidal envelope, according to the principles of the invention, is of interest in electrotherapy since it approximates the sinusoidal energy distribution over time which is a primary feature of traditional interferential electrotherapy. In such therapy, two sinusoidal signals of slightly different frequencies are applied to the body and allowed to "interfere" within it, creating a lower "beat frequency" upon which a higher "carrier" frequency is modulated. The carrier frequency is simply the average of the two original frequencies, while the beat frequency is the difference between them. Carrier frequencies typically range from about 1000 to about 10,000 Hz, with frequencies between 4000 and 4500 Hz most common although for some applications higher frequencies, up to approximately 200 KHz, may be preferable. Beat frequencies differ widely for various conditions, but typically lie in the range from 1 Hz to 500 Hz.

A first approximately sinusoidal waveform, following the principles of the invention, consists of five primary timing intervals $T_1$–$T_5$, of which $T_1$ and $T_5$ are spent at constant output levels $L_1$ and $L_3$ respectively, $T_5$ thereby serving as an equalizing pulse, while $T_2$, $T_3$ and $T_4$ all contain secondary cycles. Where charge balance is established by other means, an equalizing pulse may not be needed and in such a case, $T_5$ may be omitted.

The secondary cycles within $T_2$ and $T_4$ are alike in timing and A.C. amplitude, while that in $T_3$ has a higher A.C. amplitude than those in $T_2$. Preferably, the A.C. amplitude within $T_3$ is about twice that in $T_2$ or $T_4$. More preferably, $T_2$ and $T_4$ are each shorter than $T_3$. Most preferably, $T_2$ and $T_4$ are each about twice the combined length of $T_1$ and $T_5$, while $T_3$ is about three times the combined length of $T_1$ and $T_5$. An advantage of this specific combination of timing intervals is that it approximates the sinusoidal envelope with minimum numbers of primary intervals and of discrete voltage or current levels, thus permitting great potential circuit simplicity and efficiency.

Figure 6:
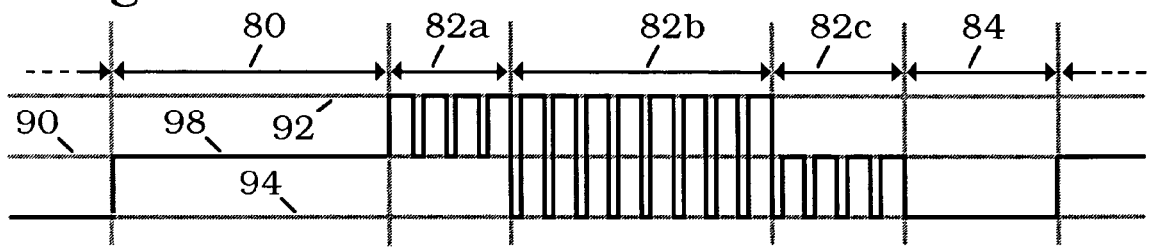
FIG. 6 illustrates a waveform according to the invention, having a carrier frequency contained within an approximately sinusoidal envelope.

A representative example of this five-stage (or four-stage, if $T_5$ is omitted), quasi-sinusoidal or "interferential-like" waveform, using only three voltage or current levels L1, L2 and L3, is shown in FIG. 6. The repetition rate of the primary cycle represents the beat frequency, while the repetition rate of the secondary cycle represents the carrier frequency. Amplitude reduction during $T_2$ (82*a*) and $T_4$ (82*c*), relative to $T_3$ (82*b*), is achieved by keeping the same timing, but switching between more closely-spaced voltage or current levels. To illustrate one of many possible variations in the waveform, the secondary cycle within T4 is shown with a different D.C. offset from that in T2.

FIG. 6 and all others following it which depict waveforms (FIGS. 7 through 16, 25, 27, 29, 30, 32 and 34) follow the same conventions which were used in FIG. 4, but with the following simplifications:

(1) A single primary cycle is shown in each Figure, beginning with $T_1$ at the left margin of the figure, and ending at the right margin.

(2) Dashed lines indicating $L_1$, $L_2$ and so forth are omitted except where cited in the text, since these levels are clearly shown by the flat tops and bottoms of the pulses in each Figure.

(3) Identifying characters are omitted except where they are specifically cited in the text.

Since in a few cases the differences between waveforms in successive primary intervals $T_1$, $T_2$ and so forth are subtle and may not be immediately obvious, the vertical hatched lines indicating the divisions between these intervals appear in all Figures. Divisions within a secondary cycle are not indicated, since in each case they should be obvious from the shape of the waveform itself.

Typically, where a voltage or waveform trace represents the signal on a line or at the output of a logic gate previously shown in a schematic diagram, the voltage or waveform trace will be given the same identifying character as the line or gate. Multiple traces, corresponding to different circuit conditions affecting the signal at the same location, will be identified with the same character followed by "a," "b" and so forth. In the text, the mention of "voltage X," "signal X" or the like indicates the voltage or signal corresponding to a trace "X" on a waveform diagram, or to a signal line or logic-gate output "X" in a schematic diagram, where "X" represents a common identifying character shared by all.

Figure 7:
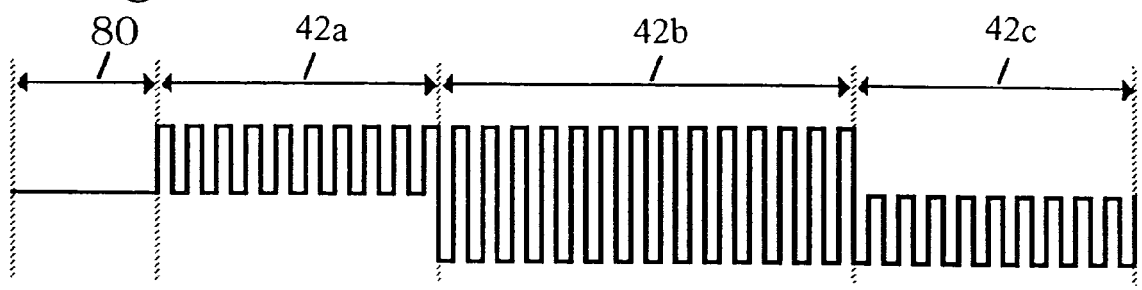
FIGS. 7–9 illustrate waveforms according to the invention, also having carrier frequencies contained within approximately sinusoidal envelopes, but demonstrating alternative modulation schemes.

Another representative, quasi-sinusoidal waveform is shown in FIG. 7 containing four primary timing intervals 80, 42*a*, 42*b* and 42*c*. This differs from the example in FIG. 6 in that the lower-amplitude or "step-in" and "step-out" periods 42*a* and 42*c*, corresponding to intervals 82*a* and 82*c* in FIG. 6, now each exceed in length the "quiet" or "no-signal" period corresponding to interval 80. Preferably, the "quiet," "step-in," "full signal" and "step-out" periods have durations in the ratio 1:2:3:2. The result is a ratio of peak to average voltage or current (1.60) which closely approximates that of a mathematically pure sinusoid (1.57), and a ratio of peak to R.M.S. voltage or current (1.414) which is identical with the pure sinusoid's. Because of the waveform's symmetry, no equalizing pulse is needed.

Figure 8:
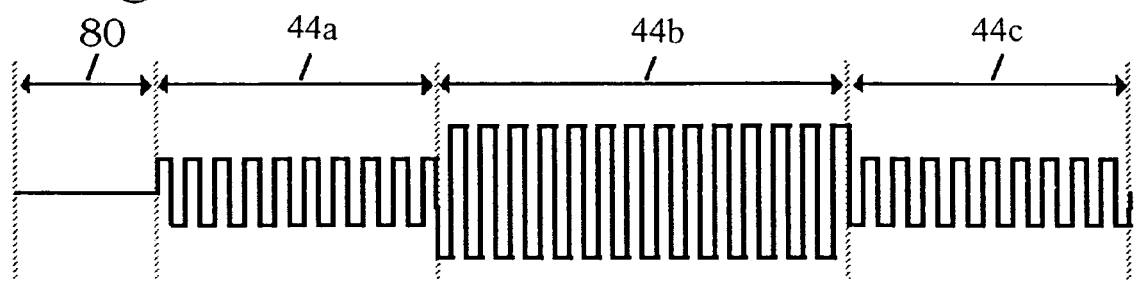

Yet another representative four-stage, quasi-sinusoidal waveform is shown in FIG. 8 and contains four primary timing intervals 80, 44*a*, 44*b* and 44*c*. This differs from the previous examples in that the higher average amplitude during $T_3$ (44*b*) is achieved by switching between additional, higher voltage or current levels than those used in $T_2$ (44*a*) and $T_4$ (44*c*).

Figure 9:
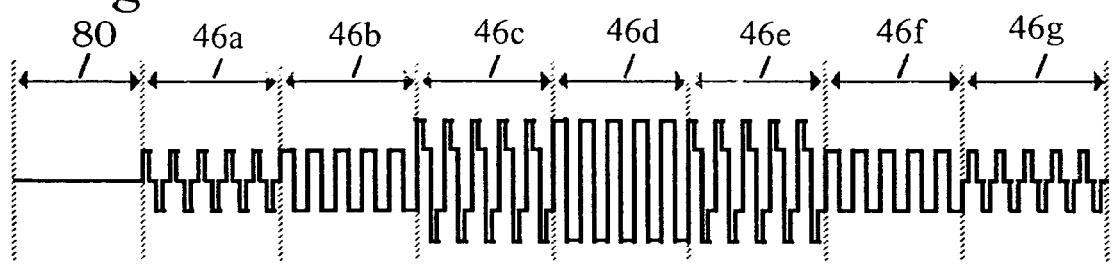

Additional waveforms according to the invention may contain any integral number of primary intervals, and within each of them (except for the first) a secondary cycle containing any integral number of secondary intervals. For example, a more accurate emulation of sinusoidal energy distribution over time might be achieved using a larger number of primary timing intervals: either by selecting from among more than three constant voltage or current levels, by using varying duty cycles within the secondary cycles, or by a combination of these approaches, as shown in FIG. 9 which contains eight primary timing intervals 80 and 46*a* to 46*g*.

In general, such a waveform consists of an even number P of primary timing intervals $T_1$, $T_2$, $T_3$ and so forth, an even number S of secondary timing intervals $t_1$, $t_2$, $t_3$ and so forth, and an odd number Q of voltage or current levels $L_1$, $L_2$, $L_3$ and so forth.

Voltage or current level $L_1$ approximates zero voltage or current, while the remaining levels $L_2$, $L_3$ and so forth form pairs, each pair having roughly equal magnitudes but opposite polarities. The members of such a pair may be represented by $L_X$ and $L_Y$, respectively. There may either be one such pair, as shown in FIGS. 6 and 7, or more than one pair, as shown in FIGS. 8 and 9. The use of a more widely-spaced pair yields a greater signal amplitude.

S may be any even integer, but is preferably four, yielding secondary timing intervals $t_1$, $t_2$, $t_3$ and $t_4$. Intervals $t_1$ and $t_3$ are preferably equal, as are $t_2$ and $t_4$, but the value of $t_1$ and $t_3$ need not be the same as that of $t_2$ and $t_4$. A non-zero level $L_X$ is selected during $t_1$, its paired $L_Y$ is selected during $t_3$, while $L_1$ is selected during $t_2$ and $t_4$. This causes the four intervals to form a duty cycle, $$DC=(t_1+t_3)/(t_1+t_2+t_3+t_4),$$

which may have any value from zero to 100%. An increase in the duty cycle yields a greater signal amplitude. At DC=0, $t_1$ and $t_3$ vanish and the signal becomes a constant $L_1$, while at DC=100%, $t_2$ and $t_4$ vanish and the signal becomes a square wave alternating between $L_X$ and $L_Y$.

Alternatively, to attain a higher signal intensity it may be found preferable to have the members of one symmetrical level pair $L_X$ and $L_Y$ selected during $t_1$ and $t_3$, and the members of another such pair $L_{X'}$ and $L_{Y'}$ selected during $t_2$ and $t_4$. This again causes the four intervals to form a duty cycle ranging from zero to 100%, although now a duty cycle of zero represents a square wave alternating between $L_{X'}$ and $L_{Y'}$, while as before, a 100% duty cycle represents one alternating between $L_X$ and $L_Y$. Again, and here assuming that the magnitude of $L_X$ and $L_Y$ is greater than that of $L_{X'}$ and $L_{Y'}$, an increase in the duty cycle yields greater signal amplitude.

For primary timing intervals $T_1$, $T_2$, $T_3$ and so forth, there will be one unique level $T_N$, where N=(P/2)+1, at which the signal amplitude is at its maximum. The amplitude will then be less for $T_{N+1}$ and $T_{N-1}$, still less for $T_{N+2}$ and $T_{N-2}$, and so forth, until for $T_2$ and $T_P$ is relatively small, and for $T_1$ it is zero since a constant $L_1$ is selected. Signal amplitudes may be selected by changing the combination of signal levels $L_1$, $L_2$ and so forth which alternate during the secondary cycle, by changing the duty cycle of their alternation, or by a combination of these means, while both timing intervals and signal amplitudes are chosen to approximate a sinusoidal envelope, as shown in FIG. 9.

The examples given above should not be interpreted as restricting the scope of the invention to signals of quasi-sinusoidal form, since it is an object of the invention to provide a maximum range of possible output signals, achievable by like means and using like circuitry, but not all necessarily having similar envelopes.

One example of a non-sinusoidal envelope is shown in FIG. 4.

Figure 10:
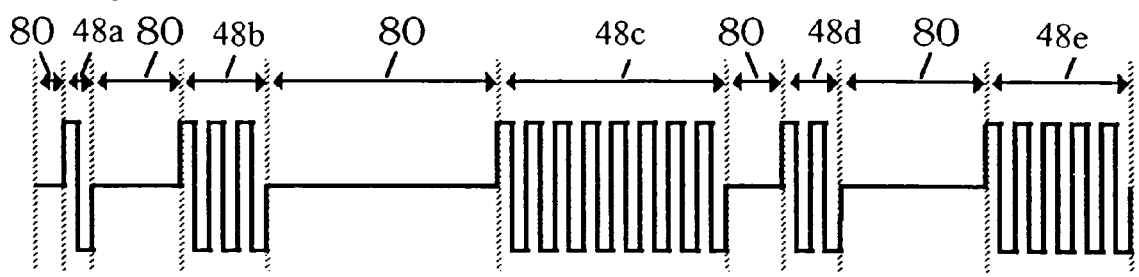
FIG. 10 illustrates a waveform according to the invention, having a carrier frequency contained within an irregularly pulsed envelope.

Another class of such non-sinusoidal signals might find use in muscle stimulation or re-education, in which trains of short, high-intensity pulses must alternate with rest periods, causing alternate contraction and relaxation of the muscle fibers. It is well-known that different muscle fibers, and the nerves supplying them, have different response thresholds and thus respond best to impulses or bursts with different energies. A waveform whose primary cycle includes several different burst lengths, with similarly varied intervals between them, may thus be more effective than one with only a single burst length and interval. FIG. 10 shows an example of such a waveform, employing ten primary intervals 48*a* to 48*e* each with a no-signal interval 80 prior to it of which five contain identical secondary cycles but vary in length.

Figure 11:
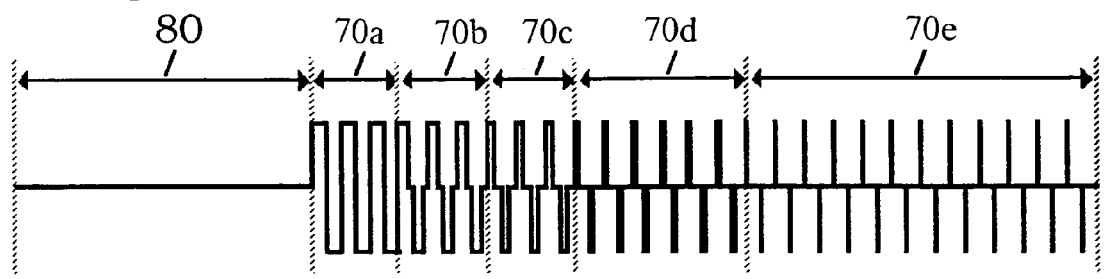
FIG. 11 illustrates a waveform according to the invention, having a carrier frequency contained within an envelope which approximates exponential decay.

Another example of a non-sinusoidal signal, as previously mentioned, is a pulsed signal which rises quickly to a maximum intensity, then decays in a linear, exponential or other fashion with time. A six-stage waveform approximating such an exponential decay characteristic, using variable timing intervals within the secondary cycle to achieve the intensity variation, is shown in FIG. 11 and contains six primary timing intervals (80 and 70*a* to 70*e*). The signal may be either periodic (automatically repeating) or aperiodic (occurring only when triggered by some external event, such as the press of a button). For example, in a materials processing application, the primary cycle might be initiated at the moment when electrodes make adequate contact with a body of food, beverage or pharmaceutical material to be treated. Where the signal is aperiodic, T1 may be arbitrarily long. This will be explained further in the text accompanying FIG. 29. Yet another example of a non-sinusoidal signal is the one shown in FIG. 12 containing six primary timing intervals (80, 72*a*, 72*b*, 80, 72*c* and 72*d*). This is simply a doubled version of the waveform which was shown in FIG. 4, except that $T_2$ (72*a*) and $T_5$ (72*c*) now contain different secondary cycles representing different carrier frequencies. A waveform of this type might be used in pain relief by alternately stimulating two known, pain-relieving biochemical channels which respond optimally at different frequencies. Specifically, stimulation around 2 to 4 Hz has been shown to produce long-lasting analgesia, but with a slow onset; stimulation around 100 to 200 Hz produces short-acting analgesia with a fast onset; while an alternation of both types of stimulation, each lasting for several seconds, activates both mechanisms so that the analgesia has a fast onset but long duration.

A waveform of the general type described above and according to the principles of the present invention will inherently be charge-balanced—that is, the output will show a net zero direct-current content—if the time average of positive and negative voltages or currents at the output, over the length of one primary cycle, is zero. This may be achieved in any of several ways. For example, the output may be passed through an output network which blocks direct current. Alternatively, the positive and negative signal intervals may be balanced so that approximately equal amounts of time are spent in each state, minimizing the direct-current content. These approaches may also be combined. For instance, in the device described in U.S. Pat. No. 6,535,767 for producing the waveform of FIG. 4, the constant level $L_3$ presented to the output during $T_3$ partly compensates for the net non-zero output caused by the asymmetry of the secondary cycle during $T_2$, while any remaining imbalance is handled by direct-current-blocking series capacitors in an output filter.

In other applications, for instance in iontophoresis (the transport of bioactive ions, such as silver ions or protonated alkaloids, through the skin or other tissues) or in the acceleration of wound healing through cell galvanotaxis, it is desirable to introduce a controlled direct-current content superimposed on the principal, alternating-current waveform. This may be done simply by unbalancing the time spent in positive and negative intervals, so that one polarity predominates, while eliminating any downstream components, such as series capacitors, which would block the desired direct-current signal content.

Figure 13:
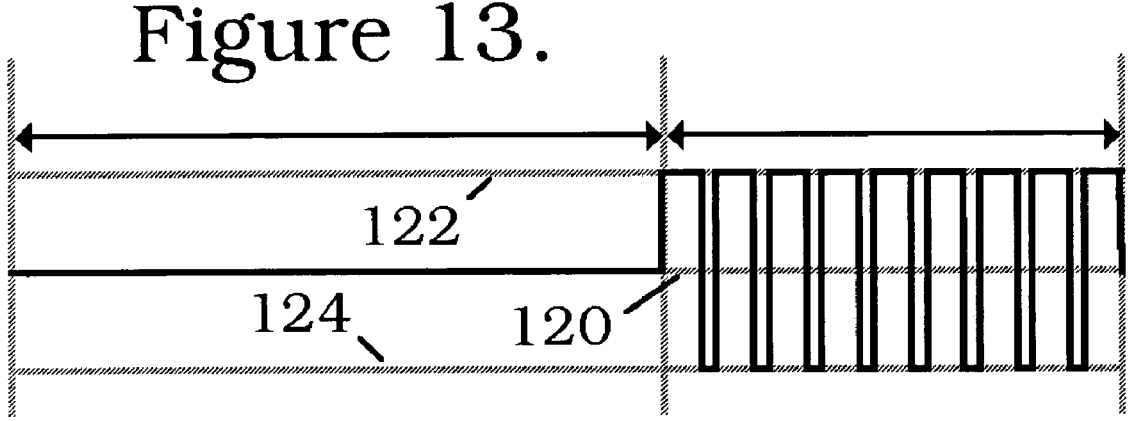
FIG. 13 illustrates a simplified version of the waveform in FIG. 4.

Such a deliberately unbalanced waveform is shown in FIG. 13, in which 120 represents a level $L_1$ of zero voltage or current, 122 a positive level $L_2$, and 124 an equal and opposite negative level $L_3$. The difference between $t_1$ and $t_2$ during $T_2$ introduces the desired charge imbalance. Note that this is simply the waveform which was previously shown in FIG. 4, but here with its charge-balancing interval $T_3$ removed.

Figure 14:
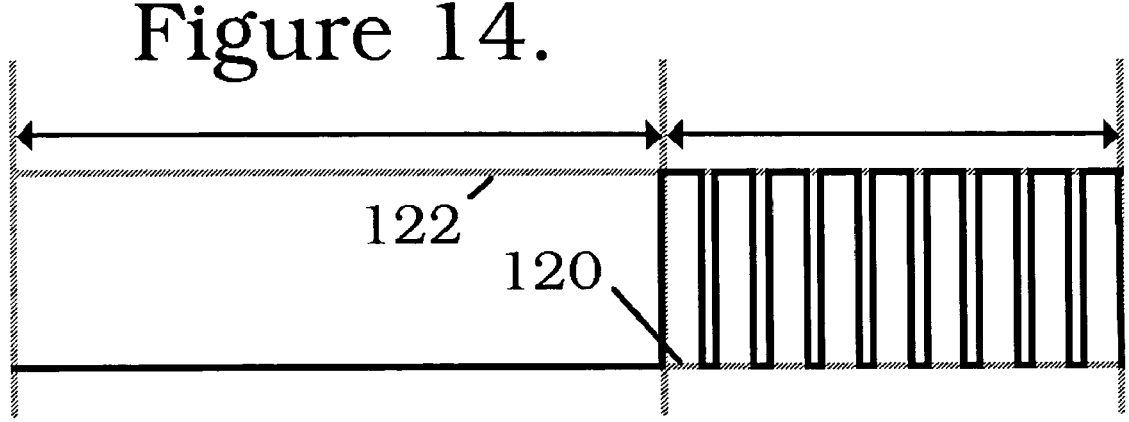
FIG. 14 illustrates a still more simplified version of the same waveform.

Alternatively, the waveform may be deliberately unbalanced by making the polarities asymmetrical around zero: most simply, by eliminating all levels of a given polarity (positive or negative) as shown in FIG. 14, where as before 120 represents a level $L_1$ of zero voltage or current, 122 a positive level $L_2$, but there is now no negative level $L_3$.

Figure 15:
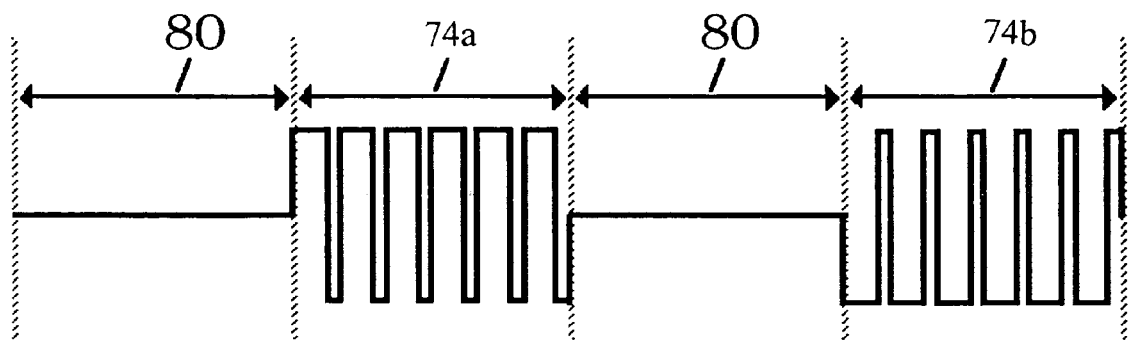
FIG. 15 illustrates a waveform built up from successive pulses like that in FIG. 13, but with alternating polarities.

In still other applications, such as in accelerating nerve regeneration, it may be found advantageous to apply a signal which is charge-unbalanced over chosen parts of a relatively long primary cycle, but charge-balanced over the cycle as a whole. FIG. 15 illustrates such a primary cycle, in which $T_1$ (80) and $T_3$ (80) represent intervals of zero voltage or current while $T_2$ (74a) and $T_4$ (74b) are intervals of charge-unbalanced signals. $T_2$ (74a) and $T_4$ (74b) are equal in length, and equal and opposite in polarity, so that over the full primary cycle the charge remains balanced. For optimal nerve regrowth, for example, $T_2$ (74a) and $T_4$ (74b) are each preferably between 10 and 60 minutes in length, while $T_1$ (80) and $T_3$ (80) may each be substantially shorter.

Many additional waveforms, following the principles of the invention, should now be apparent to anyone skilled in the arts of circuit design or waveform analysis.

Figure 16:
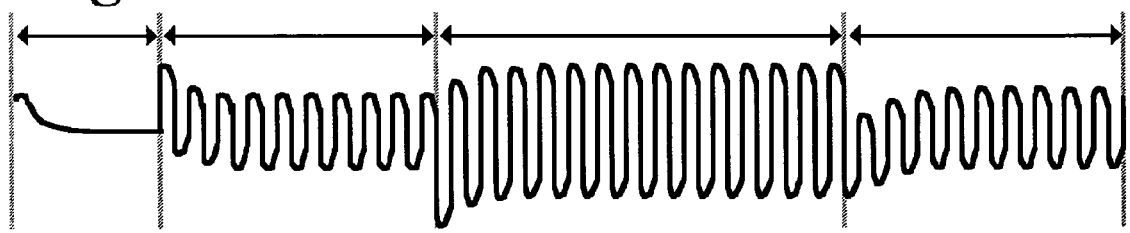
FIG. 16 illustrates a waveform representing that in FIG. 6 after a typical combination of low-pass filtering and D.C. blocking.

Any such waveform, once it has been generated in the form of a stepped voltage or current as described, may then optionally be passed through a network of active or passive components, such as a resistor-capacitor network or operational-amplifier bandpass filter to attenuate selected frequency components, a transformer (with suitable driving circuitry) to step up the output voltage or provide isolation against possible leakage currents, or series capacitors to block direct current from the output. FIG. 16, for instance, represents the waveform of FIG. 7 after passage through a filter designed to block both direct current and frequency components higher than a few times $F_{max}$.

For any waveform such as those described above, it may be found desirable to vary one or more parameters, such as primary intervals $T_1$, $T_2$ and so forth, secondary intervals $t_1$, $t_2$ and so forth, or voltage/current levels $L_1$, $L_2$ and so forth, either during treatment or between successive treatments. For example, in interferential stimulation, $t_1$, $t_2$ and so forth may be adjusted, preferably together so that the ratio between them is preserved, creating different carrier frequencies to compensate for variable user skin impedance, while $T_1$, $T_2$ and so forth may be adjusted, again preferably together, to change the effective beat frequency thus activating different tissue repair processes. Similarly, the spans between the applied voltages or currents $L_1$, $L_2$ and so forth may be varied so as to compensate for variable tissue cross-sections under treatment or differing optimal current densities of various tissues.

Conditions believed to be treatable with waveforms such as those described above include, but are not necessarily limited to, the following: bone fractures, osteoporosis, acute pain, chronic pain, swelling, simple inflammation, and inflammatory disorders such as tendonitis (including carpal tunnel syndrome and other repetitive stress injuries) and osteoarthritis. Accelerated healing of wounds, involving a variety of tissue types and resulting either from trauma or from degenerative conditions such as diabetes, may also be seen during treatment. However, it should be understood that no one set of timing intervals and voltage or current levels are useful for treating all (or even most) of these conditions.

While not wishing to be bound by theory, it is believed that appropriate voltage/current levels and timing intervals may be used to treat a wider variety of conditions whose etiology involves improper rates or imbalances in cell metabolism, secretion or replication, or which can be relieved by suitably modifying these factors. Thus, it should be understood that the optimum waveform characteristics for each particular application are best found with a modest combination of observation and experimentation.

The primary intent of the invention, as here described, is to provide electrotherapeutic treatment for human and animal patients, including but not limited to healing acceleration, relief of acute or chronic pain, and relief of swelling and/or inflammation. However, the apparatus need not be confined to use with intact organisms, since isolated cells or tissue cultures can also be affected by electrotherapeutic waveforms; appropriate electrical stimuli have been observed to modify the rates of cell metabolism, secretion, and replication. Isolated skin cells, for example, might be treated with chosen waveforms in an appropriate medium to increase cell proliferation and differentiation in the preparation of tissue-cultured, autogenous skin-graft material. As another example, the growth of bacteria genetically engineered to produce a desirable product, such as human insulin, might be accelerated, or their secretion of the desired product increased, by treatment with a suitable waveform. As yet another example, the viability of chosen organisms within a food product, beverage, drinking water or a pharmaceutical product might be decreased by similar treatment, again using a waveform chosen for the purpose.

The means of application is another important feature of the invention. The broad range of achievable therapeutic signal waveforms, frequencies and strengths suits the invention to a broad range of such application means, including, but not necessarily limited to: conductive skin-contact electrodes; conductive wound dressings, such as hydrogels or saline-soaked gauze; conductive liquids, such as saline baths in which the body or any parts of it may be immersed; conductive materials, such as bone-fixation pins or catheters, which may have been inserted into or implanted in the body for other purposes; and conductive materials of like nature placed in contact with cell or tissue cultures, foodstuffs, drinking water and other beverages, or pharmaceutical materials.

"Conductive" as used in the preceding paragraph may refer to any one or combination of the following phenomena: metallic conduction; semiconductor-type conduction by either positive or negative charge carriers; primarily tunneling conduction, such as takes place in some carbon-filled plastics; ionic conduction, for example by the motion of ions in salt water or another, typically aqueous solution; electrolytic conduction, in which ions are oxidized or reduced at an interface, for example that between a metallic conductor and an ionic solution; and capacitive conduction, in which charge is transferred by displacement currents, for example through a thin sheet of insulating material, upon changes in the applied voltage.

Figure 17:
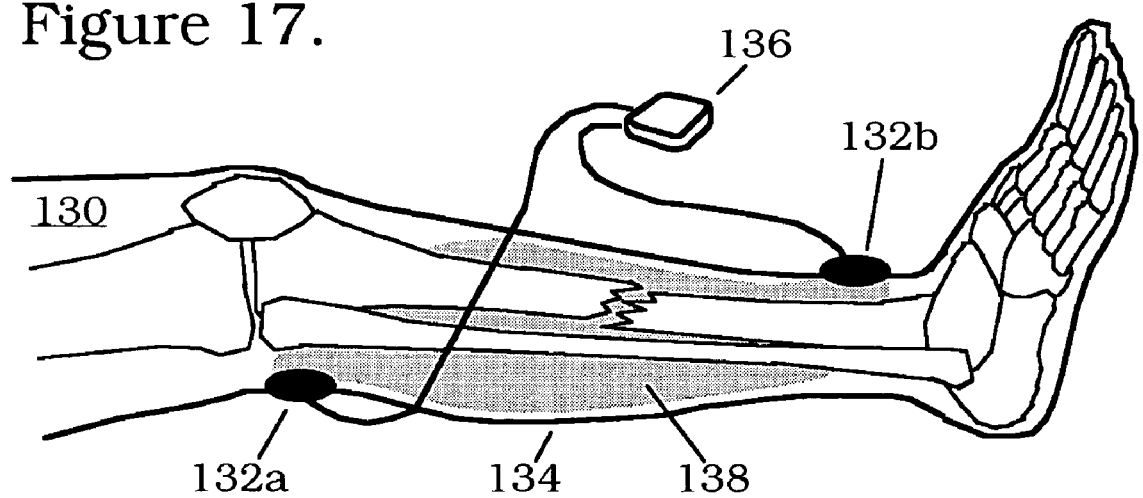
FIG. 17 illustrates a method for applying waveforms, such as those shown in the preceding Figures, to the human body or a portion thereof, using conductive electrodes.

FIG. 17 illustrates a mode of use of the invention in which a stimulating signal is applied through a volume of body tissue 130 by means of conventional skin-contact electrodes 132a and 132b, such as those used in TENS (transcutaneous electric nerve stimulation). TENS electrodes are inexpensive, widely available in a variety of shapes and styles, and usually self-adhesive. For use with the invention, they are placed on the skin 134 and driven by a signal source 136 in such a way that the current flowing between them includes the tissue volume to be treated.

As a general rule, the current will distribute itself primarily within a roughly football-shaped volume 138, lying within tissue volume 130 with one of its ends at each electrode. Tissues within volume 138 will therefore receive the most effective treatment. For example, in the treatment of a bone fracture, the electrodes should be positioned on the skin so as to place the fracture near the center of this volume, as shown.

Figure 18:
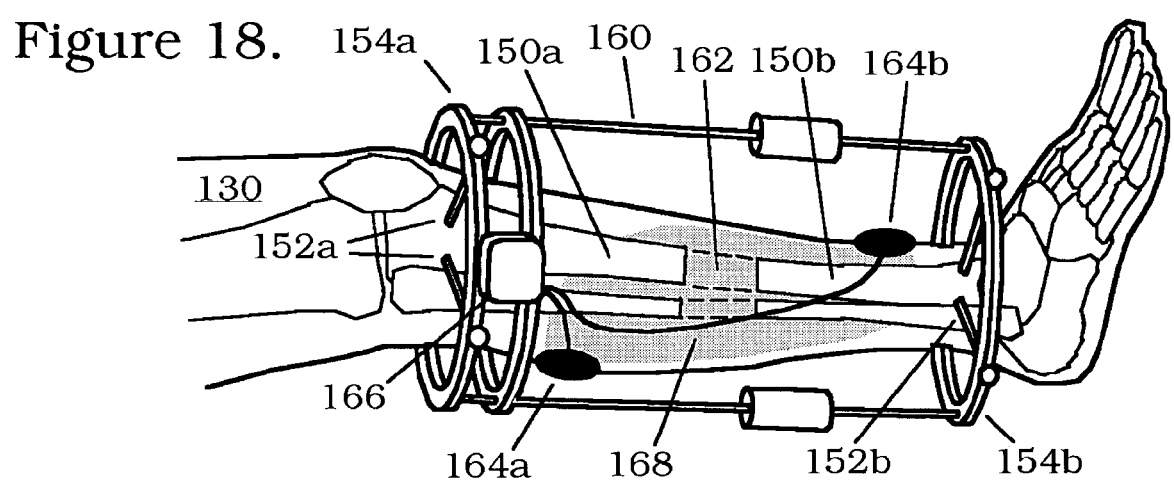
FIG. 18 illustrates a method for applying waveforms, such as those shown in the preceding Figures, to the human body or a portion thereof, using conductive electrodes, in conjunction with an external fixator for the purpose of bone lengthening.

FIG. 18 illustrates a specific application of the invention to a mode of therapy in which it is desired to stimulate bone growth for the purpose of bone lengthening. In such therapy as it is presently practiced using the Ilizarov and similar fixation means, the bone 150 is cut or broken, and each portion 150a or 150b is then fixed, using sets of rigid pins 152a or 152b, to a generally ring-shaped collar 154a or 154b respectively. For emphasis, the gap between portions 150a and 150b is shown much wider than it would be in actuality. Collars 154a and 154b are connected by extendable means 160, such as threaded rods joined by rotatable threaded sleeves. Pins, collars and connection means alike are commonly made chiefly from metals such as stainless steel. By progressively extending means 160 as new bone forms within the gap 162, the overall length of bone 150 is slowly increased.

All too often, however, this method fails or is drastically slowed because bone does not fill the gap as quickly as desired, or because the new bone does not adequately calcify. The result can be either a permanent bone nonunion, or a porous bone which is at severe risk for re-breakage.

To this conventional therapy, the invention adds electrostimulation for bone regrowth. Conductive skin-contact electrodes 164a and 164b, connected with a signal source 166 made according to the principles of the invention, are placed in such a way that the current flowing between them will include the tissue volume 166 surrounding and including the gap in the bone, but lies clear of pins 152a and 152b since a portion of the applied current could then flow through these pins, the collars and the connection means, rather than through tissue, and thus be wasted.

A waveform such as that of FIG. 4, which is known to stimulate bone growth, is then applied from source 166 through the electrodes, passes through the volume of tissue including the bone gap, speeds regrowth, and encourages calcification. In a test case recently conducted, in which the full intended bone extension had been achieved but the new bone had remained poorly calcified for several months and the adjacent old bone had become osteoporotic, preventing the fixator from being removed, stimulation by this means re-started the growth so that after six more weeks, healing was essentially complete and the pins and other extension means could be removed.

Recently, there has been a new development in this field of treatment: the formerly heavy and X-ray-opaque metal collars 154a and 154b have been replaced by new ones made of composite materials such as fiber-reinforced plastic resin, which are lighter, radiolucent (transparent to medical X-rays), and not electrically conductive. For example, the new Sheffield Ring Fixator from Orthofix (R) includes collars made from such material, perforated with separate sets of holes oriented radially for the fixation pins and axially for the extendable connection means.

Where such electrically nonconductive collars are used, there exists no path for current to flow from one set of pins to the other through the fixator. This may permit skin-contact electrode placement with a greater degree of freedom, or alternatively, may allow the fixation pins themselves to function simultaneously as electrodes.

Figure 19:
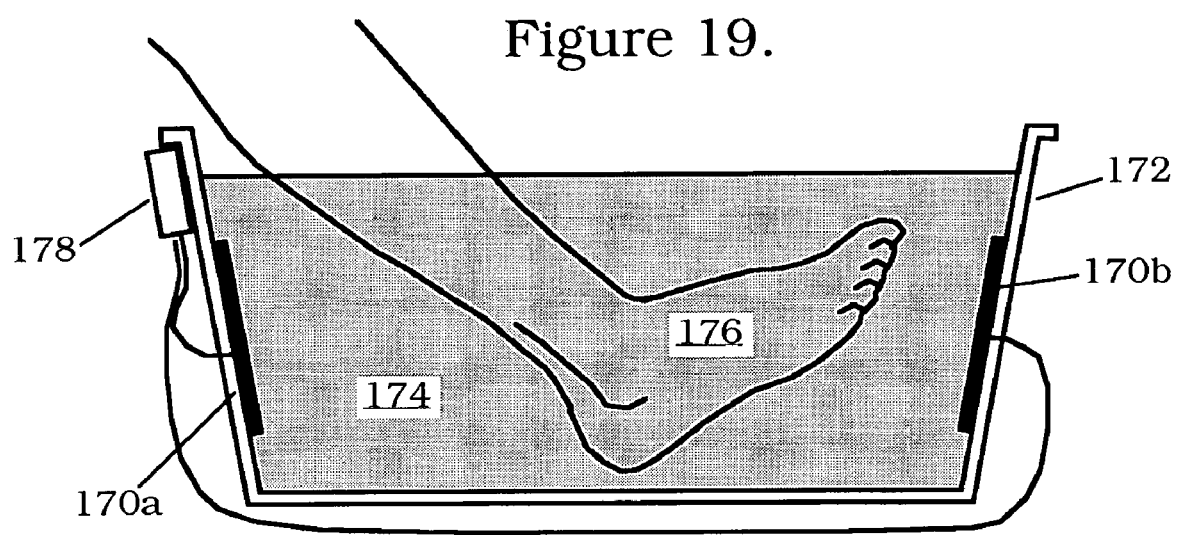
FIG. 19 illustrates a method for applying waveforms, such as those shown in the preceding Figures, to the human body, a portion thereof, or another material, using a bath of conductive liquid.

FIG. 19 illustrates another mode of use of the invention, in which electrodes 170a and 170b are placed on opposing inner surfaces of a tub or other container 172 holding water or other liquid 174 in which one or more conductive ionic salts, such as sodium chloride (table salt) or magnesium sulfate (Epsom salt), are dissolved. Container 172 is itself preferably nonconductive, but if some parts of it, such as plumbing attachments, are conductive, it may be convenient to have them function as one or both of the electrodes, or as portions thereof.

The body part 176 to be treated is immersed in the conductive solution. Body part 176 will generally be that most affected by the condition to be treated. For plantar fasciitis or Achilles' tendonitis, for example, a foot and lower leg might be treated as shown. For systemic conditions, such as osteoporosis or rheumatoid arthritis, it may be more effective to treat the entire body at once, for instance using a suitably modified whirlpool tub.

A suitable signal according to the principles of the invention is generated by a source 178 and passed through the solution and the immersed body part, from one electrode to the other, as described in the preceding sections and Figures. The resistivity of liquid 174, including dissolved salts, preferably lies in the same range as that of living tissues, around 50 to 300 ohm-centimeters. By suitable electrode design and placement, substantially the whole volume of liquid 174 can be made to transmit current at useful intensity levels.

This same application method, or simple variations upon it, can also be used in the treatment of cell or tissue cultures, drinking water and other beverages, pharmaceutical preparations, or other liquid or semiliquid materials.

Figure 20:
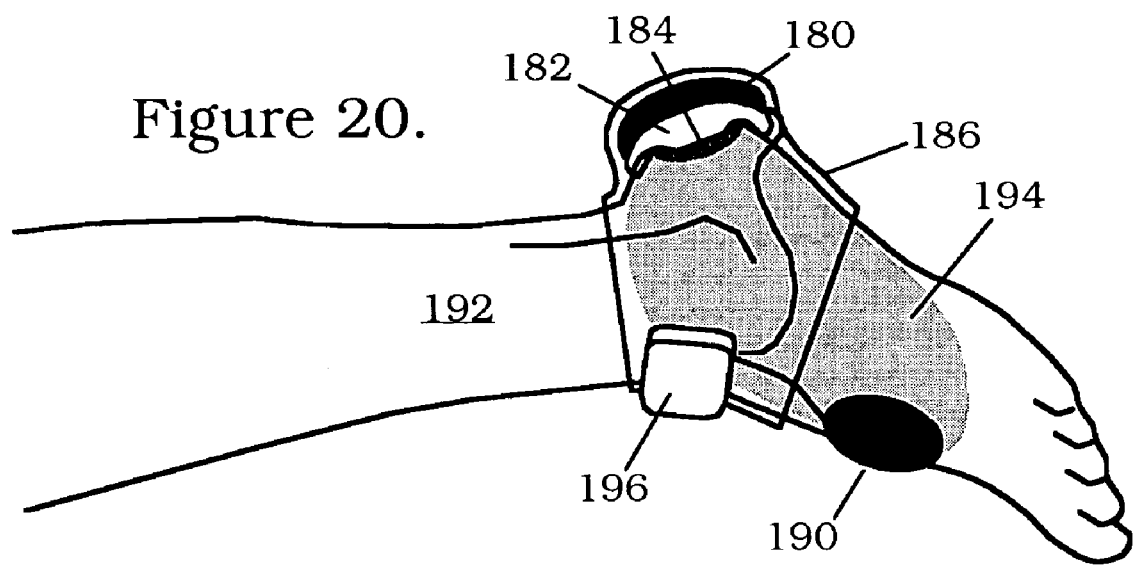
FIG. 20 illustrates a method for applying waveforms, such as those shown in the preceding Figures, to the human body or a portion thereof, using conductive electrodes and a conductive dressing, for the purpose of wound healing.

FIG. 20 illustrates yet another mode of use of the invention, for the purpose of healing chronic wounds such as diabetic or decubitus ulcers. One electrode 180 is placed upon or within an electrically-conductive, sterile dressing 182, in direct contact with the wound surface 184. Electrode 180 is preferably placed directly over the wound surface as shown in the figure, but if for any reason this is impractical, one or more electrodes 180a, 180b and so forth may be placed adjacent to the wound instead.

Electrode 180 (or electrodes 180a, 180b and so forth) and dressing 182 are then preferably covered by an outer, nonconductive dressing 186. The other electrode 190 is placed on healthy skin nearby, and preferably, if practical, on the opposite side of the limb or other body part 192 on which the wound is located, so that the distribution of treatment current 194 is substantially uniform across surface 184. Again, if the use of a single electrode is impractical or cannot give the desired current distribution, multiple electrodes 190a, 190b and so forth may be used instead.

Current 194 is supplied by a compact source 196, made according to the principles of the invention. Source 196 may optionally be attached to, or made a part of, outer dressing portion 186 as shown in the Figure.

The apparatus for generating the signal is another important feature of the present invention. The invention makes it simple to generate any one or any combination of the signals just described using essentially the same, relatively simple circuit made up of inexpensive and widely-available, CMOS integrated circuit components. Using this approach, for example, a combination stimulator can easily be built combining interferential electrotherapy with powered muscle stimulation and perhaps also with other chosen waveforms, yet without the "overhead" of cost, bulk, power demand (with resulting short battery lifetimes) and high manufacturing setup charges which would likely be required for the same functions if implemented using microprocessor technology.

Figure 21:
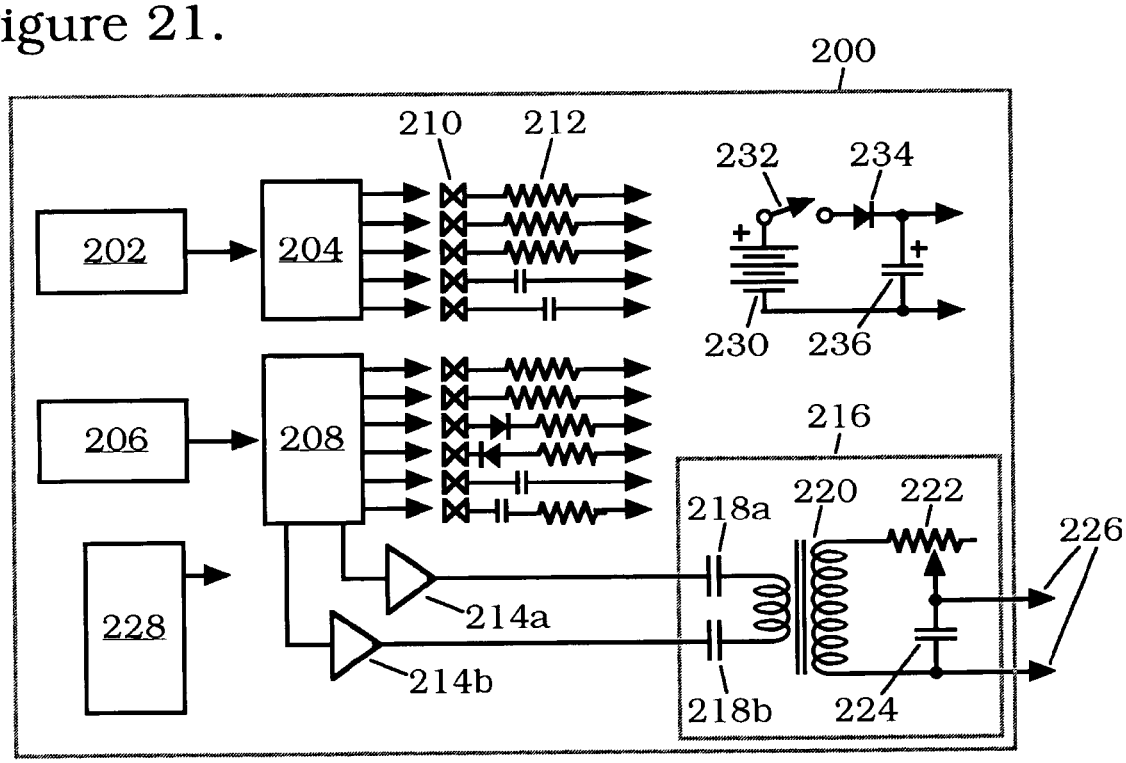
FIG. 21 illustrates a generalized electronic configuration of the invention, using discrete integrated-circuit timers and sequencers.

A waveform according to the present invention, including any of those shown in FIG. 4 or FIGS. 6 through 15, can be generated with an apparatus such as 200, shown in block diagram form in FIG. 21. Apparatus 200 includes the following functional blocks: a first frequency generator 202 and optional sequential switch ("sequencer") 204 which provide the timing for primary intervals $T_1$, $T_2$ and so forth; a second frequency generator 206 and optional sequencer 208 which provide the timing for secondary intervals $t_1$, $t_2$ and so forth; optionally, one or more electronically controlled switches, such as data multiplexers or solid-state analog switches, controlled by the outputs of sequencers 204 and 208 and generally indicated by 210; an array of passive components generally indicated by 212, from which specific combinations are selected by switches 210 if present; output means consisting either of one logic-level driver 214 or, preferably, of two such drivers 214a and 214b, each driving one of the output lines, as shown; output filter 216 optionally including direct-current-blocking capacitors 218a and 218b, a transformer 220, a variable attenuator 222, high-frequency suppression means 224, or any combination of these, resulting in a modified output at terminals 226; and optional timer means 228 which may enable or disable some combination of the other functional blocks at selected times, creating periods within which no output is present.

There exist many different types of electronically-controlled switches, and many conventions for indicating them on schematic diagrams. The switches used in this invention are preferably CMOS analog switches: either the type used in a CD4016B or CD4066B integrated circuit (single-pole, single-throw) or in a CD4053B (single-pole, double-throw). Switches of these types may be used to carry either analog or digital signals, so long as they do not exceed the voltage range between the positive supply and ground.

For simplicity in this and the following Figures, and to distinguish them from conventional, moving-contact switches or relays, these switches will be indicated by the following conventions. Single "bowtie" symbols, as in FIG. 21, will indicate single-throw (CD4016B or CD4066B type) switches. Doubled "bowties" (as, for example, switch 270 in FIG. 23) will indicate double-throw (CD4053B type) switches. In each case, the lines entering the ends of the "bowtie" will be the switched lines while an arrow pointing in from the side represents the control input.

A CD4016B or CD4066B switch is turned on by a logic high ("1") input, and off by a logic low ("0") input. For a double-throw switch, which makes either of two different connections depending on the control input, small numerals "1" and "0" will be placed at the ends of the doubled bowtie symbol (again, as with switch 270 in FIG. 23) to show which input state causes each connection to be made.

Frequency generators 202 and 206 are preferably astable oscillators, each formed by two inverting CMOS logic gates with resistive and capacitive feedback, so that each gate produces two complementary outputs switching alternatively between logic high and logic low voltages. Either one or both of these outputs may be used, depending upon the application. Specific examples of such oscillators will be shown in FIGS. 23 and those following it, and described in the accompanying text.

Sequencer 204 is used if the primary cycle contains more than two primary intervals $T_1$ and $T_2$, or if one or more of these intervals is longer than the practical half-cycle time (time with output constantly either high or low) of frequency generator 202. Otherwise, generator 202 can produce the switching outputs directly as it passes through its inherent two-stage oscillation cycle.

Similarly, sequential switch 208 is used if the secondary cycle contains more than two primary intervals $t_1$ and $t_2$, or if one or more of these intervals is longer than the practical half-cycle time (time with output constantly either high or low) of frequency generator 206. Otherwise, generator 206 can produce the switching outputs directly as it passes through its inherent two-stage oscillation cycle.

Passive components 212 may consist of resistors, capacitors, diodes, or series or parallel combinations of such devices. Components 212 may affect the timing of frequency generators 202, 206, or both. Alternatively, some of switches 210 may control logic signals to select or de-select various circuit functions.

Figure 26:
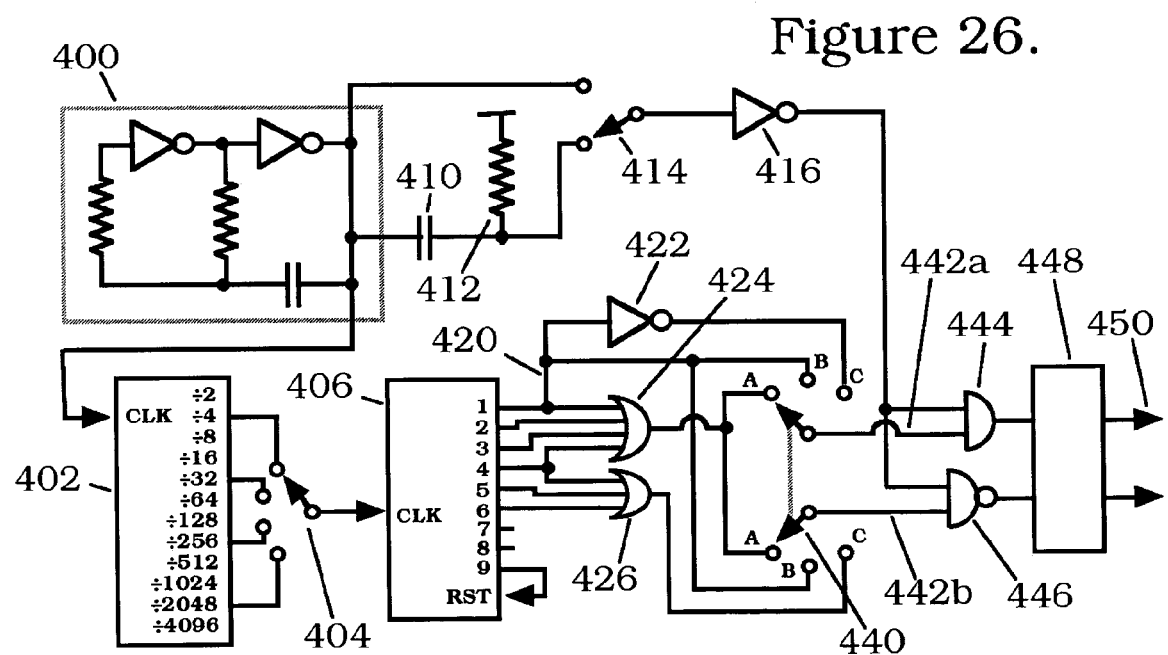
FIG. 26 illustrates a third specific embodiment of the invention, configured to provide a choice of waveforms of types broadly similar to those in FIG. 4, FIG. 6 or FIG. 10.

In some cases it may be practical to combine frequency generators 202 and 206: for instance, by passing the output of generator 202 through a digital division network whose output replaces that of generator 206, as will be illustrated in FIG. 26.

Figure 22:
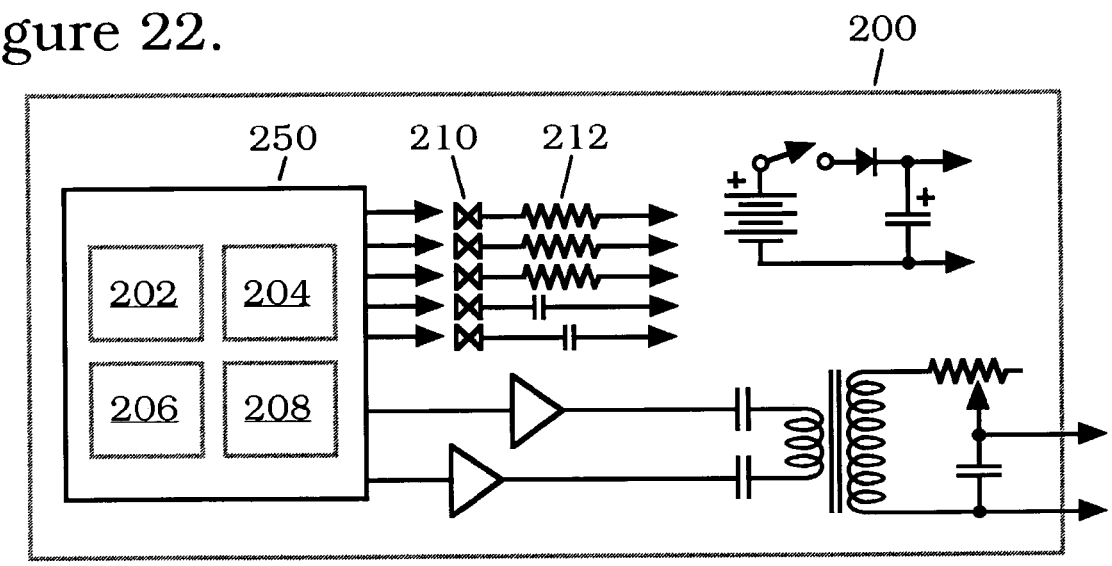
FIG. 22 illustrates a generalized electronic configuration of the invention, using a microcontroller or microprocessor.

Power may be supplied to the invention from the electrical mains (typically 120 or 240 volts A.C. at 50 or 60 Hz) using power-supply means well-known in the art. Since use of the mains poses some risk of electric shock, however, the invention is preferably powered instead by a battery 230, whose output is, for example, approximately between six and eighteen volts. Battery 230 may be either a primary or a rechargeable type, but is more preferably a primary lithium battery because of this type's high power density and relatively flat discharge characteristics. For low-power applications, battery 230 is most preferably a stack of 3-volt lithium coin cells, such as CR2032's, enclosed and held together at their edges by a nonconductive sheath. A power switch 232, a series diode 234, and/or a buffer capacitor 236 may be added to conserve battery life, eliminate any danger from improper battery installation, and minimize the effects of the battery's internal resistance.

Where a number of different modes may be offered in the same device, or where programmability is desirable, it may prove more practical to replace some combination of the frequency generators, sequencers, analog switches and associated passive components with a low-power, CMOS microcontroller 250 (for example, a Microchip PIC16F627), as shown in block form in FIG. 22. Frequency generators 202 and 206, and sequencers 204 and 208, are thus implemented with software modules in the microprocessor program, rather than with discrete, hard-wired components. No change in functionality occurs when this is done; the microprocessor merely takes over some or all of the timing and sequencing functions, so that the corresponding electronic switches 210 and passive components 212 connected to them (typically, any which help to generate the timing) can be eliminated. For some purposes, however, it may be advantageous to retain others of these switches and passive components, as shown, controlling them directly with the microprocessor outputs.

A first specific embodiment of the invention is shown in FIG. 23. For purposes of illustration, this embodiment has been deliberately simplified so as to generate the three-stage prior art primary cycle, with one primary interval subdivided by a secondary cycle, which is shown in FIG. 4 and described in U.S. Pat. No. 6,535,767, or any of a family of alternative waveforms of the same general form but different primary cycle lengths. The circuit shown is thus an alternative means of generating this waveform, illustrating the principles of the present invention by dynamically selecting components 212 which cause the lengths of the primary cycle intervals to differ.

A first frequency generator 260, consisting of two inverting CMOS logic gates 262a and 262b, a fixed resistor 264, a variable resistor 266, and two capacitors 268a and 268b which are alternately selected by switch means 270, runs freely at a frequency set chiefly by resistor 266 and the selected capacitor. Logic gates 262a and 262b may be single gates in any type of CMOS integrated circuit able to operate at the battery supply voltage, but are preferably two of the gates in an integrated circuit of the CD4000B series, which provides buffered outputs.

Switch means 270 is preferably one section of a commonly-available CD4053B triple 2-channel, CMOS analog data multiplexer. As explained above, the small numerals "0" and "1" at the ends of the symbol indicate the connections which it makes with the corresponding input signals. Note that to maintain the switched signal voltage within the range between positive and negative supply levels, a CMOS analog switch is placed between the output of the logic gate and any capacitor to which it is connected. Placing the switch on the opposite side of the capacitor could expose it to out-of-range voltages, with results difficult to predict.

Apart from the provision for electronically switching between alternative capacitor values, and thus between alternative timing or frequency ranges, the oscillator configuration shown is a common one, well-known in the art of circuit design. Assuming ideal component behavior, the cycle time, or time for one complete oscillation, is given by the equation $$T_{CYC} = 2R\,C\,\ln(3)$$

where R is the value of resistor 266, C is the value of the selected capacitor 268a or 268b, and $\ln(3)$ is approximately 1.0986. The cycle time is thus proportional to both the value of the selected capacitor, and the value to which resistor 266 has been adjusted.

The output of generator 260, a square wave, drives a binary, decimal or other digital counter forming a ten-step sequencer 274. Preferably, this counter is a commonly-available CD4017B CMOS decade counter with decoded, "one-of-N" outputs where "N" is normally ten. For simplicity, it is shown on the schematic simply as a box with a clock input and ten numbered outputs. In a CD4017B, since the outputs are numbered beginning with Q0, this output represents step 1, Q1 represents step 2, Q2 represents step 3, and so forth.

For ten steps, the maximum number possible with a single CD4017B chip, the chip's reset input is simply grounded, and hence is not shown in this Figure. Each output is normally at logic low, but is pulled to logic high during the corresponding step of the cycle. The sequencer advances to the next step on a transition of the clock input from logic low to logic high. The sequence is continuous, from 1 up to 10 and then back to 1, so that the cycle repeats as long as clock pulses continue to arrive.

During steps 1 through 9 of sequencer 274, output 10 from the sequencer is at logic low ("0") and switch 270 selects capacitor 268a, while during step 10 the output is at logic high ("1") and the switch selects capacitor 268b instead. The selected capacitor then determines the length of the corresponding step. As a result, steps 1 through 9 are equal in length (apart from startup transients) while step 10 has a different length.

Preferably, capacitor 268a has a value between about 1.5 and about 2.7 times that of capacitor 268b, causing steps 1 through 9 to last longer than step 10 by the same ratio. Resistor 266 may be either a simple potentiometer as shown, or a switch selecting any of a plurality of fixed resistors, singly or in combination. Preferably, resistor 266 has a range of possible values from about 15,000 ohms to about 1.5 million ohms, capacitor 268a has a value of 0.022 microfarad, and capacitor 268b has a value of 0.01 microfarad. The value of resistor 264 is not critical, so long as it is at least twice the highest possible value of resistor 266.

Given these preferred values, with resistor 266 set to a value of about 146,000 ohms, and assuming ideal behavior in all components, steps 1 through 9 of sequencer 274 take 7.05 milliseconds each, while step 10 takes 3.21 milliseconds. The resulting primary cycle often steps thus takes 66.7 milliseconds, for a primary frequency $F_P$ of 15.0 Hz. Other values of resistor 266 give different cycle lengths, but preserve the proportionality between the lengths of all steps. For the range from 15,000 ohms to 1.5 megohms, the corresponding primary frequencies (again assuming ideal response) range from 146 Hz down to 1.46 Hz.

When sequencer 274 is in any of steps 1 through 8, both of output drivers 280a and 280b have their inputs pulled to logic "low" by resistors 282a and 282b respectively, so that their differential output voltage is zero. Steps 1 through 8 therefore appear as a single, continuous interval $T_1$, during which the output maintains a constant output state of zero current or voltage.

When sequencer 274 is in step 9, it turns on a second frequency generator 290, consisting of a two-input CMOS NAND gate 292, an inverting CMOS logic gate 294, three fixed resistors 296, 298 and 300, a diode 302, and a capacitor 304. Again, apart this time from the presence of resistor 300 and diode 302, which permit the generation of an asymmetric output waveform, this is a common oscillator configuration well-known in the art of circuit design. The functioning of the oscillator, when modified by adding the extra resistor and diode, was explained in detail in U.S. Pat. No. 6,011,994, here incorporated by reference. The second NAND gate input, when held at logic high while the sequencer is in step 9, acts as an enabling input which turns on generator 290 only during this interval.

Output signals from generator 290 consist of two complementary logic-level signals on lines 306a and 306b. With the generator turned on, the two lines swap logic states with a frequency and duty cycle given (to close approximations) by the equations $$F_{OSC} = 1/C \ln(3)(R_S + R_P)$$

and $$DC_S = R_S/(R_S + R_P)$$

where $R_S$ is the value of resistor 298 alone, $R_P$ is the value of the parallel combination of resistors 298 and 300 plus a small term contributed by diode 302, C is the value of capacitor 304, and again, ln(3) is approximately 1.0986. The duty cycle here represents the proportion of time spent in the more positive polarity as represented in FIG. 23, rather than in the more negative polarity. Preferably, $R_S$, $R_P$ and C are chosen to place $F_{OSC}$ in the range between 1000 and 2000 KHz, and DC in the range between 67% and 95%, satisfying condition (g) in the previous section. More preferably, $F_{OSC}$ lies in the range between 4000 and 4500 Hz and DC is about 88%. This may be accomplished, for example, by giving resistors 298 and 300 and capacitor 304 stock component values of 180,000 ohms, 33,000 ohms, and 0.001 microfarad respectively.

The signals on lines 306a and 306b are sent respectively to drivers 280a and 280b through switches 310a and 310b, here formed by the two remaining sections of the same CD4053 chip whose first section forms switch 270, but controlled by output 9 from the sequencer. For simplicity, since the "zero turn-on" halves of these switches are not used, the switches are both shown as if single-pole, with a small numeral "1" beside each to show that this is the logical control level which turns it on.

During steps 1 through 8, and also during step 10, switches 310a and 310b receive a logic low control input, and thus make no connection. During step 9, however, they receive a logic high input, turn on, and pass the complementary output signals through to the drivers. This creates a secondary-cycle output signal having the previously-described characteristics during step 9, which thus represents $T_2$ in the primary cycle.

During step 10 of sequencer 254, representing $T_3$ in the primary cycle, generator 260 is once again turned off, and its outputs are disconnected from the output drivers. Diode 312, however, now feeds the positive logic signal from output 10 of the sequencer to the input of driver 208a, overwhelming the effect of resistor 282a, while the input of driver 280b remains held at logic low by resistor 282b. This causes the driver outputs again to assume opposite logic states, thereby generating a differential output voltage equal and opposite to that which was present for a majority of the time during $T_2$ so that, during $T_3$, any resulting charge imbalance is substantially neutralized.

Assuming the component values given above for resistors 264, 266, 296, 298 and 300 and capacitors 268a, 268b and 304, the resulting timing intervals will be approximately $T_1$=56.4 msec (5.8–580 msec), $T_2$=7.05 msec (0.72–72 msec), $T_3$=3.21 msec (0.33–33 msec), $t_1$=198 μsec, and $t_2$=28 μsec, where the first value given for each of $T_1$, $T_2$ and $T_3$ corresponds to the nominal setting of variable resistor 266, while the range shown after it in parentheses represents the range of all possible settings.

To minimize charge imbalance which may result when such neutralization is incomplete, capacitors 314a and 314b form an output filter blocking any remaining net direct current from appearing at outputs 316.

While the circuit of FIG. 23 is significantly more complex than those described in U.S. Pat. No. 6,011,994 and U.S. Pat. No. 6,535,767, it has the advantage of permitting all primary timing intervals to be set by the single variable resistor 266 so that, by changing the value of this resistor, a user can change the pulse-train repetition frequency $F_P$ without affecting the charge balance of the resulting output and without any effect upon the secondary cycle, which maintains a constant frequency $F_S$ (equal to $F_{OSC}$ above) and duty cycle $DC_S$.

A second specific embodiment of the invention is shown in FIG. 24. This implementation can produce either the output waveform of FIG. 7 or that of FIG. 16, or any one of a family of alternative waveforms having the same general form but different primary cycle lengths, secondary cycle lengths, frequency characteristics, or any combination of these.

A first frequency generator 330 and sequencer 332 produce a primary cycle. Frequency generator 330 and sequencer 332 are much the same as in the previous embodiment, except that in the CD4017B chip forming the sequencer, output 5 is connected to the reset input so that, on reaching this state, the sequencer immediately (typically within 200 nanoseconds) returns to step 1. The primary cycle thus consists of only four steps $T_1$, $T_2$, $T_3$ and $T_4$ each corresponding to just one step of the sequencer.

As before, the lengths of the primary intervals are determined in part by switched capacitance in frequency generator 330. Here, however, there are three capacitors 334a, 334b and 334c, all of which are equal in value. Of these, capacitor 334a is connected at all times while the others are connected or disconnected through switches 336a and 336b, respectively, depending upon the sequencer output. A fixed resistor 338 and variable resistor 340 here function in the same way as resistors 264 and 266, respectively, in the previous implementation.

During $T_1$, switches 336a and 336b are both turned off, so that capacitor 334a alone helps set the interval time:

$$T_1 = 2 \ln(3)RC$$

where R is the value of variable resistor 340 and C is that of capacitor 334a. Again, the value of fixed resistor 338 is not critical so long as it is at least twice the maximum value of resistor 340.

During $T_2$, $T_3$ and $T_4$, switch 336a is turned on through inverter 342, driven by output 1 from sequencer 332. (In other words, it is turned off only during $T_1$.) This connects capacitor 334b in parallel with capacitor 334a. In addition, during $T_3$ only, switch 336b is also turned on by output 3 from the sequencer, connecting capacitor 334c in parallel with the others. As a result, $$T_2 = T_4 = 2 \ln(3)R(2C) = 4 \ln(3)RC$$

and $$T_3 = 2 \ln(3)R(3C) = 6 \ln(3)RC$$

so that $T_2$ is twice as long as $T_1$, $T_3$ is three times as long as $T_1$, and $T_4$ is again twice as long as $T_1$.

Simultaneously, a second frequency generator 344 runs at all times except when switched off by inverter 342 during $T_1$. Generator 344 is exactly like generator 290 in FIG. 23, except that the extra diode and resistor there, used to produce asymmetric oscillation, are not present here. As a result, generator 344 produces complementary square-wave outputs on lines 346a and 346b.

Also connected to the outputs of sequencer 332 are NOR gates 348 and 350. Gate 348 is connected to outputs 2 and 3, producing a logic low output during intervals $T_2$ and $T_3$ and a logic high output during intervals $T_1$ and $T_4$. Similarly, gate 350 is connected to outputs 3 and 4, producing a logic low output during $T_3$ and $T_4$ and a logic high during $T_1$ and $T_2$.

The output of gate 348 is fed to one input of a third NOR gate 352, whose other input is the square-wave signal on line 346b. As a result, gate 352's output is at constant logic low throughout $T_1$ and $T_4$, while during $T_2$ and $T_3$ it is the signal on line 346b, inverted.

In like fashion, the output of gate 350 is fed to one input of a fourth NOR gate 354, whose other input is the square-wave signal on line 346a. As a result, gate 354's output is at constant logic low throughout $T_1$ and $T_2$, while during $T_3$ and $T_4$ it is the signal on line 346a, inverted.

Figure 25:
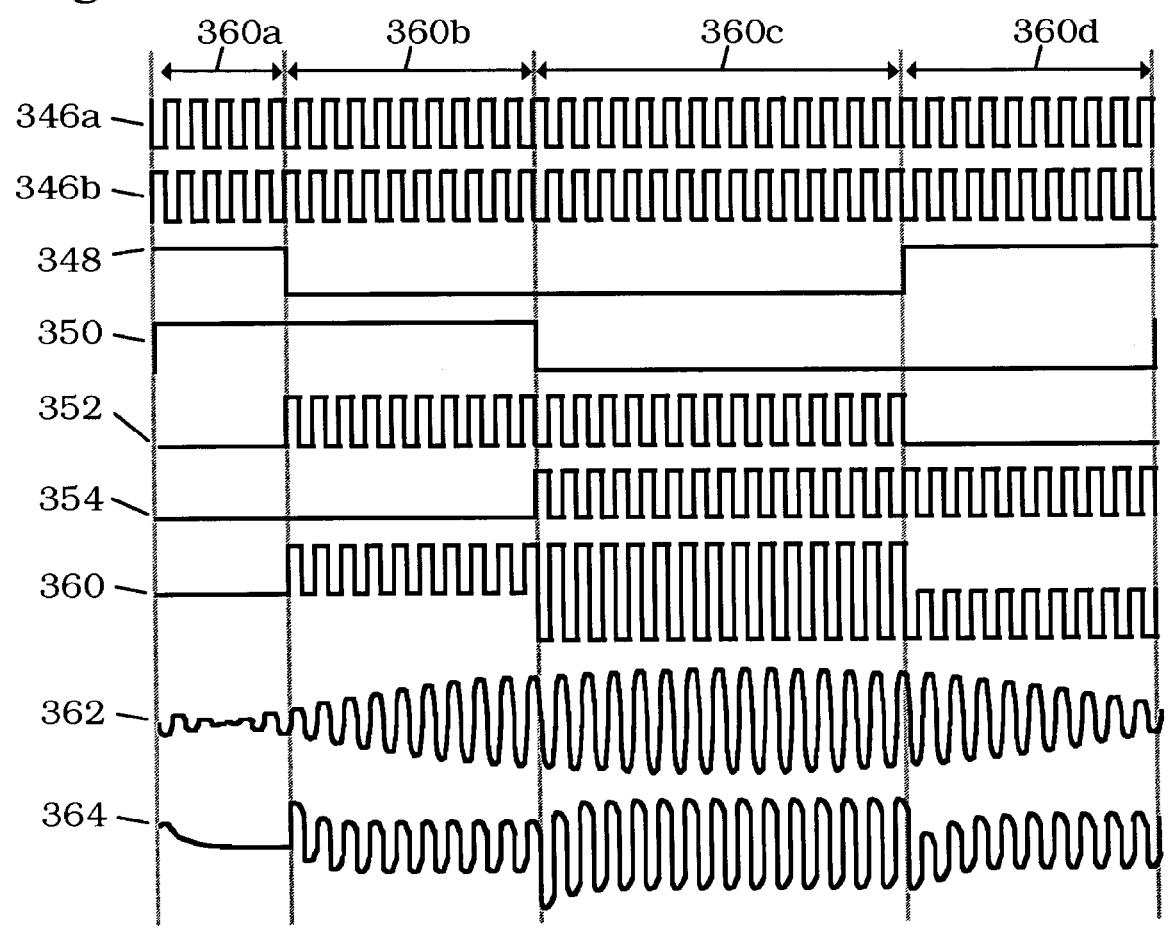
FIG. 25 illustrates waveforms associated with the circuit in FIG. 24.

These relationships are shown in FIG. 25, where intervals 360a, 360b, 360c and 360d are $T_1$, $T_2$, $T_3$ and $T_4$ respectively; traces 346a and 346b represent the voltages on the like-numbered signal lines; and traces 348, 350, 352 and 354 represent the outputs of the like-numbered gates. Trace 360 is simply the difference between traces 352 and 354. Note that trace 360 is identical with that in FIG. 7.

The signal represented by trace 360 has some of the characteristics of the sinusoidally-modulated signal which results from the interference of two sine waves at slightly different frequencies. This is the classic signal used in interferential electrotherapy, in which it is created by applying sine-wave signals at two slightly different frequencies to the body through separate electrode pairs. Such a signal is represented by trace 362.

The signals of traces 360 and 362 are alike in that both have alternating periods of maximum and minimum intensity, with the minimum lasting only a short time while the maximum is relatively long. They differ primarily in harmonic content: since the signal of trace 360 has sharp corners, it contains large amounts of higher frequencies, while the signal of trace 362 does not since the waves are approximately sinusoidal.

The signal of trace 360 may be used for electrotherapy just as it is. Some charge imbalance is present during $T_2$ and $T_4$, but since the waveforms during these intervals are nominally equal and of opposing polarities, it will largely be cancelled out. Any residual imbalance may be canceled, if necessary, by direct-current-blocking capacitors.

In some cases, however, a more nearly "classical" interferential waveform may be desirable. To achieve this, the higher-frequency components may be removed by bandpass or low-pass filtering, preferably using active operational-amplifier circuits. Direct-current output components may simultaneously be blocked.

For example, the single-operational-amplifier, resonant bandpass filter shown schematically in circuit block 356a will perform both of these functions for the output signal of gate 352, by blocking all frequencies outside a chosen, relatively narrow band. Since this circuit is of a type well-known in the art of active filter design, its functioning will not be discussed further here. A second, identical filter 356b, for conciseness shown here only as a blank box, performs the same functions for the output of gate 354. Conveniently, both filters may be made using a low-power, dual operational amplifier integrated circuit such as an LF353N or TL082.

Trace 364 represents the result of such filtering. As is readily apparent, the signal has the same overall characteristics as before but the high-frequency cycles are now considerably more rounded, showing that most harmonics have been eliminated. Note that trace 364 is identical with that in FIG. 16.

A third specific embodiment of the invention, shown in FIG. 26, is designed to produce from the same compact device, and at the user's choice, either an asymmetrically-modulated pulse-train signal similar to that of FIG. 4, suitable for tissue healing stimulation and pain relief; a square-wave-modulated signal of similar form, suitable for muscle stimulation; or a quasi-sinusoidal signal like that of the previous embodiment, suitable for interferential stimulation.

For purposes of illustration, in this embodiment a single frequency generator 400, of conventional form, both directly generates the secondary cycle and drives a binary counter 402, such as a CD4040B integrated circuit, which together with a frequency-selecting switch 404 and sequencer 406, generates the primary cycle. Counter 402 thus functions as secondary frequency generator 206 as shown in FIG. 21.

Generator 400 preferably runs at a frequency in the range between 1000 and 200 KHz, and more preferably in the range between 4000 and 4500 Hz. For simplicity, the operating frequency will be assumed to be 4096 Hz ($2^{12}$ Hz) in the explanation which follows. The basic principles, however, are independent of the actual frequency.

Generator 400 is followed by a pulse-shaping network made up of capacitor 410 and resistor 412, such that, after squaring of the pulses by a following CMOS gate, $$RC = 1/(KF_{OSC})$$

where R is the value of resistor 412, C is the value of capacitor 410, $F_{OSC}$ is the operating frequency of generator 400, and K is a numerical constant determining the duty cycle of the resulting pulse-train waveform. Preferably, K lies in the range from two to fourteen, yielding duty cycles in the range from 67% to 95%, thus satisfying condition (g) in the previous section. More preferably, K is about 5.75, yielding a duty cycle close to 88%. Switch 414 then permits either the symmetric or the asymmetric version of the output waveform to be chosen. Preferably, the signal is then buffered by a gate 416, which may be inverting, as shown.

Binary counter 402 has a plurality of taps representing different binary divisors. Any one of these taps, or preferably any one of a chosen subset of them, may be selected using switch 404. The signal at the selected tap then forms the clock input to sequencer 406, which is configured for eight steps by connecting together the step 9 output and reset input. As a result, the primary cycle frequency represents a further division of the clock frequency by eight. For example, with the subset of selectable taps shown in the Figure, and with an oscillator frequency of 4096 Hz:

| Tap selected | Clock freq. | Primary freq. |
| --- | --- | --- |
| ÷4 | 1024 Hz | 128 Hz |
| ÷32 | 128 Hz | 16 Hz |
| ÷256 | 16 Hz | 2 Hz |
| ÷2048 | 2 Hz | 0.25 Hz |

The output 420 from step 1 of sequencer 406 is inverted by gate 422. OR gate 424 combines the step 1, 2, 3 and 4 output signals from sequencer 406. Similarly, OR gate 426 combines the step 4, 5 and 6 signals.

Two-pole, three-position switch 440 then selects some combination of signals 420, 422, 424 and 426 so that the signals selected by the two poles appear on lines 442a and 442b respectively. In position "A," both poles select signal 424. Similarly, in position "B," both poles select signal 420. In position "C," one pole selects signal 422 while the other selects signal 426, so that these signals appear on lines 442a and 442b respectively.

AND gate 444 then combines the signals from gate 416 and on line 442a, so that the carrier signal is passed through whenever line 442a is high. Similarly, NAND gate 446 does the same for the signals from gate 416 and on line 442a, except that the carrier, when passed through, is also inverted so that the carrier signals from gates 444 and 446 are complementary. Where voltage or current amplification is desired, gates 444 and 446 may either be high-current-output types, or be followed by buffer amplifiers as was shown in FIG. 21.

Filter 448 then preferably blocks DC and frequency components above about 40 KHz (10 $F_S$) and steps up the output voltage if necessary, yielding a differential output at terminals 450. Filter 448 may optionally be given a plurality of different filtering and/or voltage step-up characteristics, also switch-selected, to suit the different waveforms and their intended applications.

Figure 27:
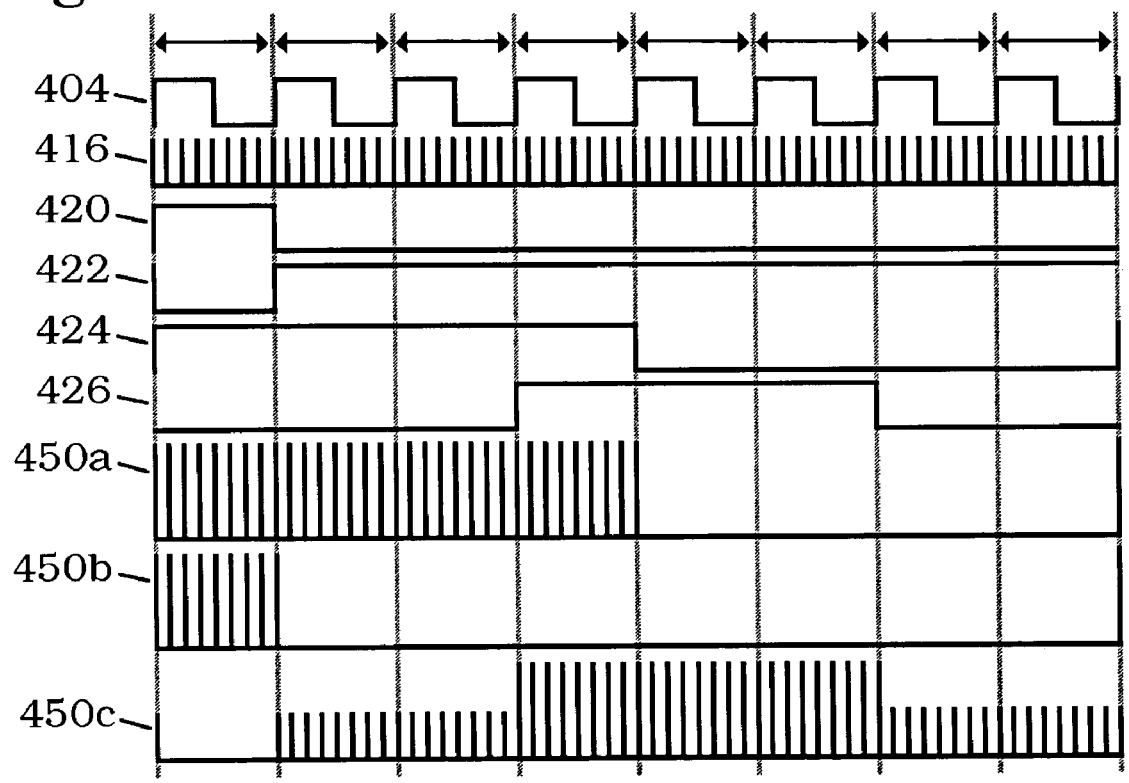
FIG. 27 illustrates waveforms associated with the circuit in FIG. 26.

The result is shown in FIG. 27. Trace 404 represents the clock input to sequencer 406. Trace 416 represents the selected carrier waveform, here shown as asymmetric; the cycle length is exaggerated for clarity. Trace 420 represents the Step 1 output, and traces 424, 426, and 432 the signals on the corresponding lines in FIG. 26. Traces 450a, 450b and 450c represent the resulting differential output signals 450 for positions "A," "B" and "C" of switch 440, respectively, neglecting any effects of filter 448.

Switches 404, 414 and 440 may be either electronic switches, such as those in a CD4016B, CD4051B, CD4052B or CD4053B integrated circuit, or conventional mechanical switches. In either case, it may be desirable to limit the possible combinations of settings to some conveniently small number representing the output waveforms which are the most generally useful. For example, all choices could be combined in a custom, multipole rotary switch, similar to those used in digital multimeters, with one position yielding each chosen combination and one more position turning the stimulator off.

Examples of desirable waveforms available from this embodiment, and the switch combinations yielding them, are:

| Waveform | Switch 404 | Sw. 416 | Sw. 440 |
| --- | --- | --- | --- |
| Muscle stimulating | Symmetric | ÷2048 | A |
| Tissue stimulating | Asymmetric | ÷32 | B |
| Interferential | 2 Hz, Symmetric | ÷256 | C |
| Interferential | 16 Hz, Symmetric | ÷32 | C |
| Interferential | 128 Hz, Symmetric | ÷4 | C |

The muscle-stimulating waveform consists of two-second pulse bursts causing muscle fibers to contract, alternating with two-second periods of no signal, permitting them to relax. The tissue-stimulating waveform is similar to that generated by the first embodiment of the invention, while the interferential waveform is similar to that generated by the second embodiment.

Figure 12:
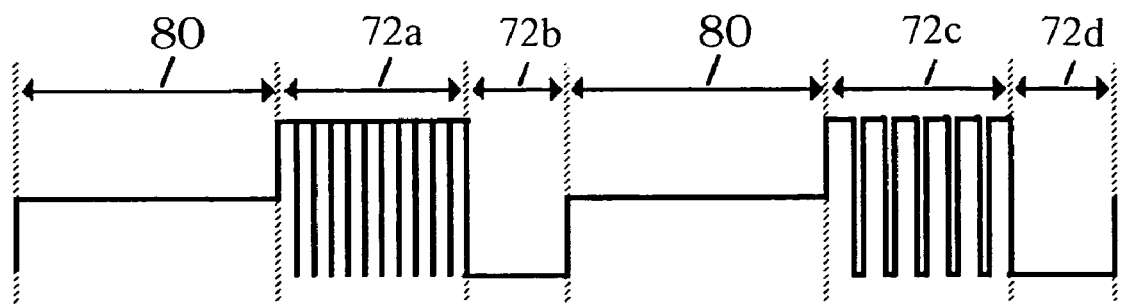
FIG. 12 illustrates a waveform according to the invention, having two different carrier frequencies contained within alternate pulses of a pulsed envelope.

A fourth specific embodiment of the invention is designed to produce a nonsinusoidal, asymmetric but charge-balanced output similar to that which was shown in FIG. 15, but also containing the secondary-cycle frequency shift which was shown in FIG. 12. This embodiment is shown in FIG. 28.

A frequency generator 500, similar to that in the previous embodiment, drives a sequencer 502 having ten steps just as in the first embodiment described. Since generator 500 has no time-varying components, it runs at a constant rate, which is preferably about one step per second. The full cycle of sequencer 502 is thus completed in about ten seconds.

A NOR gate 510 combines sequencer outputs 2, 3, and 4, producing a logic low output during these steps and logic high otherwise. A second NOR gate 512 does the same with outputs 1 and 5, producing a logic low during these steps and logic high otherwise. These outputs define $T_1$ through $T_4$ so that $T_1$ equals step 1, with the output of gate 510 high but that of 512 low; $T_2$ equals steps 2, 3, and 4 combined, with the output of gate 510 low but that of 512 high; $T_3$ equals step 6, with the outputs again as in $T_1$; and $T_4$ equals the sum of steps 6 through 10, with both outputs high. Hence, $T_1$ and $T_3$ are equal and last about one second each, while $T_2$ lasts about three seconds and $T_4$ lasts about five seconds. The cycle then repeats.

A NAND gate 514 then combines the outputs of gates 510 and 512, so that its output is at logic low during $T_4$ but logic high at all other times. (An identical output could be obtained from a NOR gate fed by sequencer outputs 6 through 10 or, in a CD4017B or equivalent integrated circuit, directly from the COU, ("Carry $_{Out}$") pin.

A second frequency generator 520 is made up of a NAND gate 522, an inverter 524, three resistors 526, 528 and 530, a diode 532, a capacitor 534a which is permanently connected, and a second capacitor 534b which can be placed temporarily in parallel with it through switch 536, controlled by gate 510 so that it is disconnected during $T_2$. Generator 520 produces a single output on line 538. Gate 522 is controlled by the output of gate 512, so that generator 520 runs only during $T_2$ and $T_4$, while signal 512 is high, producing an oscillating output on line 538, while during $T_1$ and $T_3$ signal 512 is low and oscillator 520's output is also held constantly low.

The combination of resistor 530 and diode 532, connected in parallel with resistor 528, renders the oscillation asymmetric as was explained in U.S. Pat. No. 6,011,994. With diode 532 oriented as shown, the signal on line 538 is at logic high about 88% of the time during oscillation. Resistors 526, 528 and 530 preferably have values of about 2.2 megohms, 270,000 ohms, and 27,000 ohms, respectively, and capacitors 434a and 434b, about 0.01 microfarad and one microfarad respectively.

With this circuit configuration and with these values, during $T_2$ only capacitor 534a is in the circuit and the output of generator 520 spends alternate periods of about three milliseconds at logic high and 0.3 millisecond at logic low, for a secondary frequency $F_S$ of about 300 Hz. During $T_4$, the value of capacitor 534b is added to that of capacitor 534a, and the generator output spends about 300 milliseconds high and 30 milliseconds low, for a secondary frequency of about 3 Hz.

An XOR (exclusive OR) gate 540 receives as inputs the signal on line 538 and that from gate 510, which as stated above is at logic high during $T_1$, $T_3$ and $T_4$ but at logic low during $T_2$. As a result, gate 540 passes the signal from line 538 unchanged during $T_2$ but inverts it at all other times.

Similarly, a second XOR gate 542 receives as inputs the signal on line 538 and that from gate 514, which is at logic high during $T_1$, $T_2$ and $T_3$ but at logic low during $T_4$. As a result, gate 540 passes the signal from line 538 unchanged during $T_4$ but inverts it at all other times.

The outputs of gates 540 and 542 respectively feed buffer amplifiers 544a and 544b. The output from this embodiment of the invention consists of the differential signal between these two buffer outputs.

Figure 29:
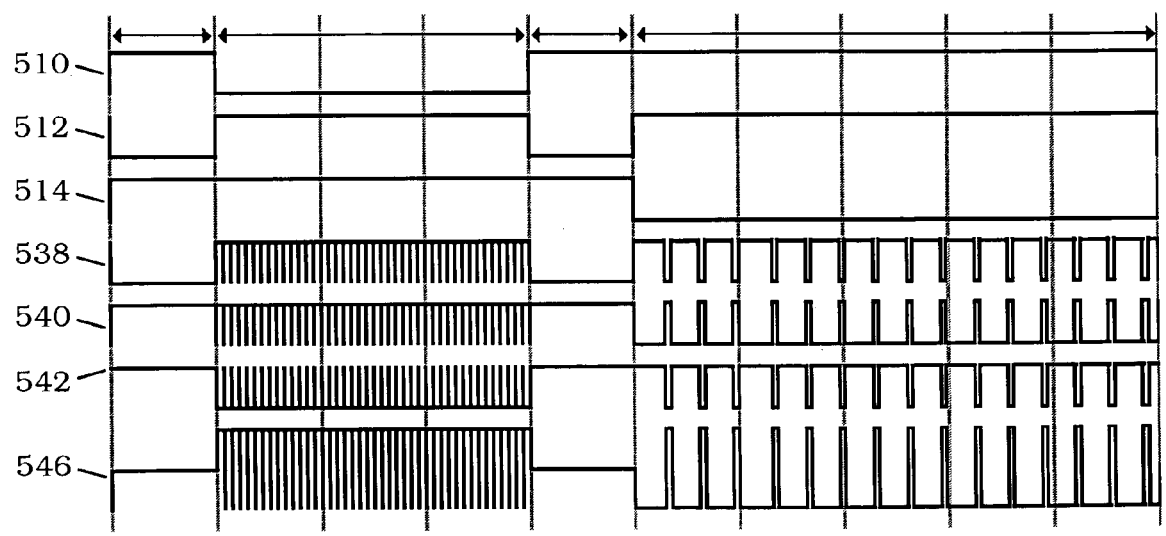
FIG. 29 illustrates waveforms associated with the circuit in FIG. 28.

The resulting signals are illustrated in FIG. 29, in which trace 538 is the output of generator 520 on line 538; traces 510, 512, 514, 540 and 542 are the outputs of the like-numbered gates; and trace 546 is the differential output signal from buffers 544a and 544b. The secondary cycle lengths during $T_2$ are shown, and the number of cycles correspondingly reduced, so that the change in polarity between $T_2$ and $T_4$, corresponding to that which was shown in FIG. 5, is evident. Note that apart from this reversal, trace 544 is substantially identical with the trace in FIG. 12.

In some cases, intermittent rather than continuous treatment may be desirable. For example, in the treatment of mild to moderate pain it may be best to allow the patient to control the dosage: starting the treatment upon the press of a button, allowing the signal to be generated for a preset period such as 30 or 60 minutes, then turning it off until the patient presses the button again, and so forth. Alternatively, the "off" period could also be preset so that the device would cycle continuously between "on" and "off" periods of a half-hour to several hours each, or require a preset minimum "off" interval before accepting another button press.

In either case, the output of frequency generator 500 may conveniently be applied to a binary or other counter chain 550, much as in the previous embodiment, whose output 552 drives an additional input of gate 512. Signal 552 may either be taken from a single output as shown, or be derived from several such outputs: for example, by using a NOR gate in an arrangement similar to that of gate 510, followed by an inverter. Signal 552 is initially at logic low, enabling gate 512 and frequency generator 520 to operate as previously described. Upon the attainment of a specific count in counter 550, however, signal 552 changes to logic high, forces gate 512's output to logic low, and thus disables generator 520 and forces the differential output signal from buffers 544a and 544b to zero.

Depending upon the arrangement of counter 550, further counting may then be disabled so that there will be no further output from the buffers until the counter is reset to zero, for example by the press of a button as previously described. Alternatively, the count may be allowed to continue so that upon the attainment of some other specific count, generator 520 will be enabled again and the output will resume periodically, for specified lengths of time, separated by specified intervals of zero output. Other options are also possible with slight modifications of the circuitry described.

A fifth specific embodiment of the invention is designed to produce a nonsinusoidal, approximately exponentially-decaying signal whenever it is triggered by an external source.

Figure 30:
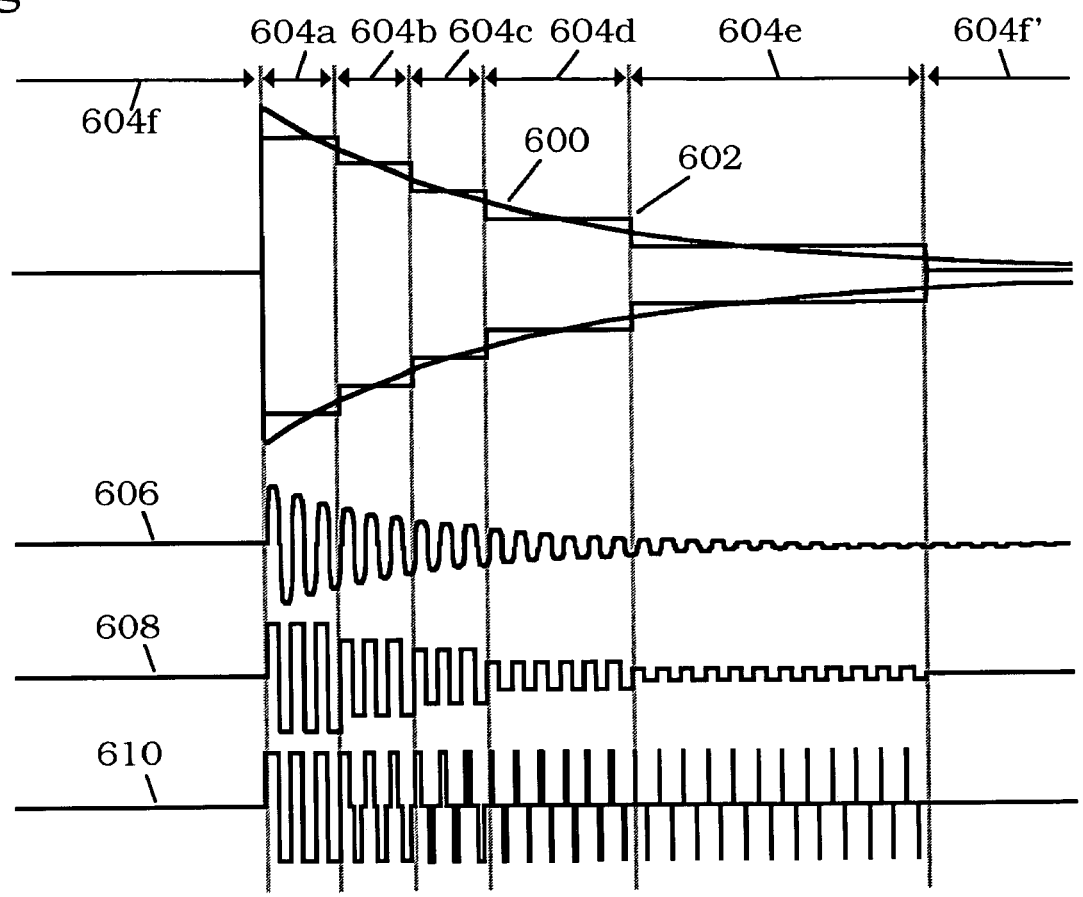
FIG. 30 illustrates an exponential decay curve and various signal types having envelopes which decay approximately exponentially.

An idealized curve of symmetrical exponential decay is shown in FIG. 30 by trace 600; note that this reproduces trace 110 in FIG. 5, except that it is shown on a larger scale. Trace 602 shows an approximation made up of five intervals 604a, 604b, 604c, 604d and 604e, each containing a carrier signal with steady amplitude which steps downward from each interval to the next, plus an interval 604f of zero amplitude. According to the principles of the invention, interval 604f represents primary interval $T_1$, while intervals 604a, 604b, 604c, 604d and 604e represent $T_2$, $T_3$, $T_4$, $T_5$ and $T_6$ in turn. The Figure shows a representative portion 604f of $T_1$ at the start, followed by the other five primary intervals in turn, and finally a representative portion 604f' of $T_1$ from the next primary cycle. So that the steps in trace 602 may be more clearly seen, the vertical hatching which was used in FIG. 5 to indicate the presence of a secondary cycle is here omitted.

Intervals in the primary cycle, beginning with $T_2$ and ending with $T_6$, may be either equal or successively longer. Preferably, intervals $T_2$, $T_3$ and $T_4$ all have the same length, interval $T_5$ has twice this length, and interval $T_6$ has four times this length. More preferably, given this time relationship, the relative amplitudes of the signal during $T_2$, $T_3$, $T_4$, $T_5$ and $T_6$ are close to 100%, 80%, 60%, 40% and 20%, respectively. The amplitude during $T_1$, as previously stated, is zero. Depending upon the application, $T_1$ may be either fixed in length, yielding a periodic signal, or arbitrarily long, yielding a signal which is aperiodic.

Trace 606 shows an oscillating signal which decays exponentially with an amplitude following the curve of trace 600. Trace 608 shows a signal according to the principles of the invention which follows approximately the same decay curve, using multiple levels of voltage or current as indicated by trace 602. Trace 610 shows a more practical signal according to the principles of the invention, in which only three voltage or current levels are used but the effective amplitude is decreased by changing the time relationships of these levels within the secondary cycle, again as indicated by trace 602. Note that trace 610 is identical with the trace which was previously shown in FIG. 11.

Figure 31:
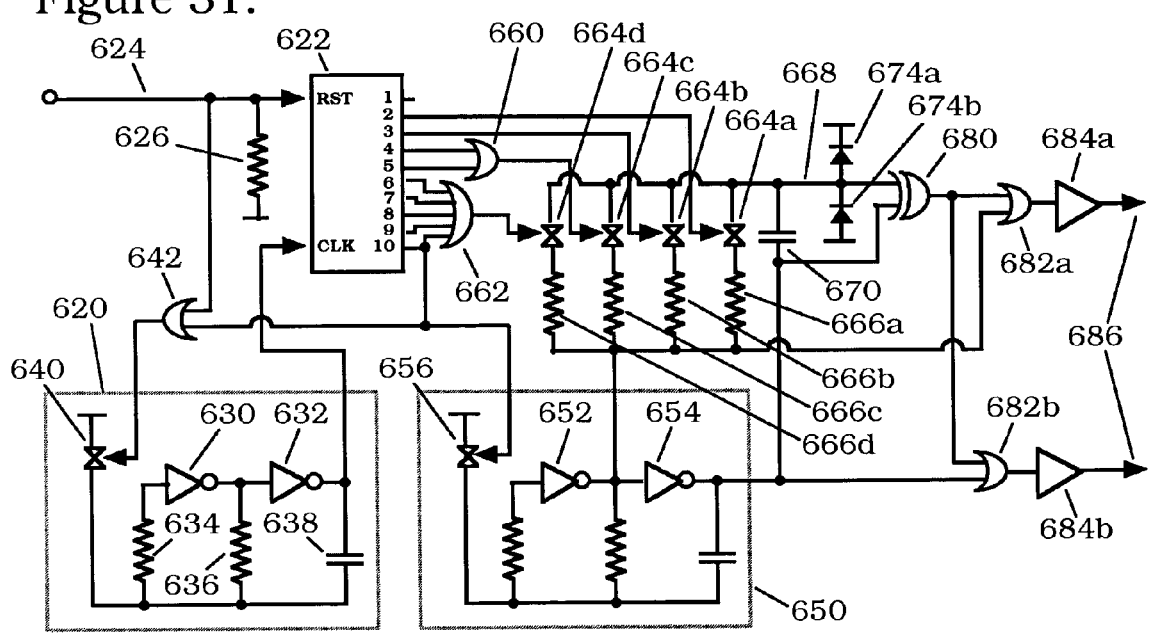
FIG. 31 illustrates a fifth specific embodiment of the invention, configured to generate a waveform similar to the bottom one in FIG. 30.

FIG. 31 shows an example of a circuit able to generate the waveform of trace 610, or any of a large family of similar ones. As noted above, signals of this general form, when applied at relatively high intensities, have been shown to devitalize some microorganisms in vitro and might thus be useful in the preservation of foodstuffs or beverages, or in the sterilization of pharmaceutical materials or drinking water. Since it is not intended for direct connection to a human or animal body, the circuit shown in FIG. 31 might be powered either by batteries like the preceding embodiments, or by the electric mains.

A first frequency generator 620 and sequencer 622 generate ten timing steps. Sequencer 622's "reset" input is connected to an external input line 624 which is normally held at logic low, for example by a resistor 626.

Generator 620 is of the general form previously described, consisting of inverting gates 630 and 632, resistors 634 and 636, and capacitor 638, but differs in that a switch 640, when turned on, connects the junction of resistors 634 and 636 and capacitor 638 to the positive supply. This halts the generator with the output of gate 632 also high, so that capacitor 638 is essentially discharged with both terminals at logic high. When switch 640 re-opens, generator 620 then re-starts from a known state and thus with known and reproducible initial timing intervals before its next transitions. Assuming ideal component characteristics, the interval between the switch's opening and the output's next transition to logic high, advancing sequencer 622, will be $$T_{T1} = (\ln(2) + \ln(3))RC \approx 1.792 RC$$

where R is the value of resistor 636 and C is the value of capacitor 638. As generator 620 continues to run, further transitions to logic high will occur at intervals of $$T_{T2} = 2 \ln(3)RC \approx 2.197RC$$

with sequencer 622 advancing at those times.

Upon sequencer 622's reaching step 10, this output raises one input of OR gate 642 high, forcing its output also high. This closes switch 640, stopping generator 620 as already described. Since the sequencer can then receive no more clock pulses, it remains in this state until it is reset to step 1 by a logic high at input 624.

Input 624 also feeds gate 642, so that generator 620 remains disabled as long as the input remains at logic high. Only when input 624 returns to logic low will generator 620 begin again to oscillate: advancing sequencer 622 to step 2 after about 1.792 RC, then to each of the following steps at intervals of about 2.197 RC, until it again reaches step 10 and halts awaiting another reset input.

A second frequency generator 650 is identical with generator 620, save that it operates at a sufficiently higher frequency that at least two, and typically several hundred, secondary cycles occur during each step of sequencer 622, and that complementary outputs are taken from inverting gates 652 and 654. The operating frequency of generator 650 is the carrier frequency.

Like generator 620, generator 650 contains a switch 656 which, when turned on, halts it in a reproducible state. Switch 656 is driven directly by output 10 of sequencer 622, so that it is halted during step 10 but runs at all other times, including $T_1$.

Outputs 4 and 5 of sequencer 622 are combined by OR gate 660, producing a single output which is at logic high throughout steps 4 and 5. Similarly, outputs 6, 7, 8, 9 and 10 are combined by OR gate 662, producing a single output which is at logic high throughout steps 6 through 10.

Outputs 2 and 3 from sequencer 622, and the outputs of gates 660 and 662, control switches 664a, 664b, 664c and 664d respectively. Each of these, when turned on, switches a different-valued resistor 666a, 666b, 666c or 666d into series with the output from gate 652. Resistors 666a, 666b, 666c and 666d are successively smaller in value, and are connected to a common line 668, to which the output of gate 654 (complementary to that of gate 652) is also connected through a capacitor 670.

Figure 32:
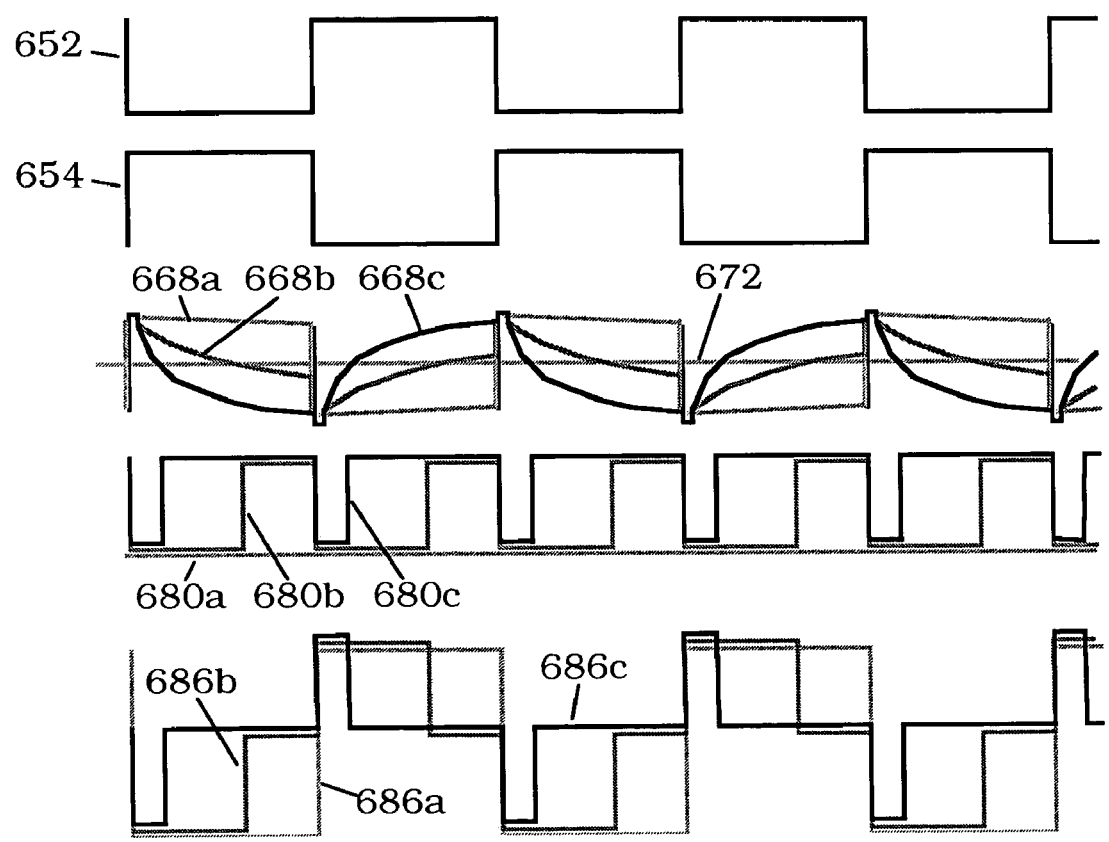
FIG. 32 illustrates waveforms associated with the circuit in FIG. 31.

The result of this arrangement is shown in FIG. 32, where traces 652 and 654 represent the outputs of the like-numbered gates, and traces 668a, 668b and 668c represent the voltage on line 668 under three different operating conditions and over a few cycles of the carrier frequency: trace 668a with none of resistors 656a through 656d selected, trace 668b with a relatively large-valued resistor selected, and trace 668c with a relatively smaller-valued resistor selected.

Each of voltages 668a, 668b and 668c rises or falls abruptly with each upward or downward transition of gate 654. Diodes 674a and 674b prevent this voltage from significantly exceeding the supply voltage range. Thereafter, voltage 668 decays toward voltage 652 with a time constant determined by the values of capacitor 670 and the selected resistor.

XOR gate 680 then compares voltages 654 and 668. Since a 4000B-series CMOS gate undergoes output transition at an input voltage about halfway between the supply voltages (indicated by horizontal, hatched line 672 in FIG. 32), gate 680 generates a logic low output during each half-cycle of generator 650 for so long as the difference between voltages 654 and 668 remains less than one-half the supply voltage, and a logic high output thereafter, as indicated by traces 680a, 680b and 680c respectively for the conditions of no resistor, high-valued resistor and low-valued resistor selected. (These traces are slightly offset from each other in the Figure, for better visibility.) The result is a logic low pulse, repeated at twice the carrier frequency, whose length is approximately proportional to the value of the selected resistor. Where no resistor is selected, the result is a continuously low logic level.

OR gates 682a and 682b then compare voltage 680 with voltages 652 and 654 respectively, each generating a logic low pulse corresponding to that from gate 680 during the corresponding logic-low half cycle of voltage 652 or 654, respectively. Buffered (and preferably voltage-amplified) by output buffers 684a and 684b, these create a differential output 686 as indicated by traces 686a, 686b and 686c for the respective resistor selections. Again, these traces are slightly offset from each other in the Figure for better visibility.

During sequencer step 10 when generator 650 is disabled, resistor 666d remains selected, the inputs of gate 680 are thus pulled quickly to and remain at opposite logic levels, and its output generates a constant logic high which is passed through to both outputs so that the differential voltage between them is zero.

Step 10 of sequencer 622 represents interval $T_1$ of the primary cycle, when the sequencer is halted with generator 650 also turned off and with zero differential output.

In step 1, either with line 624 high or until the first transition of gate 632's output after line 624 goes low again, generator 650 runs but no resistor is selected. Hence, the voltage on line 668 (trace 668a) is essentially the same as that coming from the output of gate 654 and the differential output is at maximum duty cycle: a square wave at the carrier frequency, running from full positive to full negative output voltage or current. This represents interval $T_2$ of the primary cycle.

In step 2, step 3, steps 4 and 5 together, and steps 6, 7, 8 and 9 together, successively lower resistor values are selected, causing the output to take the form of successively narrower pulses, alternately of full positive and full negative output voltage or current, separated by successively longer periods of zero output, thereby approximating exponential decay through progressive changes in duty cycle. In each case, the signal (considered as pairs of one positive and one negative pulse each) repeats at the carrier frequency but with successively greater portions of time spent at zero voltage or current. These sequencer steps or step combinations thus represent $T_3$, $T_4$, $T_5$ and $T_6$ of the primary cycle.

Following step 9, the sequencer returns to step 10 ($T_1$) and the cycle will then repeat itself upon receipt of another positive pulse at input 624. The resulting cycle may be rendered periodic, if desired, simply by applying periodically-spaced pulses to the input, separated by intervals longer than nine cycles of generator 620. Alternatively, the cycle may be started aperiodically each time a specified set of process conditions, such as the correct placement of a vessel or volume of material to be treated between the output electrodes, is attained.

Figure 33:
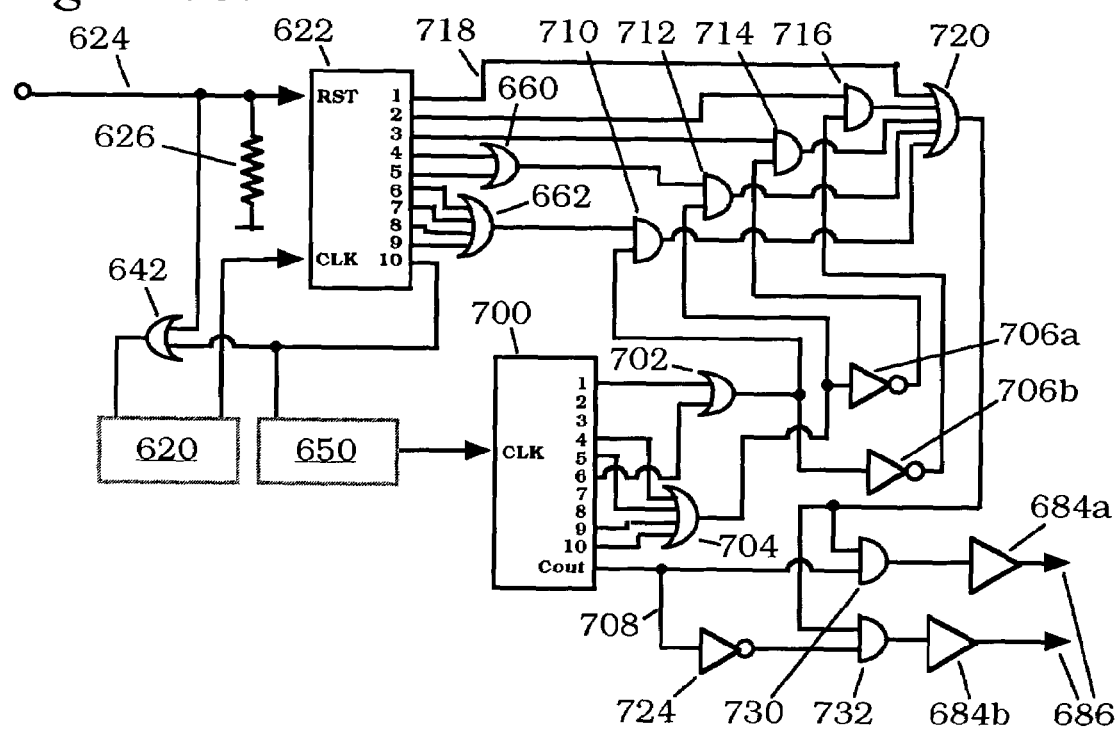
FIG. 33 illustrates a sixth specific embodiment of the invention, also configured to generate a waveform similar to the bottom one in FIG. 30 but with greater precision and reproducibility.

All of the embodiments so far described use multistep sequencers only in their primary cycles, with all needed secondary intervals generated by two-state frequency generators and ancillary circuitry. A sixth specific embodiment of the invention, shown in FIG. 33, illustrates the use of a multistep secondary cycle and sequencer in generating outputs like those of the preceding embodiment, but with greater consistency and precision.

A primary frequency generator 620 and secondary frequency generator 650 are identical with like-numbered components in the previous embodiment and function in the same way, save that here generator 650 operates at ten times the desired carrier frequency. For simplicity, these generators are shown in FIG. 33 only in outline. A primary sequencer 622 and OR gates 642, 660 and 662 are also identical with like-numbered components in the previous embodiment, except that here gate 662 combines the signals only from steps 6 through 9. Apart from its lack of a connection to gate 662, the output from step 10 of the sequencer operates exactly as in the preceding embodiment.

The output of generator 650, however, now provides a clock input to sequencer 700, which like sequencer 622 is configured for a cycle of ten equal steps. Sequencer 700's "reset" input is grounded, and not shown in the Figure.

Like those of sequencer 662, also, the outputs of sequencer 700 are combined by OR gates to yield more complex outputs. Gate 702 combines outputs 1 and 6 yielding a signal with a 20% duty cycle, while gate 704 combines outputs 4, 5, 9 and 10 yielding a signal with a 40% duty cycle, both at twice the carrier frequency (one-fifth the frequency of generator 650). Signal 704 is inverted by gate 706a, and signal 702 by gate 706b, yielding signals of like frequency but at 60% and 80% duty cycle, respectively.

A third OR gate 708 combines outputs 1, 2, 3, 4 and 5 of sequencer 700, yielding a signal at 50% duty cycle at the carrier frequency. A CD4017B package already includes such a gate, producing an output "Cout" ("carry out") which is normally used in combining a plurality of such chips to form a multi-stage counter; hence, gate 708 is not shown in the Figure and only its output line is labeled. If a different type of integrated circuit is used to form sequencer 700, gate 708 may need to be added externally.

Figure 34:
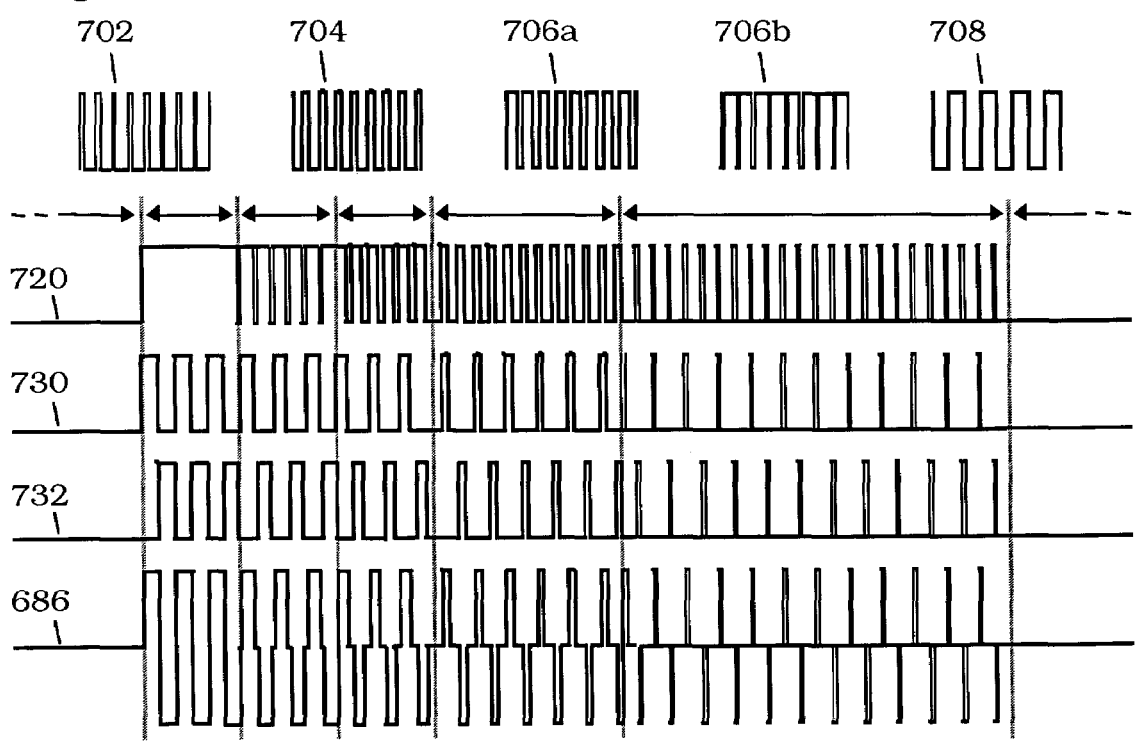
FIG. 34 illustrates waveforms associated with the circuit in FIG. 33.

Signals 702, 704, 706a, 706b and 708, representing the outputs of the like-numbered gates, are shown in a row across the top of FIG. 34.

AND gate 710 combines the signal from gate 662, representing steps 6 through 9 of sequencer 622, with the signal from gate 702, representing a 20% duty cycle. Similarly, AND gate 712 combines the signal from gate 660, representing steps 4 and 5, with that from gate 704, representing a 40% duty cycle; AND gate 714 combines the signal directly from step 3 with that from gate 706b, representing a 60% duty cycle; and AND gate 716 combines the signal directly from step 2 with that from gate 706a, representing an 80% duty cycle.

Note that the signal from step 1 of sequencer 622, carried on line 718, is always on, representing a 100% duty cycle, throughout step 1.

OR gate 720 then combines the signal on line 718 with those from AND gates 710, 712, 714 and 716. The resulting signal is a rectangular pulse at twice the carrier frequency, whose duty cycle varies with the step of sequencer 622: 100% (always high) in step 1 ($T_2$), 80% in step 2 ($T_3$), 60% in step 3 ($T_4$), 40% in steps 4 and 5 ($T_5$), and 20% in steps 6 through 9 ($T_6$). Since sequencer 622's step 10 output is not connected to gate 662, the gate's output signal is continuously low during this step ($T_1$), representing a duty cycle of zero.

Sequencer 700's "Cout" signal 708, as stated above, is a square wave at the carrier frequency, while signal 720 runs at twice this speed. As a result, one pulse of signal 720 falls within each half-cycle of signal 708: one while it is high, the other while it is low.

Inverter 724, taking signal 708 as its input, creates a second, complementary square wave: high when signal 708 is low, and low when it is high. AND gate 730 then combines signals 708 and 720, so that its output consists of pulses of the same lengths as in signal 720, but only during the positive half-cycle of signal 708. Similarly, AND gate 732 combines signals 720 and 724, so that its output consists of pulses of the same lengths as in signal 720, but only during the negative half-cycle of signal 708. The pulses from gates 730 and 732 thus alternate: one from gate 730, one from gate 732, another from gate 730, and so forth.

Applied to buffers 684a and 684b, these signals create a differential output 686 which is closely similar to that of the preceding embodiment, approximating an exponentially-decaying sine-wave signal through a plurality of time periods containing rectangular waves having successively decreasing duty cycles. Here, however, since the timing is all-digital, it is more accurate and reproducible.

All of the above relationships may be expressed more concisely by writing Boolean expressions for the various signals:

$A1 = T_2 \quad A2 = T_3 \quad A3 = T_4 \quad A10 = T_1$ $660 = A4 + A5 = T_5$ $662 = A6 + A7 + A8 + A9 = T_6$ $702 = B1 + B6 = 1000010000$ $704 = B4 + B5 + B9 + B10 = 0001100011$ $706a = 0111101111$ $706b = 704 = 1110011100$ $708 = B1 + B2 + B3 + B4 + B5 = 1111100000$ $710 = 662 \times 702 =$
$\quad (A6 + A7 + A8 + A9) \times (B1 + B6) = T_6 \times 1000010000$ $712 = 660 \times 702 = (A4 + A5) \times (B4 + B5 + B9 + B10) =$
$\quad T_5 \times 0001100011$ $714 = A3 \times 706b = A3 \times () = T_4 \times 1110011100$ $716 = A2 \times 706a = A2 \times () = T_3 \times 0111101111$ $718 = A1 = T_1 = T_2 \times 1111111111$ $720 = 718 + 716 + 714 + 712 + 710 =$
$\quad (T_1 \times 0000000000) + (T_2 \times 1111111111) +$
$\quad (T_3 \times 0111101111) + (T_4 \times 1110011100) +$
$\quad (T_5 \times 0001100011) + (T_6 \times 1000010000)$ $724 = 0000011111$ $730 = 720 \times 708 = (T_1 \times 00000000000) + (T_2 \times 1111100000) +$
$\quad (T_3 \times 0111100000) + (T_4 \times 11100000000) +$
$\quad (T_5 \times 0001100000) + (T_6 \times 1000000000),$ $732 = 720 \times 724 = (T_1 \times 00000000000) + (T_2 \times 0000011111) +$
$\quad (T_3 \times 0000001111) + (T_4 \times 0000011100) +$
$\quad (T_5 \times 0000000011) + (T_6 \times 0000010000),$ and the differential output is represented by $$686 = 730 - 732 = (T1 \times \underline{\quad\quad})_{HHH} +$$
$$(T2 \times {}^{HHHHH}_{LLLLL}) + (T3 \times \_^{HHHHH} -_{LLLL}) +$$
$$(T4 \times {}^{HHH} -_{LLL} -) + (T5 \times -^{HH} -_{LL}) + (T6 \times {}^{H} -_{L} -)$$

where "+" represents the Boolean OR operator, "x" represents the Boolean AND operator, represents logical inversion (the Boolean NOT operator), A1 through A10 are the steps of primary sequencer 622, B1 through B10 are the steps of secondary sequencer 700, $T_1$ through $T_6$ are the primary timing intervals, "1" represents a logic high, "0" represents a logic low, "$^H$" and "$_L$" indicate differential voltages or currents of opposite polarities, "–" indicates zero differential voltage or current, and a series of ten symbols from the set "$^H$", "–" and "$_L$" represents the secondary cycle under various conditions. The final expression for signal 686 thus clearly shows the decreasing duty cycle and alternating opposite polarities of the output pulses in each successive primary interval.

As an alternative to the implementation of the sixth embodiment as shown using individual gates 660, 662, 702, 704, 706a and b, 708 if needed, 710, 712, 714, 716, 720, 724, 730 and 732, the same functions might more conveniently be implemented using a programmable gate array (PGA) or other programmable array logic (PAL) device, following the Boolean expressions just given. As another alternative, as suggested in FIG. 22 and the accompanying text, some or all of these functions might be implemented using a microprocessor or a microcontroller.

The lower rows in FIG. 34 illustrate composite signals 720, 730, 732 and 686, each taken over one complete primary cycle. The primary time intervals shown are the same as in FIG. 30. Note the close resemblance between trace 610 and trace 686 in these two Figures.

For clarity, just as in FIG. 30, only three secondary cycles are shown in each of traces 720, 730, 732 and 686 for each step of sequencer 622. In a real application, however, several hundred or several thousand secondary cycles might more typically occur during each such step.

Another important feature of the invention is its potentially very compact size and low cost. Since only a small number of active and passive components are needed in each of the embodiments described above, or in others of similar nature within the scope of the invention, and since most (if not all) of the components needed for a specific implementation are available in compact surface-mount packages, it is not difficult to design, for any such implementation, a compact, double-sided printed circuit board and a small, lightweight housing to contain this board and the battery. Such a housing is preferably made from molded plastic or a similar material, preferably with a pocket clip or other means for convenient mounting to a bandage, cast, wrist or other band, article of clothing, container of conductive liquid, or the like. More preferably, the housing is no larger than necessary to hold the described devices and the circuit board or boards which bear them. For typical implementations such as the first four specific embodiments described, suitable housings need be no larger than approximately 5 cm×6 cm×2 cm (about 2.0"×2.5"×0.75") or thereabouts, and in some cases may be significantly smaller. For implementations requiring higher output power, like the last two embodiments, housings may need to be somewhat larger.

Since in a typical implementation the circuit board and housing are small, and since only widely-available, off-the-shelf electronic components are used, manufacturing costs will also typically be quite low. For applications wherein the treatment is slightly more complicated, where for example, more precise delivery of stimulation is required and/or where more delicate adjustment of signals is necessary, a technician or physician may employ an in-house industrial version of this invention for use on patients.

An apparatus according to the invention is therefore lightweight, compact, self-contained, cost-effective to manufacture and maintain, convenient to carry or wear for extended periods, and able to generate the signals just described and deliver them efficiently through conductive means as previously defined and as illustrated, for example, in FIGS. 17 through 20. Power is furnished by compact and inexpensive batteries, typically needing replacement only once in several weeks of use. Since only low voltages and currents are used and there is no connection to the electric mains, the apparatus does not pose a shock hazard even in case of malfunction, and thus is safe for unsupervised home use without any need for special training.

Preferred Embodiments

In a preferred embodiment the present invention comprises an apparatus for generating an electrical signal for use in biomedical applications, said electrical signal comprising: (a) at least four relatively longer primary timing intervals $T_1$, $T_2$, $T_3$, $T_4$ and others if present, forming in succession a repeating primary cycle, said primary cycle having a frequency; (b) at least two relatively shorter secondary timing intervals $t_1$, $t_2$ and so forth, into which at least one of said primary timing intervals is divided and which form in succession a repeating secondary cycle throughout its length, said secondary cycle having a frequency, said frequency lying below 200 kHz; while at least one other of said primary timing intervals is not so divided; (c) a plurality of substantially constant voltage or current levels $L_1$, $L_2$ and so forth; (d) selection of one of said voltage or current levels during each of said secondary intervals within a said primary interval which is so divided, or during the whole of said primary interval if it is not so divided: said levels, selected in succession throughout the course of said primary cycle, thereby forming said electrical signal; and (e) further selection of one or more of said primary intervals, said intervals being not so divided, as one or more equalizing pulses for the establishment of substantial charge balance throughout the course of any one repetition of said primary cycle.

In an alternatively preferred embodiment, the present invention comprises a method for generating an electrical signal for use in biomedical applications, said method comprising: (a) generating at least four relatively longer primary timing intervals T1, T2, T3, T4 and others if present, forming in succession a repeating primary cycle, said primary cycle having a frequency; (b) generating at least two relatively shorter secondary timing intervals t1, t2 and so forth, into which at least one of said primary timing intervals is divided and which form in succession a repeating secondary cycle throughout its length, said secondary cycle having a frequency, said frequency lying below 200 kHz; while at least one other of said primary timing intervals is not so divided; (c) generating a plurality of substantially constant voltage or current levels L1, L2 and so forth; (d) selecting one of said voltage or current levels during each of said secondary intervals within a said primary interval which is so divided, or during the whole of said primary interval if it is not so divided: said levels, selected in succession throughout the course of said primary cycle, thereby forming said electrical signal; and (e) further selecting one or more of said primary intervals, said intervals being not so divided, as one or more equalizing pulses for the establishment of substantial charge balance throughout the course of any one repetition of said primary cycle.

In an additionally preferred embodiment, the present invention comprises an apparatus for generating an electrical signal comprising: means for generating primary timing intervals and secondary timing intervals into which at least one primary timing interval is divided, said primary timing intervals forming a charge balanced primary cycle.

Application of the Apparatus of the Present Invention

By using the apparatus of the present invention as described herein, the apparatus is effective in relieving chronic, intractable pain, acute post-traumatic pain, pain resulting from nerve irritation, pain resulting from diabetic neuropathy, pain resulting from muscle spasms, and pain resulting from compressed nerves. Clearly, a benefit of the present invention is the reduced requirement for pain relief drugs.

In addition the apparatus and methods of the present invention can reduce general swelling, accelerate the resolution of unwanted inflammation, accelerate the healing of spinal disk injuries, relax muscle spasms, maintain or increase the range of motion of arms and/or legs, and be used as an immediate post-surgical stimulation of muscles to prevent venous thrombosis.

The present invention is also effective in treating and accelerating the healing of wounds, including, but not limited to, traumatic wounds, surgical incisions, burns, chronic wounds, including, but not limited to, diabetic ulcers, venous ulcers, arterial ulcers, decubitus ulcers. The present invention is effective in accelerating the healing of strained or torn ligaments or tendons, accelerating the healing of torn muscle tissue. The present invention is also effective in preventing or retarding muscle atrophy due to disuse or prolonged bed rest. The present invention is also useful in regenerating damaged nerves.

The present invention is especially useful in increasing the survival of skin grafts and hair plugs. The present invention is effective in improving the incorporation of synthetic implants such as bone powder and prostheses such as artificial joints (e.g., knees and hips). The present invention is useful in treating sprained ankles, torn knee ligaments, sciatica, back muscle spasm, torn rotator cuff, tennis elbow, carpal tunnel syndrome, ulnar nerve syndrome, temporomandibular joint syndrome and pain from abscessed teeth.

The present invention can be used transcranially to relieve insomnia, depression, anxiety and to promote relaxation and mental alertness.

The present invention is useful in promoting angiogenesis including, but not limited to, increasing local blood circulation, increasing blood flow to areas of traumatic injury, increasing blood flow to areas of chronic skin ulcers. The present invention is also useful in modulating blood coagulation.

While not wanting to be bound by the following hypothesis, the apparatus is believed to operate directly at the treatment site by enhancing the release of chemical factors such as cytokines which are involved in cellular responses to various physiological conditions. This results in increased blood flow and inhibits further inflammation at the treatment site, thereby enhancing the body's inherent healing processes.

The present invention is especially used in accelerating healing of simple or complex bone fractures including, but not limited to, bones sawed or broken during surgery. The present invention can be used to promote fusion of vertebrae after spinal fusion surgery.

One of the areas where the present invention can also be used is to accelerate the healing of damaged or torn cartilage. Also, the present invention can be used to accelerate the healing (epithelialization) of skin wounds or ulcers.

The following conditions provide a representative listing of conditions and ailments for which the present invention may be useful: relief of chronic intractable pain, relief of acute posttraumatic or postsurgical pain, reduction of pain resulting from nerve irritation (hyperalgesia), reduction of pain resulting from diabetic neuropathy, reduction of pain resulting from muscle spasm, reduction of pain resulting from trapped or compressed nerves, reduction of requirement for pain relief drugs, reduction of swelling, acceleration of resolution of inflammation, acceleration of healing of spinal disk injuries relaxation of muscle spasms, muscle re-education, maintain or increase range of motion, immediate post-surgical stimulation of calf muscles to prevent venous thrombosis, acceleration of healing of traumatic wounds, acceleration of healing of surgical incisions, acceleration of healing of burns acceleration of healing of chronic wounds (diabetic, venous, arterial and decubitus ulcers), acceleration of healing of strained or torn ligaments, acceleration of healing of strained or torn tendons, acceleration of healing of torn muscle tissue, prevention or retardation of disuse atrophy, retardation of or reversal of muscle atrophy in prolonged bed rest, and retardation of or reversal of muscle atrophy in microgravity and acceleration of regeneration of damaged nerves.

Additional applications of the present invention result in the acceleration of healing of fresh, simple bone fractures, of complex (multiple or comminuted) bone fractures, of bones sawn or broken during surgery and fusion of vertebrae after spinal fusion surgery. The present invention may be used to treat nonunion fractures; treat, prevent or reverse osteoporosis; treat, prevent or reverse osteopenia; treat, prevent or reverse osteonecrosis; retard or reverse formation of woven bone (callus, bone spurs), retard or reverse bone calcium loss in prolonged bed rest, retard or reverse bone calcium loss in microgravity. In addition, the present invention may be used to increase local blood circulation, increase blood flow to areas of traumatic injury, increase blood flow to areas of chronic skin ulcers and to modulate blood clotting.

The present invention may also be used for the adjunctive treatment of tendonitis, modulate local immune system response, modulate systemic immune system response, adjunctive treatment of autoimmune diseases (e.g. rheumatoid arthritis) and adjunctive treatment of cancer.

The present invention may further be used to treat plantar fasciitis, sprained ankles, torn knee ligaments, sciatica, treat back muscle spasm, treat torn rotator cuff, treat tennis elbow, treat carpal tunnel syndrome, treat ulnar nerve syndrome, treat ternporomandibular joint syndrome, relieve pain from an abscessed tooth, accelerate growth of cultured cells or tissues, modulate cell proliferation, modulate cell differentiation, modulate cell cycle progression, modulate the expression of transforming growth factors, modulate the expression of bone morphogenetic proteins, modulate the expression of cartilage growth factors, modulate the expression of insulin-like growth factors, modulate the expression of fibroblast growth factors, modulate the expression of tumor necrosis factors, modulate the expression of interleukines and modulate the expression of cytokines.

The present invention may also be used to retard blood and other bioproduct deterioration on storage, devitalize selected pathogens in the human or animal body, devitalize selected pathogens in isolated tissue or cell cultures, devitalize selected pathogens in blood and other bioproducts and devitalize selected pathogens in foods, beverage or other materials.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

As used in the following Examples, the MedRelief device refers to an electrostimulator as described above for generating an electrical signal that is substantially as shown in FIG. 6.

EXAMPLE 1

Bioelectrical Stimulation of Fractured Bones

A 50 year old male was injured in a motorcycle accident that resulted in spiral fractures of his tibia and fibula. The tibia was fractured approximately 3" above the article while the fibula was fractured from the top of the bone. At the time of the accident the male was in otherwise good health and sustained no other injuries. X-rays and the evaluation in the emergency room confirmed the double fractures. It was determined that surgery to correct the problem would be required. An appointment was set for the following morning with the orthopedic surgeon. Surgery was scheduled and performed the afternoon of February 4. A sterile steel nail was inserted down the shaft of the tibia running the full length of the bone. Two screws secured the nail at the top of the tibia while three screws secured it at the ankle. The patient was originally scheduled for two nights in the hospital but was released approximately 24 hours following the surgery. Before release the patient was fitted with a cast walker boot for protection along with crutches and advised that he was to be non-weight bearing on the injured leg. A one week follow-up appointment was made with the surgeon. The patient returned home to rest. He was given Percocet pain relievers for pain management, taking them every four hours.

By February 7th the patient was experiencing an increase in pain and an elevated temperature. The surgeon prompted treatment with antibiotics for probable injection. Within 24 hours of the start of antibiotics there was a decrease in the pain level as well as a return to normal body temperature.

February 11 was the one week follow-up appointment with the surgeon. X-ray showed that the bone alignment was good and everything was properly aligned and in position. The patient was advised at that time that he would have to remain non-weight bearing on the leg for 10–12 weeks. Application of the novel waveform of the present invention (substantially as shown in FIG. 6 and generated by an electrostimulator), began on February 12. The electrodes were placed on each side (lateral and medial) of the leg at the point of fracture on the tibia. The unit was used in one hour periods, three times a day. scheduled was established with the first treatment starting at 8 AM, the second at 2 PM and the third treatment at 8 PM. This treatment schedule was closely followed throughout the entire recovery period. The patient applied the electrodes to his leg first thing in the morning and left them in place all day. After two weeks of use the skin at the electrode sights became somewhat sensitive. Speculation is this sensitivity this was caused by the adhesives on the reusable electrodes. The patient started to alternate placement of the electrodes from lateral/medial to anterior/posterior and this eliminated the skin sensitivity. Within several days the patient noticed a decrease in pain to the point he discontinued all pain medication. No pain medication was taken after February 15. The patient discovered that by using the present invention for 10–15 minutes when pain occurred, it would quickly disappear. However, use for this purpose would only happen three or four times a week for the first several weeks then regressed to one to two times a week up through week eight. After that point, treatment was not needed for pain reduction.

On March 9 the patient returned to the doctor for a six week follow-up. New X-rays revealed all bones were in position and significant healing occurred. At that point the surgeon estimated healing to be two to three weeks ahead of schedule and allowed the patient to start very limited partial weight bearing. A follow-up visit was scheduled for ten weeks post-op. The patient continued to follow the treatment regimen established earlier. Weight bearing was limited to light walking with crutches for short distances, it should be noted that the patient followed a normal, healthy diet which included his normal daily multivitamin. No supplements were taken to increase his calcium intake.

June 3 was the last visit with the surgeon. The patient was seventeen weeks post-op at this point. The surgeon signed off on the patient at this point. The surgeon's reaction was that the patient had healed as quickly as anyone he had seen and much faster than he expected for a 50 year old man. The patient was told to gradually increase his activity level as he felt comfortable. As the summer progressed, the patient increased his activities until he was almost at his normal, pre-injury level.

On October 6, 35 weeks post-op the patient made an abrupt turn barefoot on carpet and felt a snap from the ankle on the injured leg. It became very sore, swollen and difficult to walk on. A trip to the surgeon could not find anything definitive so the patient was told to treat it like sprain and take it easy. On October 20 the patient again experienced the same "snap" in the ankle followed by pain and swelling. At this point the surgeon suggested removal of he screws from the ankle to which the patient agreed. The three screws were removed from the patient's ankle on November 3.

Following the screw removal, there was some minor pain along with swelling. The patient was instructed to take it easy for four to five weeks while the screw hole filled in with bone. The patient again applied the novel waveform according to the present invention (FIGS. 6 and 7) three times per day, as done originally. At the four week follow-up the screw holes were virtually filled in, the soreness and swelling were gone and the patient was released from care.

EXAMPLE 2

Bioelectrical Stimulation of Fractured Bone in Animal

An injured German-Shepherd mix was successfully treated through bioelectrical stimulation using the waveform substantially as shown in FIG. 6 as detailed below.

It was found that a bullet had struck the dog in her right front femur and shattered its middle section into many small pieces. The bullet appeared to be 0.22 caliber, and had mushroomed on impact, then fragmented further, with many lead pieces clearly visible on an X-ray.

Under anesthesia a half shell, fiberglass Spica splint was placed with heavy cast padding. The predicted recovery time was at least four and more likely six weeks or more. The veterinarian warned that the dog would probably have a permanent limp. No attempt was made to remove the bullet.

An X-ray after two weeks of MedRelief™ treatment showed the bone fragments completely reunited, now encasing the major bullet fragments. The fracture already showed excellent callus and stabilization. Bioelectrical stimulation was terminated and the cast was removed—after only one-half the expected time—and the dog came home, still wearing the collar and a leg bandage, to finish her recovery.

About a week later it was noticed that she was using the leg again, at first hesitantly and then more often. In two months she was walking and running normally, with no sign of a limp.

EXAMPLE 3

Bioelectrical Stimulation of Deep Skin Abrasions

The subject of this study had suffered three abrasive injuries on the backs of his hands. The wounds were received at the same time, in the same way, and were of about the same severity. Of the three wounds, the one that was the most severe was selected for the MedRelief™ treatment, bioelectrical stimulation comprising application of the waveform substantially as shown in FIG. 6.

The wounds were cleaned of visible debris using soap and water, but no antibiotics or disinfectants were used. Treatment was for about eight hours at a time, during sleep.

After the first night all of the wounds were scabbed over, the areas around them swollen and painful to the touch, but the treated one was noticeably worse than the others. (It is impossible to say whether this resulted in part from the action of MedRelief™, or simply from that wound's having been more severe in the first place.) The pain and sensitivity of the treated area gradually lessened through the day, though, and by evening the three wounds all seemed about the same. The treatment was repeated in the same way for a second night.

The next morning the untreated wounds were still quite painful and were surrounded by inflammation. Surprisingly, though, the treated wound was now painless, very noticeably less inflamed than the others, and after a few hours of drying the scab began to flake off, revealing thin, pink new skin. Touching this with a probe gave a sense of pressure, but no pain.

No further MedRelief™ treatment was used. After the second morning, there was never any pain from the treated wound; the new skin grew gradually thicker, and in about a week the area looked as if it had never been injured. In contrast, the untreated wounds remained painful and scabbed for several more days, and took an additional week for complete healing. None of the three, however, left noticeable scars.

Figure 2:
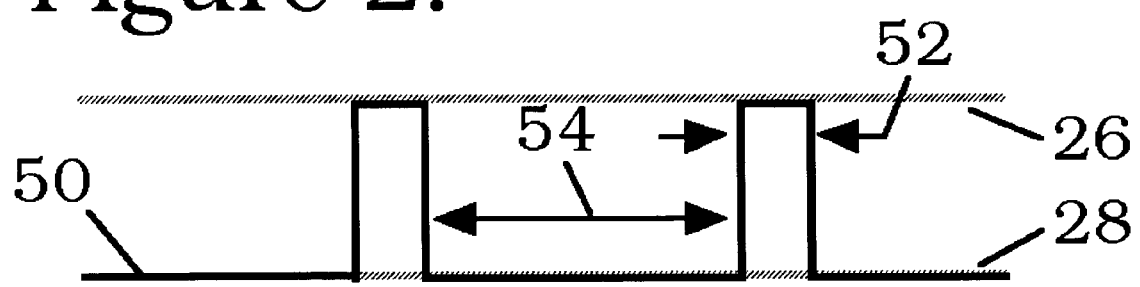
FIG. 2 illustrates a waveform used in the treatment of osteoporosis. (Prior Art)

Reference to a medical textbook (Patrick, Woods, Craven, Rokosky and Bruno, *Medical-Surgical Nursing—Pathophysiological Concepts* (1986), FIGS. 15-2 through 15-4 and accompanying text) suggested a roughly fourfold increase in the early healing stages under MedRelief™ treatment, with the inflammatory, cell movement and proliferation, and collagen framework reconstruction stages of healing all substantially complete in about two days where typically eight to ten would be required. It may be noted that the untreated wounds followed the "typical" schedule.

EXAMPLE 4

Bioelectrical Stimulation for Alleviation of Pain and Healing Stimulation of Knee Ligament The subject of this study suffered a strained knee ligament, which has since been subject to re-injury, with approximately the same progression of symptoms each time. Following each re-injury the knee becomes progressively more stiff, inflamed and painful over the course of two to three days, and then gradually seems to heal, with some pain persisting for about two more weeks.

After the most recent injury, the MedRelief™ device was applied. More specifically, the novel waveform of the present invention as substantially as shown in FIG. 6 was applied through the use of electrodes placed on the skin. A single overnight treatment during sleep took away most of the pain and stiffness, and by noon after a second overnight treatment, the knee was entirely pain-free.

EXAMPLE 5

Bioelectrical Stimulation for Alleviation of Pain Associated with Carpal Tunnel Syndrome As a result of some heavy lifting, the subject started to experience severe pain and discomfort in his right wrist: flexing or tapping it, or grasping anything using the little and ring fingers, brought severe, sharp pain in the base of the hand, radiating into these fingers. This pain grew steadily worse over the following five days. Although the subject had had similar pain in the same area several times in years past, it had never been this bad or this long lasting.

Five days later an official diagnosis of carpal tunnel syndrome was made. Carpal tunnel syndrome is a chronic condition in which injured tendons swell and pinch nerves in the wrist; the pain causes arm muscles to tense, further injuring the tendons, and so forth. Once this cycle is set up, it usually lasts a lifetime. Either of the two main wrist nerves, or both, may be involved; in the subject's case it was the ulnar nerve. This form of the condition is often called "ulnar nerve syndrome."

On the evening after diagnosis was made, the subject started the MedRelief™ treatment (comprising the application of the waveform depicted substantially as shown in FIG. 6), placing one electrode pad on the edge of the affected hand and the other near the elbow so as to include the tensed muscles as well as their tendons in the current path. Treatment began at bedtime and continued through the night and the following morning.

The next morning the pain was much reduced, and by early afternoon it was nearly gone, so the subject removed the unit and pads. The symptoms returned that evening though, so the subject resumed nightly treatment again during sleep. After two more such treatments he was pain-free, and remained so without any further treatment.

The subject injured the hand again five months later, with all symptoms just as before. This time, though, the subject used MedRelief™ the first night after the pain appeared, and halfway through the following day the pain was gone again. That time, it did not return; one night was enough.

EXAMPLE 6

Bioelectrical Stimulation for Alleviation of Radial Nerve Syndrome

The subject is a professional massage therapist whose work often requires her to apply a lot of pressure with her hands to help relax tensed muscles. Hence, she also does resistance training to help keep her arm muscles strong.

After using an unfamiliar weight machine for the first time as part of her workout, the subject noticed tenderness in her left wrist. Over the next several days the wrist became progressively more swollen, stiff and painful, while the brachioradialis muscle also became chronically tensed and sore. As a result, she was forced to cancel several days of work.

The type and location of pain and swelling led to a diagnosis of radial nerve syndrome, an inflammatory condition that usually leads to compression neuropathy. The condition is progressive and in many cases treatment requires surgery, although this often fails to restore normal functioning or fully relieve the pain.

The subject decided to try MedRelief™ (comprising the application of the waveform substantially as shown in FIG. 6), beginning with one overnight treatment. Within three hours, the muscle pain was gone and her wrist pain was also quite noticeably lessened. By morning even the wrist pain was nearly gone, while the swelling was also much reduced. As a result, she was able to administer three massages that day.

The subject continued MedRelief™ treatment for two more days, twenty-four hours a day. By the end of that time her wrist was completely normal again, and since then she has had no more trouble with it.

EXAMPLE 7

Bioelectrical Stimulation for Alleviation of Pain and Swellingfrom Reinjury of Damaged Knee Ligaments About thirty years ago, the subject of this study suffered severe knee ligament injuries in an automobile accident, including complete severing of the medial ligament. Since then, the knee has been very prone to reinjury, several times swelling to the size of a soccer ball and requiring surgical draining.

Two years ago an orthopedic doctor recommended total knee replacement surgery to try to repair the damage, but the subject was unwilling to undergo this. Instead, the subject experimented with MedRelief™ applying bioelectrical stimulation substantially as shown in FIG. 6.

She stated that within minutes of her placing the device on her knee, "the pain vanished," and that after two weeks of wearing it, the swelling had gone down enough to let her resume normal activities.

EXAMPLE 8

Bioelectrical Stimulation for Alleviation of Pain from Torn Joint Cartilage

The patient has suffered for many years from a torn medial meniscus (cartilage pad) in one knee, resulting in moderate to severe pain when the knee is bent, especially with a load on it as when walking down stairs.

The patient tried a MedRelief unit (comprising the application of the waveform substantially as shown in FIG. 6), with one electrode placed on the back of the thigh, 3" above the knee and the other on the front, 2" beneath the patella. Within a few minutes he reported a decrease in pain, and stated, "After 45 minutes I felt no pain. For a week after using it there was almost no pain, and now, after 2 weeks, it is still improved over my normal state."

EXAMPLE 9

Bioelectrical Stimulation for Alleviation of Pain from Torn Anterior Cruciate Ligament The patient was using an unfamiliar exercise machine at a health club when she felt sudden pain in the front of one knee. The pain grew steadily worse through the following several weeks, exacerbated by her job conditions (she is a hospital nurse) which required long periods of standing and much walking around. "It got so bad that it was hard to sleep because of it." The pain was diagnosed as resulting mainly from a torn anterior cruciate ligament.

The patient began using MedRelief™ (comprising the application of the waveform substantially as shown in FIG. 6), at night, during sleep. The patient stated: "I could tell it was working because the pain stopped waking me up at night. My pain [on a 0–10 scale, 10 being worst] went from about a seven or eight, down to about a one. Pain still comes back toward the end of a long day, but seldom so bad as before, and after a night of treatment it's usually almost gone again."

EXAMPLE 10

Bioelectrical Stimulation for Alleviation of Pain from Misaligned Vertebrae/Pinched Spinal Nerves The patient has experienced severe lower back pain on previous occasions, typically on awakening following a day of golf or a long drive in his compact car. The pain has responded well to chiropractic manipulation, indicating vertebral misalignment.

On a recent occasion the patient had spent two days golfing, followed by a business trip for which he had to drive four hours each way in a compact car. He awoke the following morning in very severe pain that he rated at 10 ("worst imaginable") on the standard 0-10 scale. Unfortunately, it was the Saturday of a long weekend and the chiropractor's office was closed, not to reopen until the following Tuesday.

The patient tried a MedRelief™ unit, placing electrodes for generating the waveform substantially as shown in FIG. 6, and continued treatment throughout that day and the two days following. He reported, "I could still feel the pain, but the treatment took it down from 10 to 2 or 3, so I could get through the weekend until I could see the chiropractor again."

EXAMPLE 11

Bioelectrical Stimulation for Alleviation of Pain from Abscessed Tooth

On a Friday the patient experienced a severe toothache from a tooth in the upper left side of his mouth, but quickly discovered it was too late to get to a dentist before the coming Monday.

The patient tried MedRelief™, placing an electrode just to the left of his nose and a second electrode under his jaw, just to the left of the windpipe. Stimulation was applied with some caution, due to the usual warnings placed on electro-stimulation devices not to apply them in the head or throat areas. No adverse effects were noted, however, and after about 45 minutes' treatment, the pain was relieved. It returned periodically, but further treatments of 30 to 45 minutes each time, applied in the same way, sufficed for relief. Treatment was continued through Friday, Saturday and Sunday.

Upon examination on Monday, the painful tooth was found to be abscessed.

EXAMPLE 12

Bioelectrical Stimulation for Alleviation of Wrist Pain Due to Repetitive Motion Injury The subject of this study was a secretary and began experiencing severe right wrist pain. Fearing it was the beginning of carpal tunnel, and after over the counter pain relievers had only helped temporarily, she used the invention as described herein. She wore the MedRelief™ unit (enabling the application of the waveform substantially as shown in FIG. 6), on her right wrist continuously for two days and then reported: "The pain began to go away within an hour of use and I only continued to wear the unit to make sure all inflammation was completely healed. I have not had any pain in my wrist in over six months."

EXAMPLE 13

In Vitro Evaluation of Bioelectrical Signals

The purpose of the following study is to evaluate the influence of the novel bioelectrical signals described herein on cartilage tissue.

Description

Cartilage explants were prepared from fresh pig knee joints obtained from a commercial slaughterhouse. Cartilage tissue was removed from the joint using standard dissection methods. Several studies have demonstrated that such tissues retain consistent biological and mechanical properties for several days when hydrated at room temperature. When covered by appropriate media and placed in an incubator, these tissues survive for several weeks.

The present test configuration consisted of six-test culture wells (25×75 mm) connected in series via a coiled section of niobium wire. Niobium wire formed a natural coating that prevents release of metal ions from the electrodes. Before the first test chamber and after the last test chamber, there was an electrode well connected via niobium wire that effectively served to uniformly disperse the electrical field delivered to the cartilage explant test sample. The cartilage samples were cut to fill approximately 75% of the well area (25×75 mm). The thickness (1½ to 2 mm) of each sample had minor variations based on the specific animal and anatomic location of the sample. In all cases, the tissues were completely covered by medium.

Two types of cartilage tissue were used for these experiments. Normal cartilage (NCart) was prepared as above and placed into test wells with no further preliminary treatment. Degenerated cartilage (DCart) was prepared by treating the normal cartilage for 48 hrs with IL-1 to degrade the tissue to simulate changes observed in osteoarthritic cartilage. After 48 hours, the cartilage samples and the media were tested for the outcome variables above.

The outcome variables include production of proteoglycan and cartilage, release of proteoglycan, release of prostaglandin and release of nitric oxide. The first three variables are measures of cartilage metabolism, and the latter two variables are measures of inflammation.

Design:

NCart was placed in each well of the six well system described above and treated with a MedRelief™ device with output current reduced, using external resistors, to establish a current density in the treated tissue of about 5 to 7 microamperes per square centimeter. Treatment was for 2 hours twice each day for 2 days. The control for this experiment was the same test configuration, but the MedRelief device was turned off.

In a similar manner, the experiment for NCart was repeated for DCart.

EXAMPLE 14

In Vivo Evaluation of Bioelectrical Signals

The purpose of the following study is to evaluate the influence of the novel bioelectrical signals described herein on full-thickness wounds in a pig model.

Description

The experimental animals (N=8) are the Yorkshire farm pigs, which have skin properties (highly vascular, tight skin) similar to humans. Eight (8) one inch square; uniformly distributed, full-thickness wounds are created on the back of each pig under anesthesia. Essentially, there are four rows of two wounds starting below the shoulders and moving downwards towards the base of the spine. All animals receive appropriate pain relief post-surgery. All wounds are filled with hydrogel and covered with a Tegaderm dressing. Additional protective materials are applied to protect wounds and keep them clean. Wound dressings are changed daily. Care is used to assure a gentle wound cleaning to provide appropriate clinical care, yet give minimal disruption to the healing wound site.

Wounds (8 per animal) are placed so that the centerline between square-shaped wounds is about 5 inches apart from top to bottom and about 4 inches apart from side to side. A template is created to assure that wound location is uniform.

The study endpoints are 10 and 21 days. At the sacrifice endpoints, two large excisional tissue samples made completely through each wound will be collected for histological processing. It would not be safe for the animal to conduct these tissue harvests at 10 days and then have the animal survive for an additional 11 days; therefore, four original full-thickness wounds are created on day 1 and four wounds will be created on day 11, so that the animal will be sacrificed at 21 days and contain wound repairs lasting for both 10 and 21 days. Several histomorphometric and immunological staining tests will be performed on these tissue samples.

Every second day following wound creation until the time of sacrifice, each animal has the following evaluations: scoring by a blinded assessor on a wound healing scale of 1 to 4, photographing of wounds, and assessing Laser Doppler Perfusion. The laser study consists of a series of test points surrounding each wound and using a Moor device.

Self-adherent, flexible, conductive electrode placement is such that each electrode pair stimulates the two wounds on each row (from top to bottom). This is accomplished by placing the electrodes centerline about two inches outside of each electrode on a row. The electrical current flowing between electrodes stimulates both wounds at the same time. Electrodes are placed on each pig only while they are in a restraining sling twice each day.

Design: (this may change to two TXs)

There are three treatments (TXs) that can be studied. Each TX is applied to the eight wounds of two pigs. Therefore, there are 16 wound sites for each TX. Eight (8) of these samples are for sacrifice time 10 days, and 8 are for sacrifice time 21 days. In addition two control pigs similarly have 8 wound sites each with an inactive electrode.

Electricity (or control) will be applied twice each day (BID). The following device settings and durations will be used:

TX1=intensity setting low ($\approx$5–9 mv/cm)–duration 15 minutes for each treatment TX2=intensity setting low ($\approx$5–9 mv/cm)–duration 60 minutes for each treatment TX3=intensity setting low plus resistor ($\approx$1–3 mv/cm)–duration 15 minutes for each treatment During the surgical creation of the wound, two trial electrodes are placed on the outside of the two wounds on a row, so that the delivered current (mv/cm) can be measured. This provides confidence that the treatment bioelectrical currents delivered are as anticipated. No further current testing will be conducted during the healing process because it would disrupt the process.

EXAMPLE 15

Fresh Fracture Healing

The purpose of the following study is to evaluate the influence of the novel bioelectrical signals described herein on a mid-shaft radius defect in a rabbit model.

Description

In the rabbit, the ulna has a diameter similar to or larger than the radius. Also, these bones are bridged by a tough interosseous membrane. Therefore, a 1 cm gap in the radius does not lead to mechanical instability. A rabbit can withstand such a bilateral procedure (one treatment and one control side) and thrive. A 1 cm gap in the radius will heal naturally beginning to show signs of healing in about 6 to 8 weeks.

The anesthetized, experimental rabbits (N=20) have the radius exposed and a 1 cm gap created with an oscillating bone saw. The wound site is closed and soft tissue sutured in place. Appropriate pain medication is provided.

Self-adherent, flexible, conductive electrodes are placed diametrically opposed at the wound site such that one electrode is anterior and one posterior across the bone diameter. On a weekly basis, X-rays are taken to observe general rate of healing. On sacrifice, each forelimb is evaluated by Faxitron imaging and biomechanical testing to failure in torsion. The electrodes are placed on both forelimbs twice each day during the post-operative study period. The rabbits are placed in bunny restraints and not anesthetized each time.

We anticipate significant bone fracture healing may be present in the treated animals at 4 to 6 weeks post-surgery. There are two treatments (TXs) studied. For each TX, if the X-rays for 6 or more active treated animals show significant bony bridging and callus formation, then that TX may be stopped as early as 4 or 5 weeks. In any event, the animals in both TXs are sacrificed at 6 weeks at the latest.

Design

There are two treatments (TXs) that can be studied. Each rabbit acts as its own control because of the bilateral procedure. Each TX will be applied to ten (10) rabbits.

Electricity (or control) will be applied twice each day (BID). The following device settings and durations will be used:

TX1=intensity setting low plus resistor ($\approx$4–10 mv/cm) with duration of 30 minutes TX2=intensity setting low plus resistor ($\approx$4–10 mv/cm) with duration of 120 minutes Twice a day, animals are removed from the home cage and placed in a soft restraint device. The forelimbs are pulled through holes in the restraint and the electrodes are placed. The treated limb receives the stimulation for either approximately 30 minutes or 120 minutes. The control limb has similar electrodes placed on the skin, but is not be stimulated. During the stimulation period, animals are continuously restrained for up to 120 minutes. This is considered the least invasive method for exposing the animals to the stimulation.

EXAMPLE 16

Evaluation of the Med Relief™ Stimulator in a Wound Healing Model in the Pig Objective The purpose of this study is to evaluate the effects the test device on wound healing in the pig.

This study involves the use of Landrace-Duroc cross (farm pig) obtained from Bailey Terra Nova, Schoolcraft, Mich. The test animals are at least 10 weeks of age at arrival and weigh approximately 25 to 35 kg at study initiation. Animals selected for this study are as uniform in age and weight as possible. After a physical examination is conducted to select suitable animals for assignment to study, the animals are randomized into treatment groups using a simple randomization.

| | | | Study Design | | | |
|---|---|---|---|---|---|---|
| | Treatment | | Number of Animals | | | |
| Group | Stimulation (mV/cm)[a] | Duration (min) | Surgery Day 0[b] | Number of Sites[c] | Surgery Day 11[b] | Number of Sites[c] | Necropsy Day 21 |
| 1 | 0 | 0 | 2 | 4 | 2 | 4 | 2 |
| 2 | Low (5–9) | 60 | 2 | 4 | 2 | 4 | 2 |

-continued

Study Design

| | Treatment | | Number of Animals | | | | |
|---|---|---|---|---|---|---|---|
| Group | Stimulation (mV/cm)[a] | Duration (min) | Surgery Day 0[b] | Number of Sites[c] | Surgery Day 11[b] | Number of Sites[c] | Necropsy Day 21 |
| 3 | Low (5–9) | 15 | 2 | 4 | 2 | 4 | 2 |
| 4 | Low + (1–3) | 15 | 2 | 4 | 2 | 4 | 2 |

[a]The electrodes are placed lateral to each set of two wound twice per day for the duration indicated. The electrodes are connected to the test device and the device is set as follows: Mode - Pulse, Modulation - High, and Intensity - Low. This setting delivers a pulsed stimulation between 5 and 9 mV/cm. Animals in Group 4 are set up in a similar manner except that the leads have an in-line resistor designed to reduce the level of intensity to 1–3 mV/cm.
[b]Animals undergo a surgical procedure on Day 0 and Day 11 to evaluate the effects of the stimulation produced by the test device on both the acute, inflammatory stage and the longer term remodeling stage of wound healing. On Day 0 and Day 11, 4 wounds are created on the back of each animal. Wounds are paired laterally for the purpose of stimulation with the test device.
[c]Sets of paired sites are randomized within each treatment group. A map of the treatment sites is created for each animal and included in the study data.

Preparation of Animals

Preoperative Procedures

Animals are fasted overnight the day prior to surgery. On the day of surgery, general anesthesia is induced using the drugs listed in Table 1. Telazol or a ketamine/xylazine cocktail may be used to induce anesthesia, the sedative used is documented. Anesthesia is maintained using a semiclosed circuit of isoflurane. Assisted ventilation will be accomplished with a ventilator.

Surgical Procedures

On Day 0, the surgical site on the dorsal right side is prepared by clipping the hair and cleansing the site with iodine scrub alternating with 70% isopropyl alcohol and painting with iodine solution. Lactated Ringer's Solution is infused during surgery via a catheter.

Prior to creation of the wounds, the incision sites are marked so that each pair of wounds is approximately the same distance from the spine, and the midline of each wound is approximately 10 cm from it's pair and 12–14 cm from the next set of treatment sites. The wounds are made in the shape of a square with each side being approximately 2.5 cm long. The incisions are full thickness and the tissue at the center of the square is removed. The wounds are not closed, but are filled with a conductive hydrogel and covered with Tegaderm and gauze and checked daily for signs of infection. The hydrogel is a product that helps to promote healing protect the wounds as well as act as a conductive agent for the stimuli.

Following surgery, the animals are closely monitored during anesthetic recovery for physiological disturbances including cardiovascular/respiratory depression, hypothermia, and excessive bleeding from the surgical/injection site. Supplemental heat is provided as needed. The endotracheal tube is removed after the animal regains the swallow reflex. The animal is then returned to the study room, where postoperative monitoring continues. Long-term postoperative monitoring includes scoring of surgical sites, changing of the wound dressing daily, and administration of cephalexin (500 mg BID PO) for the duration of the study.

Test Device Implantation

Route of Administration

The electrodes of the test device are placed lateral to each set of paired wounds. The electrodes are placed and the treatment site stimulated twice a day for 42 days.

Stimulation Level and Duration

Group 1—Low intensity (4–10 mV/cm) for approximately 30 minutes

Group 2—Low intensity (4–10 mV/cm) for approximately 60 minutes

Administration of Stimulation

Twice a day, animals are removed from the home cage and placed in a sling restraint. The electrodes are placed lateral to each pair of wounds and attached via the leads to the test device. The test device is activated for the required period of time and the animals may be sedated with Telazol as needed. During the stimulation period, animals are continuously restrained for up to 60 minutes. This is considered the least invasive method for exposing the animals to the stimulation.

Parameters evaluated include: leukocyte count (total and differential), erythrocyte count, hemoglobin, hematocrit, mean corpuscular hemoglobin, mean corpuscular volume, mean corpuscular hemoglobin concentration (calculated), absolute and percent reticulocytes, platelet count, prothrombin time, and activated partial thromboplastin time. Additional parameters evaluated include: alkaline phosphatase, total bilirubin (with direct bilirubin if total bilirubin exceeds 1 mg/dL), aspartate aminotransferase, alanine aminotransferase, gamma glutamyl transferase, sorbitol dehydrogenase, urea nitrogen, creatinine, total protein, albumin, globulin and A/G (albumin/globulin) ratio (calculated), glucose, total cholesterol, electrolytes (sodium, potassium, chloride), calcium and phosphorus.

EXAMPLE 17

In Vivo Experimentation for Evaluation of Bioelectrical Stimulation in Rat Arthritis Model The present study involves investigating the effectiveness of a novel pulse-burst electric signal substantially as described for example in FIG. 6 to treat swelling, dysfunction and pain in a rat model of arthritis.

Arthritis is induced in one ankle joint of a rat using the approach described by Coderre T J, and Wall P D. (Ankle joint arthritis in rats: an alternative animal model of arthritis to that produced by Freund's adjuvant. Pain 1987; 28: 379–393: attached). Animals are placed in a plastic chamber and anesthetized with isoflurane (to effect beginning with 4 MAC and maintenance with 1.25 MAC; MAC=minimum alveolar concentration that prevent rats from making a directed response to a standard noxious stimulus).

Urate crystals are injected into the medial side of the tibio-tarsal joint of the rats while they are anesthetized. The animals are removed from the chamber and kept anesthetized by administering isoflurane in oxygen via a nose cone. A small incision is made over the ankle on the dorsal side of one hind limb, and a needle inserted just medial to the tendon of the tibialis anterior. 0.05 ml volume of 1.5 mg of sodium urate is injected through a 21-gauge needle with its tip bevelled to 45 degree. Following the injection, the skin is closed with a single suture. Thereafter, twice a day and for about two hours each time throughout the duration of the study, the animal is anesthetized. Both hind legs are shaven. The ankle circumference is then measured on each leg. Following measurement, a self-adhesive electrode is placed on the ankle injected with urate and on the injected hip. In one half of the rats, a pulse-burst electric signal is applied at a subthreshold intensity for human sensation between the electrodes on the injected side for two hours, producing a current density of approximately 10 microamperes RMS per square centimeter. Following stimulation, the electrodes are removed, the leg is washed to remove any electrode residue, and the measurement is repeated. The rat is then allowed to recover from anesthesia and returned to its cage until the next stimulation session. Additional measurements (see below) are taken immediately before the first stimulation session (6 hours after urate injection) and thereafter at 24, 48, and 72 hours after urate injection.

The following parameters are measured using the technique of Coderre and Wall:

Standing paw pressure
Walking paw pressure
Body weight
Foot withdrawal (50° C. water)
Foot manipulation
Placing reflex
Ankle diameter
Ankle radiograph
Spontaneous activity (1) Standing paw pressure: Rats are taken from their home group cages and placed in a 12" by 12" by 9" plexiglass chamber and observed for a standard period of 5 min. Under the chamber a mirror is set at a 45 degree angle to allow a clear view of the rats' feet. The amount of weight (paw pressure) the rat is willing to put on the hind paw of the injected limb is evaluated and categorized according to the following scale: 0=normal paw pressure, paw is completely on the floor but toes are not spread; 2=moderately reduced paw pressure, foot curled with only some parts of the foot lightly touching the floor; 3=severely reduced paw pressure, foot elevated completely.

(2) Walking paw pressure: Rats are observed in the above described chamber to assess the extent of the limp or alteration of gait produced by the injection of sodium urate in the hind limb. The categories and their weightings are as follows: 0=normal gait; 1=slight limp, visible over-flexion of injected limb; 2=moderate limp, paw of injected hind limb only briefly touches the floor; 3=severe limp, 3-legged gait. In the event that it is not clear which of the two categories the rat will fall into, a score between the two categories is given.

(3) Body weights: Increases or decreases in body weight are assessed over a period of five days in rats with articular injection of either sodium urate or vehicle, and subcutaneous injections of either sodium urate or vehicle.

(4) Foot withdrawal (heat): The rat is hand-held, with its nose over the wrist of the experimenter, and the hind paws on the experimenter's fingertips. The right and left hind paw are lowered between the experimenters finger's and quickly immersed into a beaker of water maintained at 50° C. Time is measured until the rat flicks its paw out of the water, up to a 12 sec cut-off. Foot-withdrawal latency scores are based on an average of 2 tests, with a 5 min interval between tests.

(5) Foot-manipulation: Rats are again hand-held and the foot is gently manipulated by the experimenter. Manipulations include foot flexions and extensions in the normal working range of the ankle joint. Responses are classified as noxious or non-noxious based on the presence or absence of vocalization or movement on manipulation.

(6) Placing reflex: Hand-held rats are slowly moved toward a table so that the dorsal surface of the right or left hind paw just touches the edge of the table. The response is classified as a placing reflex if the rat lifts its paw in such a way as to prepare for supporting the weight of the body on the surface. The test is repeated five times for each hind paw, and scores are based on the number of clear reflexes displayed out of 5 trials.

(7) Ankle diameter: The diameter of the tibio-tarsal joint in the right and left hind limbs is measured using a two-point compass and ruler. The lateral point of the compass is lined up with the talus just below the lateral malleolus of the fibula.

(8) Ankle radiograph: The treated and untreated tibio-tarsal joints of 2 rats are X-rayed before and 24, 48 and 72 hours after urate injection. Radiographs are used to assess the degree of soft tissue swelling as well as any destruction or decreased density of bone surrounding the ankle joint (based on prior study results, none are expected).

EXAMPLE 18

In Vitro Analysis Evaluating Effects of Bioelectrical Stimulation on Osteoclasts This study is designed to test the utility of imbuing osteoblasts with bioelectric signals that enhance bone-specific performance functions.

Human Osteoblast Cells are obtained from Clonetics (San Diego, Calif.) and cultured in alpha-MEM (Gibco/BRL #12561-023) with 1% Pen/Strep (Gibco/BRL #15140-015) and 10% FBS (Hyclone #A-1115-L) at 37° C. in 5% $CO_2$. Cells are sub-cultured every 3–4 days as follows. Cells are washed twice with 5 ml Hanks balanced salt solution without $Ca^{++}$ or $Mg^{++}$ (BioWhittaker #10-547F) that has been pre-warmed to 37° C. Hanks solution will be aspirated and then 2 ml of 0.001% pronase incubated with the cells for 5 minutes at 37° C. Volume will be brought to 10 ml with pre-warmed alpha-MEM and a pipette used to dissociate the cells. Cells are then split 1:10 and carried for additional growth. Induction of phenotype (mineralization) is accomplished by supplementing the media with Hydrocortisone 21 Hemisuccinate and β-glycerophosphate as suggested by cell line supplier.

Media in all cultures is changed every 2–3 days. Cultures are evaluated at 7, 14, and 21 days for DNA content, Alkaline Phosphatase (ALP) activity, osteocalcin secretion, for calcium deposition, and by histology for bone matrix formation.

Analysis

The study compares 4 active arms with a control to evaluate the cultured cells at time intervals of 7, 14, and 21 days, evaluating:
→human osteoblasts with electro-stimulus A for 2 hours, 3 times daily
→human osteoblasts with electro-stimulus B for 2 hours, 3 times daily
→human osteoblasts with electro-stimulus A for 30 minutes, 3 times daily
→human osteoblasts with electro-stimulus B for 30 minutes, 3 times daily
→human osteoblasts control, no stimulus DNA Measurement Cellularity of the cultures is determined using a fluorometric DNA assay. Briefly, cells are removed from the cultures at day 7, 14, or 21, washed with double distilled $H_2O$, and homogenized in 1.4 mL of cold 10 mM EDTA, pH 12.3. The homegates are sonicated for 10 minutes in an ice bath, incubated for 20 minutes at 37° and returned to an ice bath. A volume of 200 µl of 1 M $KH_2PO_4$ is added to neutralize the pH. DNA standards are prepared from stock DNA solutions containing highly polymerized calf thymus DNA (type I, Sigma) at a concentration of 50 µg/mL. A volume of 200 µL of the standard or the homogenized sample is mixed with 1.3 mL of a 200 ng/mL Hoechst 33258-dye (Polysciences, Warrington, Pa.) in a 100 mM NaCl and 10 mM Tris buffer solution. The fluorescence emission at 455 nm is read at an excitation wavelength of 350 nm on a fluorescence spectrophotometer.

ALP Activity

AP activity is measured with a commercially available kit (ALP-10, Sigma. Cells is placed in centrifuge tube containing 1 mL of a 1M Tris solution at neutral pH and homogenized. The homogenate is further sonicated for 10 minutes in an ice bath, and a volume of 20 µL of each sample is added to 1 mL of reconstituted reagent provided by the kit at 30° C. Absorbance is measured every minute for 4 minutes at 405 nm using a HP 8452A Diode array spectrophotometer. The slope of the absorbance versus time will be used to calculate the ALP activity.

Osteocalcin Secretion

Osteocalcin secreted in the culture media is determined using a commercially available sandwich immunoassay (BT-480) from BTI (Stoughton, Mass.). The BTI Mid-Tact Osteocalcin Elisa Kit is highly specific. It measures both the intact human osteocalcin and the major (1-43) fragment. The assay is a sandwich ELISA that employs two monoclonal antibodies. One antibody (1-19) is immobilized in the wells and the second antibody (30-40) is biotinylated. The assay is highly sensitive (0.5 ng/ml) and requires only a 25 microliter sample. All the necessary reagents, a 96-well strip plate, and a complete 3½ hour protocol are included with the kit.

Calcium Deposition

Calcium deposition within the culture dishes is measured by the ortho-cresolphtalein complexone procedure (Sigma Diagnostics, Procedure No. 587). Scaffolds are washed with distilled water, and placed on an orbital shaker to incubate overnight in the presence of 2 mL of 0.5 N acetic acid. Equal volumes of the calcium-binding reagent (0.024% orthocresophtalein complexone and 0.25% 8-hydroxyquinalone) and the calcium buffer (500 mmol/L 2-amino-2-methyl-1,3 propanediol and other non-reactive stabilizers) provided in the assay kit are mixed to generate the assay working solution. A volume of 300 µL of working solution is added to 10 µL of sample in a 96-well plate. To generate a standard curve, serial dilutions of $CaCl_2$ are prepared (1–250 µg/mL). The plate is incubated at room temperature for 10 minutes and then read at 575 nm. Calcium deposition from each scaffold is reported as mg $Ca^{2+}$ equivalents.

Histology and Tetracycline Fluorescence Microscopy

Scaffolds are immersion fixed in 2% glutaraldehyde, dehydrated in rising concentrations of alcohol and rapidly embedded into plastic for thin sectioning. Sections are stained by Goldner trichrome, and Toluidine blue methodology. Mineral deposition is evaluated by adding tetracycline-HCL in the culture media at a final concentration of 10 µg/mL and is a well-established methodology for evaluating matrix deposition. Tetracycline accumulates at bone forming sites and morphometric evaluation is carried out using standard Bioquant software on a Nikon E1000 research microscope.

Synopsis

This study is designed to test the utility of imbuing osteoblasts with bioelectric signals that enhance bone-specific performance functions. The study evaluates 5 conditions over 3 separate time periods. The "quick and dirty" part of the study is to evaluate alkaline phosphatase and osteocalcin as first outcome determinants. Secondary objectives seek to identify morphologic criteria, i.e. calcium deposition and tetracycline absorption as an index of matrix mineralization. Data is collected as follows:

| Treatment | 7-day treatment | 14-day treatment | 21-day treatment |
| --- | --- | --- | --- |
| Osteoblasts 30-min, 3 × per day, Stim A | | | |
| osteoblasts 30-min, 3 × per day, Stim A | | | |
| osteoblasts 30-min, 3 × per day, Stim A | | | |
| osteoblasts 2 hrs, 3 × per day, Stim A | | | |
| osteoblasts 2 hrs, 3 × per day, Stim A | | | |
| osteoblasts 2 hrs, 3 × per day, Stim A | | | |
| osteoblasts 30-min, 3 × per day, Stim B | | | |
| osteoblasts 30-min, 3 × per day, Stim B | | | |
| osteoblasts 30-min, 3 × per day, Stim B | | | |
| osteoblasts 2 hrs, 3 × per day, Stim B | | | |
| osteoblasts 2 hrs, 3 × per day, Stim B | | | |
| osteoblasts 2 hrs, 3 × per day, Stim B | | | |
| control osteoblasts | | | |
| control osteoblasts | | | |
| control osteoblasts | | | |

Each experimental condition is duplicated, minimum of 6 wells per treatment arm. To accommodate the mineralization and tetracycline evaluation, an additional 2 sets are scheduled to be conducted for 21 days, as that is the critical mineralization front. In this study, 15 arms, ×2 sets of data cultures, and 5 additional sets ×2 are needed to approach the mineralization analysis.

The foregoing examples are considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

The invention claimed is:

1. An apparatus for generating an electrical signal for use in biomedical applications said apparatus comprising
    (a) a first frequency generator that generates a first intermediate output, said first intermediate output being coupled to and thereby controlling
    (b) a second frequency generator that generates one or more second intermediate outputs, said second intermediate outputs being coupled to
    (c) one or more active or passive electrical components that modify said second intermediate outputs thereby producing one or more third intermediate outputs, said third intermediate outputs being coupled to and thereby controlling one or more logic-level drivers that generate one or more fourth intermediate outputs, said fourth intermediate outputs being coupled to an output filter that generates a final output, said final output constituting said electrical signal comprising: (i) at least four relatively longer primary timing intervals $T_1, T_2, T_3, T_4$ and others if present, forming in succession a repeating primary cycle, said primary cycle having a first frequency; (ii) at least two relatively shorter secondary timing intervals $t_1$, $t_2$ and so forth, into which at least one of said primary timing intervals is divided and which form in succession a repeating secondary cycle throughout its length, said secondary cycle having a second frequency, said second frequency being less than about 200 kHz; while at least one other of said primary timing intervals is not so divided; (iii) a plurality of substantially constant voltage or current levels $L_1$, $L_2$ and so forth; (iv) selection of one of said voltage or current levels during each of said secondary intervals within a said primary interval which is so divided, or during the whole of said primary interval if it is not so divided: said levels, selected in succession throughout the course of said primary cycle, thereby forming said electrical signal; and (v) further selection of one or more of said primary intervals, said further selected intervals being not so divided, as one or more equalizing pulses for the establishment of substantial charge balance throughout the course of any one repetition of said primary cycle,
    wherein the selection of said primary and secondary timing intervals, and of said voltage or current levels within each, cause said electrical signal to emulate a specific, defined mathematical function having an amplitude which varies with time, and
    wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

2. The apparatus as recited in claim 1 further comprising a sequential switch that couples said first intermediate output to said second frequency generator.

3. The apparatus as recited in claim 1 further comprising one or more switches that couple said second intermediate output to said one or more electrical components, said electrical components being active or passive.

4. The apparatus as recited in claim 1 wherein the apparatus may be used to relieve pain, improve sensation, or improve neural function due to one or more of the following: trauma, surgery, nerve irritation, muscle spasm, trapped nerves, compressed nerves, diabetic neuropathy, peripheral neuropathy, autonomic neuropathy, peripheral vascular disease, plantar fasciitis, low back pain, patella femoral pain.

5. The apparatus as recited in claim 1 wherein the electrical signal generated comprises a waveform comprising at least five primary timing intervals including a zero interval (80), followed by a plurality of high frequency intervals (82*a*), (82*b*), (82*c*) and at least one undivided interval (84).

6. The apparatus as recited in claim 5, wherein the user of said apparatus can select one of said electrical signals to be generated.

7. The apparatus as recited in claim 1 wherein the electrical signal generated comprises a waveform comprising at least four primary timing intervals that include a zero interval (80) and three high frequency intervals (42*a*), (42*b*) and (42*c*).

8. The apparatus as recited in claim 7, wherein the user of said apparatus can select one of said electrical signals to be generated.

9. The apparatus as recited in claim 1 wherein the electrical signal generated comprises a waveform comprising at least four primary timing intervals that include a zero interval (80) and three high frequency intervals (44*a*), (44*b*) and (44*c*).

10. The apparatus as recited in claim 9, wherein the user of said apparatus can select one of said electrical signals to be generated.

11. The apparatus as recited in claim 1 wherein the electrical signal generated comprises a waveform comprising at least eight primary timing intervals that include a zero interval (80) and seven high frequency intervals (46*a*), (46*b*), (46*c*), (46*d*), (46*e*), (46*f*) and (46*g*).

12. The apparatus as recited in claim 11, wherein the user of said apparatus can select one of said electrical signals to be generated.

13. The apparatus as recited in claim 1 wherein the electrical signal generated comprises a waveform comprising at least ten primary timing intervals that include a first zero interval (80), followed by a first high frequency interval (48*a*), followed by a second zero interval (80), and a second high frequency interval (48*b*) followed by a third zero interval (80) and a third high frequency interval (48*c*) followed by a fourth zero interval (80) and a fourth high frequency interval (48*d*) followed by a fifth zero interval (80) and a fifth high frequency interval (48*e*).

14. The apparatus as recited in claim 13, wherein the user of said apparatus can select one of said electrical signals to be generated.

15. The apparatus as recited in claim 1 wherein the electrical signal generated comprises a waveform comprising at least six primary timing intervals that include a zero interval (80), and five high frequency intervals (70*a*), (70*b*), (70*c*), (70*d*), and (70*e*).

16. The apparatus as recited in claim 15, wherein the user of said apparatus can select one of said electrical signals to be generated.

17. The apparatus as recited in claim 1 wherein the electrical signal generated comprises a waveform comprising at least six primary timing intervals that include a first zero interval (80), a first high frequency interval (72a), followed by a first undivided interval (72b) followed by a second zero interval (80), followed by a second high frequency interval (72c) and a second undivided interval (72d).

18. The apparatus as recited in claim 17, wherein the user of said apparatus can select one of said electrical signals to be generated.

19. The apparatus as recited in claim 1 wherein the electrical signal generated comprises a waveform comprising at least four primary timing intervals that include a first zero interval (80), followed by a first high frequency interval (74a) followed by a second zero interval (80) followed by a second high frequency interval (74b).

20. The apparatus as recited in claim 19, wherein the user of said apparatus can select one of said electrical signals to be generated.

21. The apparatus as recited in claim 1, wherein (a) said electrical signal within any given primary timing interval has both an A.C. and a D.C. amplitude either of which may be zero, and (b) said A.C. amplitude within said primary timing interval, if not zero, results from the presence of a said secondary timing cycle.

22. The apparatus as recited in claim 21, wherein (b) said A.C. amplitude has an amplitude of zero in at least one of said primary timing intervals, and (c) said A.C. amplitude has a nonzero amplitude in at least one other of said primary timing intervals.

23. The apparatus as recited in claim 22, wherein: (a) a first said primary timing interval $T_1$ has a single voltage or current level $L_1$ selected throughout, resulting in a zero A.C. amplitude; (b) a second said primary timing interval $T_2$ is divided into said secondary intervals $t_1$, $t_2$ and so forth, forming said secondary cycle throughout the length of primary interval $T_2$, said secondary cycle undergoing a plurality of complete repetitions within said primary interval, one of levels $L_1$, $L_2$ and so forth being selected for each of secondary intervals $t_1$, $t_2$ and so forth, resulting in a nonzero A.C. amplitude; (c) a third said primary timing interval $T_3$, (d) a fourth said primary timing interval $T_4$, and each said primary timing interval $T_5$, $T_6$ and so forth, if present, may either contain a single, constant voltage or current level in the manner of $T_1$, or be subdivided in the manner of interval $T_2$; (e) each said secondary interval or undivided primary interval within said primary cycle has a uniquely assigned voltage or current level, from among $L_1$, $L_2$ and so forth, which is always selected when that interval recurs; and therefore, (f) said electrical signal is substantially identical between any two repetitions of said primary cycle.

24. The apparatus as recited in claim 23, wherein said substantially constant voltage or current levels $L_1$, $L_2$ and so forth take the form of constant current levels lying within the range between +10.0 and −10.0 milliamperes.

25. The apparatus as recited in claim 23, wherein said primary cycle comprises two longest primary timing intervals $T_A$ and $T_B$, having the relationship $2T_A \leq T_B \leq 20T_A$ where $T_B$ is the longest primary interval and $T_A$ is the second longest, thereby yielding an asymmetric primary cycle with a duty cycle between 66% and 95%.

26. The apparatus as recited in claim 23, wherein at least two of said at least four primary timing intervals differ in length and contain secondary cycles which also differ in frequency.

27. The apparatus as recited in claim 23, wherein said secondary cycle comprises exactly two of said secondary timing intervals $t_1$ and $t_2$, having the relationship $2t_A \leq t_B \leq 20t_A$ where $t_A$ may be either of said secondary timing intervals while $t_B$ is the other, thereby yielding an asymmetric secondary cycle with a duty cycle between 66% and 95%.

28. The apparatus as recited in claim 23, wherein said secondary cycle comprises more than two of said secondary timing intervals $t_1$, $t_2$, $t_3$ and so forth.

29. The apparatus as recited in claim 23, wherein said electrical signal is automatically turned off after a preselected period of time.

30. The apparatus as recited in claim 23, comprising: (a) generating said plurality of primary timing intervals $T_1$, $T_2$ and so forth, thereby forming said repeating primary cycle; (b) generating said plurality of secondary timing intervals $t_1$, $t_2$ and so forth, thereby forming said repeating secondary cycle during said at least one primary interval which is so divided; (c) selecting among said plurality of constant voltage or current levels $L_1$, $L_2$ and so forth, one for each of said secondary intervals within a said primary interval which is so divided, or the whole of said primary interval if it is not so divided, thereby forming said electrical signal; and (d) conductive material for applying said electrical signal to living or nonliving materials.

31. The apparatus as recited in claim 30, further comprising a filter for removing unwanted components from said electrical signal.

32. The apparatus as recited in claim 30, wherein at least one of said generation of said plurality of primary timing intervals or said plurality of secondary timing intervals, thereby forming said repeating primary cycle or said repeating secondary cycle, includes a multistep sequencer.

33. The apparatus as recited in claim 30, wherein said electrical signal is periodic and in which said primary and secondary timing intervals have approximately the magnitudes and relationships: (a) 50 μsec $\leq (T_1, T_2, \ldots) \leq$ 30 sec; (b) 200 μsec $\leq (T_1+T_2+ \ldots) \leq$ 120 sec; (c) 2.55 μsec $(t_1, t_2, \ldots) \leq$ 50 msec; (d) 5 μsec $\leq (t_a+t_b+ \ldots)$ 0.5 $T_A$; (e) $(t_x, t_y, \ldots) \leq 2(t_a+t_b+ \ldots)$; and (f) where $(T_1, T_2, \ldots)$, $(T_1+T_2+ \ldots)$, $T_A$, $(t_1, t_2)$, $(t_a+t_b+ \ldots)$ and $(t_x, t_y, \ldots)$ are as defined in the specification.

34. The apparatus as recited in claim 33, configured to generate four said primary intervals $T_1$, $T_2$, $T_3$ and $T_4$, a plurality of said secondary intervals $t_1$, $t_2$ and so forth, and three said voltage or current levels $L_1$, $L_2$ and $L_3$, such that: (a) $L_1$ is substantially zero; (b) $L_2$ and $L_3$ have substantially equal magnitudes but opposite polarities; (c) $T_1$ is spent at a constant $L_1$; and (d) $T_2$, $T_3$ and $T_4$ all contain secondary timing cycles.

35. The apparatus as recited in claim 34, wherein: (a) $T_1$ is the shortest of said primary intervals $T_1$, $T_2$, $T_3$ and $T_4$; (b) $T_2$ and $T_4$ are roughly equal in length; (c) $T_3$ is longer than either $T_2$ or $T_4$; and (d) the A.C. amplitude produced by said secondary timing cycle within $T_2$ and $T_4$ is reduced below that produced by said secondary timing cycle within $T_3$.

36. The apparatus as recited in claim 35, wherein: (a) the repetition rate of said primary timing cycle may be varied, continuously or stepwise, across some portion of the range from 1 Hz to 500 Hz in order to suit the desired application; and (b) the repetition rates of said secondary timing cycles within $T_2$, $T_3$ and $T_4$ are substantially equal and lie in the range between 1000 Hz to 200 kHz.

37. The apparatus as recited in claim 35, wherein said amplitude reduction of the signal during $T_2$ and $T_4$, below that during $T_3$, is achieved, in whole or in part, through the selection of at least one said voltage or current level during $T_3$ which is not used during either $T_2$ or $T_4$.

38. The apparatus as recited in claim 35, wherein said amplitude reduction of the signal during $T_2$ and $T_4$, below that during $T_3$, is achieved, in whole or in part, through the use of a different said secondary timing cycle during $T_3$ from that which is used during either $T_2$ or $T_4$.

39. The apparatus as recited in claim 33, configured to generate a plurality P of at least four of said primary timing intervals $T_1$, $T_2$, $T_3$ and so forth, an even number S of said secondary timing intervals $t_1$, $t_2$, $t_3$ and so forth, and an odd number Q of said voltage or current levels $L_1$, $L_2$, $L_3$ and so forth, such that: (a) $L_1$ is substantially zero; (b) The remaining said voltage and current levels $L_2$, $L_3$ and so forth form at least one pair such as $L_X$, $L_Y$, the members of each said pair being equal in magnitude but opposite in polarity; (c) $T_1$ is spent at a constant $L_1$; (d) all other said primary timing intervals $T_2$, $T_3$ and so forth contain secondary cycles all having substantially equal repetition rates; (e) a maximum signal amplitude is present during a primary timing interval $T_N$, where N preferably equals about P/2+1; and (f) during the remaining said primary intervals, said signal amplitudes increase progressively from $T_1$ to $T_N$ going either forward or backward around said primary timing cycle, thereby approximating a sinusoidal envelope with its maximum during $T_N$ and minimum during $T_1$.

40. The apparatus as recited in claim 33, configured to generate any number of said primary timing intervals $T_1$, $T_2$, $T_3$ and so forth, two said secondary timing intervals $t_1$ and $t_2$, and three said voltage or current levels $L_1$, $L_2$ and $L_3$, such that: (a) $L_1$ is substantially zero; (b) $L_2$ and $L_3$ have substantially equal magnitudes but opposite polarities; and (c) primary intervals are grouped in threes, wherein (1) the first said primary timing interval in each said group, such as $T_1$, $T_4$, $T_7$ and so forth, are spent at a constant $L_1$; (2) the second said primary timing interval in each said group, such as $T_2$, $T_5$, $T_8$ and so forth, contains a said secondary timing cycle alternating between $L_2$ during $t_1$ and $L_3$ during $t_2$, thereby forming a square- or rectangular-wave signal within each such said even-numbered primary interval; and (3) the third said primary timing interval in each said group, such as $T_3$, $T_6$, $T_9$ and so forth, is spent at a constant voltage or current level which differs from $L_1$ thereby forming an equalizing pulse.

41. The apparatus as recited in claim 40, wherein the sum of D.C. amplitudes throughout the primary timing cycle is zero, so that the resulting said electrical signal is charge-balanced.

42. The apparatus as recited in claim 41, wherein (a) said second primary timing interval in each said group contains a rectangular wave having a non-zero D.C. amplitude, and (b) said third primary timing interval in each said group has an opposite D.C. amplitude, causing said electrical signal to be substantially charge-balanced.

43. The apparatus as recited in claim 40, wherein said second and third primary timing intervals within at least one of said groups of three have opposite polarities from those in at least one other of said groups of three.

44. The apparatus as recited in claim 43, wherein (a) at least one of said third primary timing intervals, within at least one of said groups of three, and forming an equalizing pulse, is too short to fully achieve charge balance; and (b) charge balance instead is achieved, in whole or in part, through polarity reversal between at least one of said second primary timing intervals, and at least one other of said second primary timing intervals, within said groups of three.

45. The apparatus as recited in claim 40, wherein at least one of said second primary timing intervals, within at least one of said groups of three, contains a secondary timing cycle whose repetition rate differs from that in at least one other of said second primary timing intervals.

46. The apparatus as recited in claim 37, further comprising a switch whereby the primary timing intervals, secondary timing intervals, voltage or current levels, or any combination of these may be altered so as to produce any of a plurality of the electrical signals already described, upon demand.

47. The apparatus as recited in claim 46, wherein said selection comprises: (a) the electrical signal as recited in claim 39; or (b) the electrical signal as recited in claim 42.

48. The apparatus as recited in claim 30, in which said electrical signal is aperiodic and in which said primary and secondary timing intervals have approximately the magnitudes and relationships: (a) 50 μsec$\leq(T_2, T_3, \ldots)\leq$30 sec, (b) 200 μsec$\leq(T_2+T_3+\ldots)\leq$120 sec, (c) 2.55 μsec$\leq(t_1, t_2, \ldots)\leq$50 msec, (d) 5 μsec$\leq(t_a+t_b+\ldots)\leq$0.5 $T_4$, and (e) $(t_x, t_y, \ldots)\leq 2(t_a+t_b+\ldots)$, where $T_1$ may be arbitrarily long, and where $(T_2, T_3, \ldots)$, $(T_2+T_3+\ldots)$, $T_4$, $(t_1, t_2, \ldots)$, $(t_a+t_b+\ldots)$ and $(t_x, t_y, \ldots)$ are as defined in the specification.

49. The apparatus as recited in claim 48, configured to generate any number P of said primary timing intervals $T_1$, $T_2$, $T_3$ and so forth, an even number S of said secondary timing intervals $t_1$, $t_2$, $t_3$ and so forth, and an odd number Q of said voltage or current levels $L_1$, $L_2$, $L_3$ and so forth, such that: (a) $L_1$ is substantially zero; (b) the remaining voltage and current levels $L_2$, $L_3$ and so forth form at least one pair such as $L_X$, $L_Y$, the members of each said pair being equal in magnitude but opposite in polarity; (c) $T_1$ is spent at a constant $L_1$; (d) all other said primary timing intervals $T_2$, $T_3$ and so forth contain secondary cycles all having substantially equal repetition rates; (e) a maximum signal amplitude is present during $T_2$; and (1) during the remaining said primary intervals, said signal amplitudes decrease progressively with time throughout said primary timing cycle, thereby approximating an exponentially-decaying envelope with its maximum during $T_2$ and minimum during $T_P$.

50. The apparatus as recited in claim 49, wherein each iteration of the primary timing cycle is initiated by an external signal.

51. The apparatus as recited in claim 30, wherein said electrical signal is applied by conductive material to a human or animal body, isolated tissue or cell culture in order to relieve pain, stimulate healing, or increase cell metabolism, proliferation, differentiation, or production of desired substances or reduction of undesirable substances.

52. The apparatus as recited in claim 51, wherein said conductive material constitutes a plurality of flat bodies of electrically-conductive material applied directly to the skin surface.

53. The apparatus as recited in claim 51, wherein said conductive material includes at least one body of electrically-conductive material applied to a tissue surface other than the skin.

54. The apparatus as recited in claim 51, wherein said conductive material includes at least one body of electrically-conductive material inserted into or implanted within a human or animal body or tissue.

55. The apparatus as recited in claim 51, wherein said conductive material includes at least one body of electrically-conductive material wholly or partially immersed in an electrically-conductive liquid.

56. The apparatus as recited in claim 51, wherein said conductive material include a body of electrically-conductive liquid in which a human or animal body or tissue, or part thereof, may be immersed.

57. The apparatus as recited in claim 30, wherein said electrical signal is applied by conductive material to a human or animal body, isolated tissue or cell culture, food, beverage or other material in order to devitalize selected pathogenic organisms which may be present.

58. An apparatus for generating an electrical signal for use in biomedical applications, said apparatus comprising (a) a first frequency generator that generates a first intermediate output, said first intermediate output being coupled to and thereby controlling (b) a second frequency generator that generates one or more second intermediate outputs, said second intermediate outputs being coupled to (c) one or more active or passive electrical components that modify said second intermediate outputs thereby producing one or more third intermediate outputs, said third intermediate outputs being coupled to and thereby controlling one or more logic-level drivers that generate one or more fourth intermediate outputs, said fourth intermediate outputs being coupled to an output filter that generates a final output, said final output constituting said electrical signal comprising: (a) at least four relatively longer primary timing intervals $T_1$, $T_2$, $T_3$, $T_4$ and others if present, forming in succession a repeating primary cycle, said primary cycle having a frequency; (b) at least two relatively shorter secondary timing intervals $t_1$, $t_2$ and so forth, into which at least one of said primary timing intervals is divided and which form in succession a repeating secondary cycle throughout its length, said secondary cycle having a frequency, said frequency lying below 200 kHz; while at least one other of said primary timing intervals is not so divided; (c) a plurality of substantially constant voltage or current levels $L_1$, $L_2$ and so forth; (d) selection of one of said voltage or current levels during each of said secondary intervals within a said primary interval which is so divided, or during the whole of said primary interval if it is not so divided: said levels, selected in succession throughout the course of said primary cycle, thereby forming said electrical signals
wherein the selection of said primary and secondary timing intervals, and of said voltage or current levels within each, cause said electrical signal to emulate a specific, defined mathematical function having an amplitude which varies with time, and
wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

59. The apparatus as recited in claims or 58 wherein said biomedical applications further comprise treatment of rotator cuff injury, treatment of osteoarthritis, treatment of carpal tunnel syndrome.

60. A method for generating an electrical signal for use in biomedical applications said, method comprising:
(a) generating at least four relatively longer primary timing intervals $T_1$, $T_2$, $T_3$, $T_4$ and others if present, forming in succession a repeating primary cycle, said primary cycle having a frequency;
(b) generating at least two relatively shorter secondary timing intervals $t_1$, $t_2$ and so forth, into which at least one of said primary timing intervals is divided and which form in succession a repeating secondary cycle throughout its length, said secondary cycle having a frequency, said frequency lying below 200 kHz; while at least one other of said primary timing intervals is not so divided;
(c) generating a plurality of substantially constant voltage or current levels $L_1$, $L_2$ and so forth;
(d) selecting one of said voltage or current levels during each of said secondary intervals within a said primary interval which is so divided, or during the whole of said primary interval if it is not so divided: said levels, selected in succession throughout the course of said primary cycle, thereby forming said electrical signal;
(e) further selecting one or more of said primary intervals, said further selected intervals being not so divided, as one or more equalizing pulses for the establishment of substantial charge balance throughout the course of any one repetition of said primary cycle; and
(f) applying said electrical signal to one or more of the following: human body, animal body, cell culture, tissue culture, food, liquid, and pharmaceutical materials,
wherein the selection of said primary and secondary timing intervals, and of said voltage or current levels within each, cause said electrical signal to emulate a specific, defined mathematical function having an amplitude which varies with time, and
wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

61. The method as recited in claim 60, further comprising filtering said electrical signal to remove unwanted components.

62. The method as recited in claim 60, wherein said electrical signal is applied by said conductive material to a human or animal body, isolated tissue or cell culture, food, beverage or other material to inactivate selected pathogenic organisms which may be present.

63. The method as recited in claim 60 wherein the method may be used to relieve pain, improve sensation, or improve neural function due to one or more of the following: trauma, surgery, nerve irritation, muscle spasm, trapped nerves, compressed nerves, diabetic neuropathy, peripheral neuropathy, autonomic neuropathy, peripheral vascular disease, plantar fasciitis, low back pain, patella femoral pain.

64. The method as recited in claim 60 wherein the electrical signal generated comprises a waveform comprising at least five primary timing intervals including a zero interval (80), followed by a plurality of high frequency intervals (82a), (82b), (82c) and at least one undivided interval (84).

65. The method as recited in claim 60 wherein the electrical signal generated comprises a waveform comprising at least four primary timing intervals that include a zero interval (80) and three high frequency intervals (42a), (42b) and (42c).

66. The method as recited in claim 60 wherein the electrical signal generated comprises a waveform comprising at least four primary timing intervals that include a zero interval (80) and three high frequency intervals (44a), (44b) and (44c).

67. The method as recited in claim 60 wherein the electrical signal generated comprises a waveform comprising at least eight primary timing intervals that include a zero interval (80) and seven high frequency intervals (46a), (46b), (46c), (46d), (46e), (46f) and (46g).

68. The method as recited in claim 60 wherein the electrical signal generated comprises a waveform comprising at least ten primary timing intervals that include a first zero interval (80), followed by a first high frequency interval (48a), followed by a second zero interval (80), and a second high frequency interval (48b) followed by a third zero interval (80) and a third high frequency interval (48c) followed by a fourth zero interval (80) and a fourth high frequency interval (48d) followed by a fifth zero interval (80) and a fifth high frequency interval (48e).

69. The method as recited in claim 60 wherein the electrical signal generated comprises a waveform comprising at least six primary timing intervals that include a zero interval (80), and five high frequency intervals (70a), (70b), (70c), (70d), and (70e).

70. The method as recited in claim 60 wherein the electrical signal generated comprises a waveform comprising at least six primary timing intervals that include a first zero interval (80), a first high frequency interval (72a), followed by a first undivided interval (72b) followed by a second zero interval (80), followed by a second high frequency interval (72c) and a second undivided interval (72d).

71. The method as recited in claim 60 wherein the electrical signal generated comprises a waveform comprising at least four primary timing intervals that include a first zero interval (80), followed by a first high frequency interval (74a) followed by a second zero interval (80) followed by a second high frequency interval (74b).

72. The method as recited in claim 60, wherein a multistep sequencer is used to help generate said primary timing intervals $T_1$, $T_2$ and so forth, forming said repeating primary cycle.

73. The method as recited in claim 72, wherein the outputs of said multistep sequencer determine the relative lengths of said primary timing intervals.

74. The method as recited in claim 60, wherein a multistep sequencer is used to help generate said secondary timing intervals $t_1$, $t_2$ and so forth, forming said repeating secondary cycle.

75. The method as recited in claim 74, wherein the outputs of said multistep sequencer determine the relative lengths of said secondary timing intervals.

76. The method as recited in claim 60, in which said electrical signal is aperiodic and in which said primary and secondary timing intervals have approximately the magnitudes and relationships: (a) 50 μsec $(T_2, T_3, \ldots) \leq 30$ sec, (b) 200 μsec $\leq (T_2+T_3+ \ldots) \leq 120$ sec, (c) 2.5 μsec $\leq (t_1, t_2, \ldots) \leq 50$ msec, (d) 5 μsec $\leq (t_a+t_b+ \ldots) \leq 0.5 T_4$, and (e) $(t_x, t_y, \ldots) \leq 2(t_a+t_b+ \ldots)$, where $T_1$ may be arbitrarily long, and where $(T_2, T_3, \ldots)$, $(T_2+T_3+ \ldots)$, $T_4$, $(t_1, t_2, \ldots)$, $(t_a+t_b \ldots)$ and $(t_x, t_y, \ldots)$ are as defined in the specification.

77. The method as recited in claim 76, wherein are generated any number P of said primary timing intervals $T_1$, $T_2$, $T_3$ and so forth, an even number S of said secondary timing intervals $t_1$, $t_2$, $t_3$ and so forth, and an odd number Q of said voltage or current levels $L_1$, $L_2$, $L_3$ and so forth, such that: (a) $L_1$ is substantially zero; (b) the remaining said voltage and current levels $L_2$, $L_3$ and so forth form at least one pair such as $L_X$, $L_Y$, the members of each said pair being equal in magnitude but opposite in polarity; (c) $T_1$ is spent at a constant $L_1$; (d) all other said primary timing intervals $T_2$, $T_3$ and so forth contain secondary cycles all having substantially equal repetition rates; (e) a maximum signal amplitude is present during $T_2$; and (f) during the remaining said primary intervals, said signal amplitudes decrease progressively with time throughout said primary timing cycle, thereby approximating an exponentially-decaying envelope with its maximum during $T_2$ and minimum during $T_P$.

78. The method as recited in claim 77, wherein each iteration of the primary timing cycle is initiated by an external signal.

79. The method as recited in claim 60, wherein said electrical signal is applied by conductive material to a human or animal body, isolated tissue or cell culture to relieve pain, stimulate healing, or increase cell metabolism, proliferation, differentiation, or production of desired substances or reduction of undesirable substances.

80. The method as recited in claim 79, wherein said conductive material constitutes a plurality of flat bodies of electrically-conductive material applied directly to the skin surface.

81. The method as recited in claim 79, wherein said conductive material includes at least one body of electrically-conductive material applied to a tissue surface other than the skin.

82. The method as recited in claim 79, wherein said conductive material includes at least one body of electrically-conductive material inserted into or implanted within a human or animal body or tissue.

83. The method as recited in claim 79, wherein said conductive material includes at least one body of electrically-conductive material wholly or partially immersed in an electrically-conductive liquid.

84. The method as recited in claim 79, wherein said conductive material includes a body of electrically-conductive liquid in which a human or animal body or tissue, or part thereof, may be immersed.

85. The method as recited in claim 60, wherein: (a) said electrical signal within any given primary timing interval has both an A.C. and a D.C. amplitude either of which may be zero, and (b) said A.C. amplitude within said primary timing interval, if not zero, results from the presence of a said secondary timing cycle.

86. The method as recited in claim 85, wherein: (b) said A.C. component has an amplitude of zero in at least one of said primary timing intervals, and (c) said A.C. component has a nonzero amplitude in at least one other of said primary timing intervals.

87. The method as recited in claim 86, wherein: (a) first said primary timing interval $T_1$ has a single voltage or current level $L_1$ selected throughout, resulting in a zero A.C.

amplitude; (b) second said primary timing interval $T_2$ is divided into said secondary intervals $t_1$, $t_2$ and so forth, forming said secondary cycle throughout the length of primary interval $T_2$, said secondary cycle undergoing a plurality of complete repetitions within said primary interval, one of levels $L_1$, $L_2$ and so forth being selected for each of secondary intervals $t_1$, $t_2$ and so forth, resulting in a nonzero A.C. amplitude; (c) third said primary timing interval $T_3$, fourth said primary timing interval $T_4$, and each said primary timing interval $T_5$, $T_6$ and so forth, if present, may either contain a single, constant voltage or current level in the maimer of $T_1$, or be subdivided in the maimer of interval $T_2$; (d) each said secondary interval or undivided primary interval within said primary cycle has a uniquely assigned voltage or current level, from among $L_1$, $L_2$ and so forth, which is always selected when that interval recurs; and therefore, (e) said electrical signal is substantially identical between any two repetitions of said primary cycle.

88. The method as recited in claim 87, wherein said substantially constant voltage or current levels $L_1$, $L_2$ and so forth take the form of constant current levels +10.0 and −10.0 milliamperes.

89. The method as recited in claim 88, wherein said primary cycle comprises two longest primary timing intervals $T_A$ and $T_B$, having the relationship $2T_A \leq T_B \leq 20T_A$ where $T_B$ is the longest primary interval and $T_A$ is the second longest, thereby yielding an asymmetric primary cycle with a duty cycle between 66% and 95%.

90. The method as recited in claim 88, wherein at least two of said at least four primary timing intervals differ in length and contain secondary cycles which also differ in frequency.

91. The method as recited in claim 87, wherein said secondary cycle comprises exactly two said secondary timing intervals $t_1$ and $t_2$, having the relationship $2t_A \leq t_B \leq 20t_A$ where $t_A$ may be either of said secondary timing intervals while $t_B$ is the other, thereby yielding an asymmetric secondary cycle with a duty cycle between 66% and 95%.

92. The method as recited in claim 87, wherein said electrical signal is automatically turned off after a preselected period of time.

93. The method as recited in claim 60, wherein said electrical signal is periodic and in which said primary and secondary timing intervals have approximately the magnitudes and relationships: (a) 50 µsec $\leq (T_1, T_2, \ldots) \leq$ 30 sec; (b) 200 µsec $\leq (T_1+T_2+\ldots) \leq$ 120 sec; (c) 2.5 µsec $(t_1, t_2, \ldots) \leq$ 50 msec; (d) 5 µsec $\leq (t_a+t_b+\ldots) \leq 0.5T_A$; and (e) $(t_x, t_y, \ldots) \leq 2(t_a+t_b+\ldots)$; where $(T_1, T_2, \ldots)$, $(T_1+T_2+\ldots)$, $T_A$, $(t_1, t_2, \ldots)$, $(t_a+t_b\ldots)$ and $(t_x, t_y, \ldots)$ are as defined in the specification.

94. The method as recited in claim 93, wherein are generated four said primary intervals $T_1$, $T_2$, $T_3$ and $T_4$, a plurality of said secondary intervals $t_1$, $t_2$ and so forth, and three said voltage or current levels $L_1$, $L_2$ and $L_3$, such that: (a) $L_1$ is substantially zero; (b) $L_2$ and $L_3$ have substantially equal magnitudes but opposite polarities; (c) $T_1$ is spent at a constant $L_1$; and (d) $T_2$, $T_3$ and $T_4$ all contain secondary timing cycles.

95. The method as recited in claim 94, wherein: (a) $T_1$ is the shortest of said primary intervals $T_1$, $T_2$, $T_3$ and $T_4$; (b) $T_2$ and $T_4$ are roughly equal in length; (c) $T_3$ is longer than either $T_2$ or $T_4$; and (d) the A.C. amplitude produced by said secondary timing cycle within $T_2$ and $T_4$ is reduced below that produced by said secondary timing cycle within $T_3$.

96. The method as recited in claim 95, wherein: (a) the repetition rate of said primary timing cycle may be varied, continuously or stepwise, across some portion of the range from 1 Hz to 500 Hz in order to suit the desired application; and (b) the repetition rates of said secondary timing cycles within $T_2$, $T_3$ and $T_4$ are substantially equal and lie in the range between approximately 1000 Hz and 200 kHz.

97. The method as recited in claim 57, wherein said amplitude reduction of the signal during $T_2$ and $T_4$, below that during $T_3$, is achieved, in whole or in part, through the selection of at least one said voltage or current level during $T_3$ which is not used during either $T_2$ or $T_4$.

98. The method as recited in claim 95, wherein said amplitude reduction of the signal during $T_2$ and $T_4$, below that during $T_3$, is achieved, in whole or in part, through the use of a different said secondary timing cycle during $T_3$ from that which is used during either $T_2$ or $T_4$.

99. The method as recited in claim 93, wherein are generated a plurality P of at least four of said primary timing intervals $T_1$, $T_2$, $T_3$ and so forth, an even number S of said secondary timing intervals $t_1$, $t_2$, $t_3$ and so forth, and an odd number Q of said voltage or current levels $L_1$, $L_2$, $L_3$ and so forth, such that: (a) $L_1$ is substantially zero; (b) The remaining said voltage, and current levels $L_2$, $L_3$ and so forth form at least one pair such as $L_X$, $L_Y$, the members of each said pair being equal in magnitude but opposite in polarity; (c) $T_1$ is spent at a constant $L_1$; (d) all other said primary timing intervals $T_2$, $T_3$ and so forth contain secondary cycles all having substantially equal repetition rates; (e) a maximum signal amplitude is present during a primary timing interval $T_N$, where N preferably equals about P/2+1; and (f) during the remaining said primary intervals, said signal amplitudes increase progressively from $T_1$ to $T_N$ going either forward or backward around said primary timing cycle, thereby approximating a sinusoidal envelope with its maximum during $T_N$ and minimum during $T_1$.

100. The method as recited in claim 93, wherein are generated any number of said primary timing intervals $T_1$, $T_2$, $T_3$ and so forth, two said secondary timing intervals $t_1$ and $t_2$, and three said voltage or current levels $L_1$, $L_2$ and $L_3$, such that: (a) $L_1$ is substantially zero; (b) $L_2$ and $L_3$ have substantially equal magnitudes but opposite polarities; and (c) primary intervals are grouped in threes, wherein (1) the first said primary timing interval in each said group, such as $T_1$, $T_4$, $T_7$ and so forth, are spent at a constant $L_1$; (2) the second said primary timing interval in each said group, such as $T_2$, $T_5$, $T_8$ and so forth, contains a said secondary timing cycle alternating between $L_2$ during $t_1$ and $L_3$ during $t_2$, thereby forming a square- or rectangular-wave signal within each such said even-numbered primary interval; and (3) the third said primary timing interval in each said group, such as $T_3$, $T_6$, $T_9$ and so forth, is spent at a constant voltage or current level which differs from $L_1$ thereby forming an equalizing pulse.

101. The method as recited in claim 100, wherein the sum of D.C. amplitudes throughout the primary timing cycle is zero, so that the resulting said electrical signal is charge-balanced.

102. The method as recited in claim 101, wherein: (a) said second primary timing interval in each said group contains a rectangular wave having a non-zero D.C. amplitude, and (b) said third primary timing interval in each said group has an opposite D.C. amplitude, causing said electrical signal to be substantially charge-balanced.

103. The method as recited in claim 100, wherein said second and third primary timing intervals within at least one of said groups of three have opposite polarities from those in at least one other of said groups of three.

104. The method as recited in claim 100, wherein (a) at least one of said third primary timing intervals, within at least one of said groups of three, and forming an equalizing pulse, is too short to fully achieve charge balance; and (b) charge balance instead is achieved, in whole or in part, through polarity reversal between at least one of said second primary timing intervals, and at least one other of said second primary timing intervals, within said groups of three.

105. The method as recited in claim 100, wherein at least one of said second primary timing intervals, within at least one of said groups of three, contains a secondary timing cycle whose repetition rate differs from that in at least one other of said second primary timing intervals.

106. The method as recited in claim 60, further comprising the selection of one of a plurality of sets comprising primary timing intervals, secondary timing intervals, voltage or current levels, or any combination of these, so as to produce any of a plurality of the electrical signals already described, upon demand.

107. The method as recited in claim 106, wherein said selection comprises: (a) the electrical signal as recited in claim 100; and (b) the electrical signal as recited in claim 102.

108. A method for generating an electrical signal for use in biomedical applications, said method comprising: (a) generating at least four relatively longer primary timing intervals $T_1$, $T_2$, $T_3$, $T_4$ and others if present, forming in succession a repeating primary cycle, said primary cycle having a frequency; (b) generating at least two relatively shorter secondary timing intervals $t_1$, $t_2$ and so forth, into which at least one of said primary timing intervals is divided and which form in succession a repeating secondary cycle throughout its length, said secondary cycle having a frequency, said frequency being less than about 200 kHz; while at least one other of said primary timing intervals is not so divided; (c) generating a plurality of substantially constant voltage or current levels $L_1$, $L_2$ and so forth; (d) selecting one of said voltage or current levels during each of said secondary intervals within a said primary interval which is so divided, or during the whole of said primary interval if it is not so divided: said levels, selected in succession throughout the course of said primary cycle, thereby forming said electrical signal; and (e) applying said electrical signal to one or more of the following: human body, animal body, cell culture, tissue culture, food, liquid, and pharmaceutical materials wherein the selection of said primary and secondary timing intervals, and of said voltage or current levels within each, cause said electrical signal to emulate a specific, defined mathematical function having an amplitude which varies with time, and wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

109. The method as recited in claims 60 or 108 wherein said biomedical applications further comprise treatment of rotator cuff injury, treatment of osteoarthritis, treatment of carpal tunnel syndrome.

110. An apparatus comprising a generating assembly constructed and arranged to produce an electrical signal used in biomedical applications said electrical signal comprising (a) a repeating primary cycle, the primary cycle having at least four primary timing intervals, and (b) a repeating secondary cycle formed by dividing at least one of said primary timing intervals into at least two secondary timing intervals, the secondary cycle having a frequency below 200 kHz, each of the secondary intervals within the primary interval which is divided having a substantially constant voltage or current level, or during the whole of the primary interval not divided having a substantially constant voltage or current level, and at least one of the primary timing intervals not divided being an equalizing pulse to substantially charge balance the electrical signal throughout the course of any one repetition of the primary cycle wherein the selection of said primary and secondary timing intervals, and of said voltage or current levels within each, cause said electrical signal to emulate a specific, defined mathematical function having an amplitude which varies with time, and wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

111. A method of substantially charge balancing an electrical signal used in biomedical applications said method comprising (a) generating a repeating primary cycle, the primary cycle having at least four primary timing intervals, (b) forming a repeating secondary cycle by dividing at least one of said primary timing intervals into a least two secondary timing intervals, the secondary cycle having a frequency below 200 kHz, (c) selecting a substantially constant voltage or current level during each of the secondary intervals within the primary interval which is divided, or during the whole of the primary interval not divided, and (d) substantially charge balancing throughout the course of any one repetition of the primary cycle by selecting at least one of the primary timing intervals not divided as an equalizing pulse, wherein the selection of said primary and secondary timing intervals, and of said voltage or current levels within each, cause said electrical signal to emulate a specific, defined mathematical function having an amplitude which varies with time, and wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

112. An apparatus for substantially charge balancing an electrical signal used in biomedical applications, said apparatus comprising (a) means for generating a repeating primary cycle, the primary cycle having at least four primary timing intervals, and (b) means for generating a repeating secondary cycle formed by dividing at least one of said primary timing intervals into a least two secondary timing intervals, the secondary cycle having a frequency below 200 kHz, each of the secondary intervals within the primary interval which is divided having a substantially constant voltage or current level, the whole of the primary interval not divided having a substantially constant voltage or current level, and at least one of the primary timing intervals not divided being an equalizing pulse to substantially charge balance the electrical signal throughout the course of any one repetition of the primary cycles wherein the selection of said primary and secondary timing intervals, and of said voltage or current levels within each, cause said electrical signal to emulate a specific, defined mathematical function having an amplitude which varies with time, and wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

113. An apparatus comprising a processor programmed and connected to produce an electrical signal used in biomedical applications, said electrical signal comprising (a) a repeating primary cycle, the primary cycle having at least four primary timing intervals, and (b) a repeating secondary cycle formed by dividing at least one of said primary timing intervals into at least two secondary timing intervals, the secondary cycle having a frequency below 200 kHz, each of the secondary intervals within the primary interval which is divided having a substantially constant voltage or current level, the whole of the primary interval not divided having a substantially constant voltage or current level, and at least one of the primary timing intervals not divided being an equalizing pulse to substantially charge balance the electrical signal throughout the course of any one repetition of the primary cycle, wherein said biomedical application comprises pain relief, stimulation of tissue growth, acceleration of tissue healing, stimulation of bone growth, acceleration of bone healing, improvement of bone healing, improvement of bone density, reduction of tissue inflammation, repair of tissue damage, reduction of tissue swelling, promotion of tissue graft survival, promotion of tissue graft survival, modification of blood flow, enhancement of biochemical production, enhancement of tissue biochemical production, devitalization of organisms, enhancement of joint repair, enhancement of joint replacement, enhancement of blood storage, and improvement of neurological conditions.

\* \* \* \* \*

UNITED STATES PATENT AND TRADEMARK OFFICE
CERTIFICATE OF CORRECTION

PATENT NO. : 7,117,034 B2  Page 1 of 1
APPLICATION NO. : 10/875801
DATED : October 3, 2006
INVENTOR(S) : James W. Kronberg It is certified that error appears in the above-identified patent and that said Letters Patent is hereby corrected as shown below:

Claim 97, column 72, line 5 "The method as recited in claim 57," should be changed to -- The method as recited in claim 95, --.

Signed and Sealed this

Eighth Day of January, 2008

JON W. DUDAS
*Director of the United States Patent and Trademark Office*